(12) United States Patent
Bassaganya-Riera et al.

(10) Patent No.: US 8,993,624 B2
(45) Date of Patent: Mar. 31, 2015

(54) METHOD OF PREVENTING AND TREATING INFLAMMATORY DISEASES AND DISORDERS WITH ABSCISIC ACID

(75) Inventors: Josep Bassaganya-Riera, Blacksburg, VA (US); Amir Guri, San Diego, CA (US); Raquel Hontecillas, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 84 days.

(21) Appl. No.: 13/700,037

(22) PCT Filed: May 26, 2011

(86) PCT No.: PCT/US2011/038063
§ 371 (c)(1),
(2), (4) Date: Feb. 15, 2013

(87) PCT Pub. No.: WO2011/150160
PCT Pub. Date: Dec. 1, 2011

(65) Prior Publication Data
US 2013/0142825 A1  Jun. 6, 2013

Related U.S. Application Data

(60) Provisional application No. 61/348,326, filed on May 26, 2010.

(51) Int. Cl.
| | | |
|---|---|---|
| A61K 31/19 | (2006.01) | |
| A01N 37/00 | (2006.01) | |
| A61K 39/145 | (2006.01) | |
| A61K 45/00 | (2006.01) | |
| A61K 39/12 | (2006.01) | |
| A61K 31/22 | (2006.01) | |
| A61K 39/39 | (2006.01) | |

(52) U.S. Cl.
CPC ............... *A61K 31/19* (2013.01); *A61K 31/22* (2013.01); *A61K 39/39* (2013.01)
USPC ............. 514/557; 424/209.1; 424/278.1; 424/204.1; 424/211.1; 424/244.1

(58) Field of Classification Search
USPC ............. 514/557; 424/209.1, 278.1, 204.1, 424/211.1, 243.1, 244.1, 234.1
See application file for complete search history.

(56) References Cited

U.S. PATENT DOCUMENTS

2007/0184060 A1* 8/2007 Bassaganya-Riera et al. .................. 424/184.1

FOREIGN PATENT DOCUMENTS

EP  0240257  * 7/1987

OTHER PUBLICATIONS

Patient.Co.uk , 3 pgs (2012).*
Respiratory Syncytial Virus infection (Gale Encyclopedia of Medicine, 3rd ed (2006), p. 8).*
Bassaganya-Riera et al.; Mechanisms of Action and Medicinal Applications of Abscisic Acid; Current Medicinal Chemistry; (2010); pp. 1-12; vol. 17; No. 1; Bentham Science Publishers Ltd.
Guri, Amir J, et al; Abscisic Acid Synergizes with Rosiglitazone to Improve Glucose Tolerance and Down-Modulate Macrophage Accumulation in Adipose Tissue; Possible Action of the cAMP/PKA/PPAR Y axis; Clinical Nutrition; (2010); pp. 646-653; vol. 29; Elsevier Ltd and European Society for Clinical Nutrition and Metabolism.
Guri, Amir J, et al; Loss of PPARY in Immune Cells Impairs the Ability of Abscisic Acid to Improve Insulin Sensitivity by Suppressing Monocyte Chemoattractant Protein-1 Expression and Macrophage Infiltration into White Adipose Tissue; Journal of Nutritional Biochemistry; (2008); pp. 216-228; vol. 19.
Guri, Amir J. et al.; Dietary Abscisic Acid Ameliorates Glucose Tolerance and Obesity-Related Inflammation in db/db Mice Fed High-Fat Diets; Clinical Nutrition; (2007); pp. 107-116; vol. 26; Elsevier Ltd and European Society for Clinical Nutrition and Metabolism.
Guri, Amir J et al.; Abscisic Acid Ameliorates Atherosclerosis by Suppressing Macrophage and CD4+ T Cell Recruitment into the Aortic Wall; Journal of Nutritional Biochemistry; (2010); pp. 1178-1185; vol. 21.
Guri, Amir J. et al.; Abscisic Acid Ameliorates Experimental IBD by Downregulating Cellular Adhesion Molecule Expression and Suppressing Immune Cell Infiltration; Clinical Nutrition; (2010) pp. 824-831; vol. 29; Elsevier.
Bruzzone, Satina, et al.; Abscisic Acid is an Endogenous Stimulator of Insulin Release from Human Pancreatic Inlets with Cyclic ADP Ribose as Second Messenger; The Journal of Biological Chemistry; (2008); pp. 32188-32197; vol. 283; No. 47; The American Society for Biochemistry and Molecular Biology, Inc.
Lehmann, Jurgen M. et al.; An Antidiabetic Thiazolidinedione is a High Affinity Ligand for Peroxisome Proliferator-Activated Receptor Y (PPARY); The Journal of Biological Chemistry; (1995) pp. 12953-12956; vol. 270; No. 22; The American Society for Biochemistry and Molecular Biology, Inc.
Jump, Donald B, et al.; Regulation of Gene Expression by Dietary Fat; Annu. Rev. Nutr.; (1999); pp. 63-90; vol. 19; Annual Reviews.
Ricote, Mercedes, et al.; The Peroxisome Proliferator-Activated Receptor-Y is a Negative Regulator of Macrophage Activation; Nature; (Jan. 1998); pp. 79-82; vol. 391; MacMillan Publishers Ltd.
Kelly, Denise, et al.; Commensal Anaerobic Gut Bacteria Atteuate Inflammation by Regulating Nuclear-Cytoplasmic Shuttling of PPAR-Y and RelA; Nature Immunology; (Jan. 2004); pp. 104-112; vol. 5; No. 1; Nature Publishing Group.
Pascual, Gabriel, et al.; A SUMOylation-Dependent Pathway Mediates Transpression of Inflammatory Response Genes by PPAR-Y; Nature; (Sep. 2005); pp. 759-763; vol. 437; Nature Publishing Group.
Bassaganya-Riera, Josep, et al.; Activation of PPAR Y and δ by Conjugated Linoleic Acid Mediates Protection From Experimental Inflammatory Bowel Disease; Gastroenterlogy; (2004); pp. 777-791; vol. 127; No. 3; The American Gastroenterological Association.

(Continued)

*Primary Examiner* — Shirley V Gembeh
(74) *Attorney, Agent, or Firm* — Blank Rome LLP

(57) ABSTRACT

The present invention relates to the use of a therapeutically effective amount of abscisic acid (ABA) or its analogs to treat or prevent inflammation induced by exposure to lipopolysaccharide (LPS) or respiratory inflammation. The invention also relates to methods and composition for enhancing vaccine efficacy using ABA.

6 Claims, 27 Drawing Sheets

(56) References Cited

OTHER PUBLICATIONS

Kim, So Ri, et al.; Involvement of IL-10 in Peroxisome Proliferator-Activated Receptor Y-Mediated Anti-Inflammatory Response in Asthma; Molecular Pharmacology; (2005); pp. 1568-1575; vol. 68; No. 6; The American Society for Pharmacology and Experimental Therapeutics.

Hammad, Hamida, et al.; Activation of Peroxisome Proliferator-Activated Receptor-Y in Dendritic Cells Inhibits the Development of Eosinophilic Airway Inflammation in a Mouse Model of Asthma; American Journal of Pathology; (Jan. 2004); pp. 263-271; vol. 164; No. 1; American Society for Investigative Pathology.

Lewis, James D, et al; Rosiglitazone for Active Ulcerative Colitis: A Randomized Placebo-Controlled Trail; Gastroenterlogy; (2008); pp. 688-695; vol. 134; The AGA Institute.

Nesto, Richard W., et al; Thiazolidinedione Use, Fluid Retention, and Congestive Heart Failure; Circulation; (2003); pp. 2941-2948; vol. 108; The American Heart Association.

Yang, Tianxin, et al; Renal and Vascular Mechanisms of Thiazolidinedione-Induced Fluid Retention; PPAR Research; (2008); pp. 1-8; vol. 2008; Hindawi Publishing Corporation.

Pettersen, Eric F, et al; UCSF Chimera-A Visualization System for Exploratory Research and Analysis; Journal of Computational Chemistry; (2004); pp. 1605-1612; vol. 25; No. 13; Wiley Periodicals, Inc.

Gampe Jr., Robert T, et al; Asymmetry in the PPARY/RXRα Crystal Structure Reveals the Molecular Basis of Heterodimerization Among Nuclear Receptors; Molecular Cell; (2000); pp. 545-555; vol. 5; Cell Press.

Shirey, Kari Ann, et al.; Francisella Tularensis Live Vaccine Strain Induces Macrophage Alternative Activation as a Survival Mechanism; The Journal of Immunology; (2008); pp. 4159-4167; vol. 181; The American Association of Immunologists, Inc.

Hontecillas, Raquel, et al.; Perisome Proliferator-Activated Receptor Y is Required for Regulatory CD4+ T Cell-Mediated Protection Against Colitis; The Journal of Immunology; (2007); pp. 2940-2949; vol. 178; The American Association of Immunologists, Inc.

Bassaganya-Riera, Josep, et al.; PPAR Y is Highly Expressed in F4/80 hi Adipose Tissue Macrophages and Dampens Adipose-Tissue Inflammation; Cellular Immunology; (2009); pp. 138-146; vol. 258; Elsevier Inc.

Willems, Fabienne, et al.; Phenotype and Function of Neonatal DC; European Journal of . Immunology; (2009); pp. 26-35; vol. 39; Wiley-VCH Verlag GmbH & Co.

Gentleman, Robert C, et al.; Bioconductor: Open Software Development for Computational Biology and Bioinformatics; Genome Biology; (2004); vol. 5; Issue 10; Article R80; BioMed Central Ltd.

Gautier, Laurent, et al.; Affy-Analysis of Affymetrix GeneChip Data at the Probe Level; Bioinformatics; (2004); pp. 307-315; vol. 20; No. 3; Oxford University Press.

Irizayyr, Rafael A, et al.; Exploration, Normalization, and Summaries of High Density Oligonucleotide Array Probe Level Data; Biostatistics; (2003); pp. 249-264; vol. 4; No. 2; Oxford University Press.

Gampe Jr, Robert T, et al.; Asymmetry in the PPARY/RXRα Crystal Structure Reveals the Molecular Basis of Heterodimerization Among Nuclear Receptors; Molecular Cell; (Mar. 2000); pp. 545-555; vol. 5; Cell Press.

Itoh, Toshimasa, et al.; Structural Basis for the Activation of PPARY by Oxidized Fatty Acids; Nature Structural & Molecular Biology; (Sep. 2008); pp. 924-931; vol. 15; No. 9; Nature Publishing Group.

Nolte, Robert T, et al.; Ligand Binding and Co-Activator Assembly of the Peroxisome Prolifer-Activated Receptor-Y; Nature; (Sep. 1998); pp. 137-143; vol. 395; Macmillan Publishers Ltd.

Sturla, Laura et al; LANCL2 is Necessary for Abscisic Acid Binding and Signaling in Human Granulocytes and in Rat Insulinoma Cells; The Journal of Biological Chemistry; (Oct. 2009); pp. 28045-28057; vol. 284; No. 41; The American Society for Biochemistry and Molecular Biology, Inc.

Bruzzone, Santina et al.; Abscisic Acid is an Endogenous Stimulator of Insulin Release from Human Pancreatic Islets with Cyclic ADP Ribose as Second Messenger; The Journal of Biological Chemistry; (Nov. 2008); pp. 32188-32197; vol. 283; No. 47; The American Society for Biochemistry and Molecular Biolog , Inc.

Magnone, Mirko et al.; Abscisic Acid Release by Human Monocytes Activates Monocytes and Vascular Smooth Muscle Cell Responses Involved in Atherogenesis; The Journal of Biological Chemistry; (Jun. 2009); pp. 17808-17818; vol. 284; No. 26; The American Society for Biochemistry and Molecular Biology, Inc.

Welch, John S et al.; PPARY and PPARδ Negatively Regulate Specific Subsets of Lipopolysaccharide and IFN-Y Target Genes in Macrophages; PNAS; (May 2003); pp. 6712-6717; vol. 100; No. 11.

Crosby, Michelle B et al.; Perisome Proliferation-Activated Receptor(PPAR)Y is not Necessary for Synthetic PPARY Agonist Inhibition of Inducible Nitric-Oxide Synthase and Nitric Oxide; The Journal of Pharmacology and Experimental Therapeutics; (2002); pp. 69-76; vol. 312; No. 1.

Tsavkelova, E.A. et al.; Hormones and Hormone-Like Substances of Microorganisms: A Review; Applied Biochemistry and Microbiology; (2006); pp. 229-235; vol. 42; No. 3;.

Zocchi, Elena et al.; The Teperature-Signaling Cascade in Sponges Involves a Heat-Gated Cation Channel, Abscisic Acid, and Cyclic ADP-Ribose; PNAS; (Dec. 2001); pp. 14859-14864; vol. 98; No. 26.

Zocchi, Elena et al.; ABA- and cADPR-Mediated Effects on Respiration and Filtration Downstream of the Temperature-Signaling Cascade in Sponges; Journal of Cell Science; (2003); pp. 629-636; vol. 116; The Company of Biologists Ltd.

Bruzzone, Santina et al.; Abscisic Acid is an Endogenous Cytokine in Human Granulocytes with Cyclic ADP-Ribose as Second Messenger; PNAS; (Apr. 2007); pp. 5759-5764; vol. 104; No. 14.

Lu, Pinyi et al.; Molecular Modeling of Lanthionine Synthetase Component C-Like Protein 2: A Potential Target for the Discovery of Novel Type Diabetes Prophylactics and Therapeutics; Journal Mol. Model.; (2011); pp. 543-553; vol. 17: Springer-Verlag.

Chung, Charlotte H. Y. et al.; Identification of Lanthionine Synthase C-Like Protein-1 as a Prominent Glutathione Binding Protein Expressed in the Mammalian Central Nervous System; Biochemistry; (2007); pp. 3262-3269; vol. 46; The American Chemical Society.

Zhang, Wenchi et al.; Structure of Human Lanthionine Synthetase C-Like Protein 1 and it's Interaction with Eps8 and Glutathione; Genes & Development; (2009); pp. 1387-1392; vol. 23.

Lazennec, Gwendal et al.; Activation of Perisome Proliferator-Activated Receptors (PPARs) by Their Ligands and Protein Kinase a Activators; Molecular Endocrinology; (2000); pp. 1962-1975; vol. 14; No. 12; The Endocrine Society.

Saito, Yukinori et al.; Suppression of Nephrin Expression by TNF-α Via Interfering with the cAMP-Retinoic Acid Receptor Pathway; Am. J. Physiol Renal Physiol; (Mar. 2010); pp. 1436-1444; vol. 298; The American Physiological Society.

Dubuquoy, Laurent et al.; Impaired Expression of Perisome Proliferator-Activated Receptor Y in Ulcerative Colitis; Gastroenterlogy; (2003); pp. 1265-1276; vol. 124.

Szanto, Attila et al.; Retinoids Potentiate Perisome Proliferator-Activated Receptor Y Action in Differentiation, Gene Expression, and Lipid Metabolic Processes in Developing Myeloid Cells; Molecular Pharmacology; (2005); pp. 1935-1943; vol. 67; The American Society for Pharmacology and Experimental Therapeutics.

Adolfsson, Oskar et al.; Vitamin E-Enhanced IL-2 Production in Old Mice: Naive but not Memory T Cells Show Increased Cell Division Cycling and IL-2-Producing Capacity1; The Journal of Immunology; (2001); pp. 3809-3817; vol. 167; The Journal of Immunology Association of Immunologists, Inc.

O'Shea, Marianne et al.; Immunomodulatory Properties of Conjugated Linoleic Acid1-3; Am. J. Clin. Nutr.; (2004); pp. 1199-1206; vol. 79; American Society for Clinical Nutrition.

Duser, Monika G et al.; Platform AR: Membrane Protein Function; (Mar. 2009).

Agrawal, Amit et al.; Normoxic Stabilization of HIF-1α Drives Glycolytic Metabolism and Regulates Aggrecan Gene Expression in Nucleus Pulposus Cells of the Rat Intervertebral Disk; Am. J. Cell Physiol; (2007); pp. 621-631; vol. 293; The American Physiological Society.

(56) References Cited

OTHER PUBLICATIONS

Nechushtan, Hovav et al.; The Physiological Role of Lysyl tRNA Synthetase in the Immune System; Advances in Immunology; (2009); vol. 103; Elsevier Inc.

Park, Sang Hyu et al.; Human lysyl-tRNA Synthetase is Secreted to Trigger Proinflammatory Response; PNAS; (May 2005); pp. 6356-6361; vol. 102; No. 18.

Levine, Stuart M et al.; Anti-Aminoacyl tRNA Synthetase Immune Responses: Insights into the Pathogenesis of the Idiopathic Inflammatory Myopathies; Curr. Opin. Rheumatol; (2003); pp. 708-713; vol. 15; Lippincott Williams & Wilkins.

Yang, Chia-Ron et al.; Thiazolidinediones Inhibit TNF-a-Mediated Osteoclast Differentiation of Raw264.7 Macrophages and Mouse Bone Marrow Cells Through Downregulation of Nfatc1; Shock; (Jun. 2010); pp. 662-667; vol. 33; No. 6; The Shock Society.

Baillie, Rebecca A et al.; A Novel 313-L1 Preadipocyte Variant that Expresses PPARY2 and RXRα but does not Undergo Differentiation; Journal of Lipid Research; (1998); pp. 2048-2053; vol. 39.

Chung, Su Wol et al.; Inhibition of Interleukin-4 Production in CD4+ T Cells by Peroxisome Proliferator-Activated Receptor-Y (PPAR-Y) Ligands: Involvement of Physical Association Between PPAR-Y and the Nuclear Factor of Activated T Cells Transcription Factor; Molecular Pharmacology; (2003); pp. 1169-1179; vol. 64; No. 5; The American Society for Pharmacology and Experimental Therapeutics.

Teismann, Peter, PhD, et al.; Pathogenic Role of Glial Cells in Parkinson's Disease; Movement Disorders; (2003); pp. 121-129; vol. 18; No. 2; Movement Disorder Society.

Herrera, A. J. et al.; The Single Intranigral Injections of LPS as a New Model for Studying the Selective Effects of Inflammatory Reactions on Dopaminergic System; Neurobiology of Disease; (2000); pp. 429-447; vol. 7; Academic Press.

Jaeger, Laura B et al.; Lipopolysaccharide Alters the Blood-Brain Barrier Transport of Amyloid β Protein: A Mechanism for Inflammation in the Progression of Alzheimer's Disease; Brain, Behavior, and Immunity; (2009); pp. 507-517; vol. 23.

Butterfield, D. Allan et al.; Evidence of Oxidative Damage in Alzheimer's Disease Brain: Central Role for Amyloid β-Peptide; Trends in Molecular Medicine; (Dec. 2001); pp. 548-554; vol. 7; No. 12; Elsevier Science Ltd.

McGillicuddy, Fiona C et al.; Inflammation Impairs Reverse Cholesterol Transport in Vivo; Circulation; (2009); pp. 1135-1145; vol. 119; The American Heart Association.

Keuht, Michael L et al; Severely Obese have Greater LPS-Stimulated TNF-a Production Than Normal Weight African-American Women; Obesity; (Mar. 2009); pp. 447-451; vol. 17; No. 3; Nature Publishing Group.

Jong, Menno D De et al.; Fatal Outcome of Human Influenza A (H5N1) is Associated with High Viral Load and Hypercytokinemia; Nature Medicine; (Oct. 2006); pp. 1203-1207; vol. 12; No. 10; Nature Publishing Group.

Kash, John C et al.; Genomic Analysis of Increased Host Immune and Cell Death Responses Induced by 1918 Influenza Virus; Nature; (Oct. 2006); pp. 578-581; vol. 443; Nature Publishing Group.

Gill, James R et al.; Pulmonary Pathologic Findings of Fatal 2009 Pandemic Influenza A/H1N1 Viral Infections; Archives of Pathology & Laboratory Medicine; Feb. 2010); vol. 134; Issue 2; ProQuest Information and Learning.

Lewis, Stephanie N et al.; Virtual Screening as a Technique for PPAR Modulator Discovery; PPAR Research; (2010); pp. 1-10; vol. 2010; Hindawi Publishing Corporation.

Riera-Bassaganya, Josep et al.; Abscisic Acid Regulates Inflammation Via Ligand-Binding Domain-Independent Activation of Peroxisome Proliferator-Activated Receptor Y; Journal of Biological Chemistry; (Jan. 2011); pp. 2504-2516; vol. 286; No. 4; The American Society of Biochemistry and Molecular Biology, Inc.

Guri, Amir J et al.; T Cell PPARY is Required for the Anti-Inflammatory Efficacy of Abscisic Acid Against Experimental IBD; Journal of Nutritional Biochemistry; (2011); pp. 812-819; vol. 22; Elsevier Inc.

Herbert, Andrew S et al.; Incorporation of membrane-Bound, Mammalian-Derived Immunomodulatory Proteins into Influenza Whole Virus Vaccines Boost Immunogenicity and Protection Against Lethal Challenge; Virology Journal; (2009); pp. 1-17; vol. 6; No. 42; BioMed Central Ltd.
Becker, Julien et al.; Regulation of Inflammation by PPARs: a Future Approach to Treat Lung Inflammatory Diseases?; Fundamental & Clinical Pharmacology; (2006); pp. 1-19; Blackwell Publishing Ltd.
Cui, Yongzhi et al.; Loss of the Peroxisome Proliferation-Activated Receptor Gamma (PPARY) does not Affect Mammary Development and Propensity for Tumor Formation but Leads to Reduced Fertility; The Journal of Biological Chemistry; (2002); pp. 17830-17835; vol. 277; No. 20; JBC Papers in Press.
Riera-Bassaganya, J et al.; Mechanisms of Action and Medicinal Applications of Abscisic Acid; Current Medicinal Chemistry; (2010); pp. 1-12; vol. 17; No. 1; Bentham Science Publishers Ltd.
Jr, Aldridge, Jerry R et al.; TNF/iNOS-Producing Dentritic Cells are the Necessary Evil of Lethal Infleunza Virus Infection; PNAS; (Mar. 2009); pp. 5306-5311; vol. 106; No. 13.
Reed, L. J. et al.; A Simple Method of Estimating Fifty Per Cent Endpoints; The American Journal of Hygiene; (May 1938); pp. 493-497; vol. 27; No. 3.
Verheije, M. H. et al.; Chimeric Arteriviruses Generated by Swapping of the M Protein Ectodomain Rule Out a Role of this in Viral Targeting; Virology; (2002); pp. 364-373; vol. 303; Elsevier Science.
Fang, Rui et al.; Construction and Immunogenicity of Pseudotype Baculovirus Expressing Toxoplasma Gondii GAG1 Protein in BALB/c Mice Model; Vaccine; (2010); pp. 1803-1807; vol. 28; Elsevier Ltd.
Wissink, E. H. J. et al.; Envelope Protein Requirements for the Assembly of Infections Virions of Porcine Reproductive and Respiratory Syndrome Virus; Journal of Virology; (Oct. 2002); pp. 12495-12506; vol. 79; No. 19; American Society for Microbiology.
Zhang, Xin-Xin et al.; Broadly Cross-Reactive Mimotope of Hypervariable Region 1 of Hepatitis C Virus Derived from DNA Shuffling and Screened by Phage Display Library; Journal of Medical Virology; (2003); pp. 511-517; vol. 71; Wiley-Liss, Inc.
Zuckermann, Federico A et al.; Assessment of the Efficacy of Commercial Porcine Reproductive and Respiratory Syndrome Virus (PRRSV) Vaccines Based on Measurement of Serologic Response, Frequency of Gamma-IFN-Producing Cells and Virological Parameters of Protection Upon Challenge; Veterinary Microbiology; (2007); pp. 69-85; vol. 123; Elsevier B.V.
Zhao, Huimin et al.; Molecular Evolution by Staggered Extension Process (StEP) in Vitro Recombination; Nature Biotechnology; (Mar. 1998); pp. 258-261; vol. 16; Nature Publishing Group.
Zheng, Qisheng et al.; Co-Expressing GP5 and M Proteins Under Different Promoters in Recombinant Modified Vaccinia Virus Ankara (RMVA)-Based Vaccine Vector Enhanced the Humoral and Cellular Immune Responses of Porcine Reproductive and Respiratory Syndrome Virus (PRRSV); Virus Genes; (2007); pp. 585-595; vol. 35; Springer Science+Business Media, LLC.
Zhang, Yan-Jin et al.; Suppression of Porcine Reproductive and Respiratory Syndrome Virus Replication by Morpholino Antisense Oligomers; Veterinary Microbiology; (2006); pp. 117-129; vol. 117; Elsevier B.V.

* cited by examiner

TO FIG. 12B

METHOD OF PREVENTING AND TREATING INFLAMMATORY DISEASES AND DISORDERS WITH ABSCISIC ACID

CROSS-REFERENCE TO RELATED APPLICATION

This application claims priority of Provisional U.S. Patent Application No. 61/348,326, filed May 26, 2010, which is incorporated herein by reference.

STATEMENT REGARDING FEDERALLY SPONSORED RESEARCH OR DEVELOPMENT

This invention was made with U.S. Government support from the United States National Institutes of Health under Contract No. 1RO1.AT004308-01. The U.S. Government has certain rights in the invention.

FIELD OF THE INVENTION

The present invention relates to the field of medical treatments for diseases and disorders. More specifically, the present invention relates to the use of a therapeutically effective amount of abscisic acid (ABA) or its analogs to treat or prevent inflammation induced by exposure to lipopolysaccharide (LPS) or respiratory inflammation.

BACKGROUND OF THE INVENTION

Abscisic acid (ABA) is an isoprenoid phytohormone discovered in the early 1960's that has received some attention due to its possible medicinal applications (1). Specifically, oral ABA administration has shown prophylactic and therapeutic efficacy in mouse models of diabetes, inflammatory bowel disease (IBD) and atherosclerosis (2-6). In line with ABA's anti-diabetic effects, there is evidence that endogenously generated ABA at nanomolar concentrations can act locally and enhance the insulin-secreting ability of pancreatic β-cells (7). However, little is known about the role of ABA in the modulation of immune and inflammatory responses and the molecular mechanisms underlying its health effects.

Mechanistically, ABA activates peroxisome proliferator-activated receptor γ (PPAR γ) reporter activity in pre-adipocytes (4) and the deficiency of PPAR γ in immune cells impairs the ability of ABA to normalize glucose concentrations and ameliorate macrophage infiltration in the white adipose tissue of obese mice (3). PPAR γ is a nuclear hormone receptor and the molecular target of the thiazolidinedione (TZD) class of anti-diabetic drugs (8). Its naturally occurring and endogenous agonists include fatty acids, eicosanoids and botanicals (9). PPAR γ suppresses the expression of pro-inflammatory cytokines and chemokines by antagonizing the activities of transcription factors, such as AP-1, STAT and NF-κB (10), enhancing nucleocytoplasmic shuttling of the activated p65 subunit of NF-κB (11), and targeting co-repressor complexes on to inflammatory gene promoters via a SUMOylation-driven process (12). These molecular changes induced by PPAR γ agonists are linked to anti-inflammatory efficacy in mouse models of IBD, encephalomyelitis, rheumatoid arthritis and eosinophilic airway inflammation (13-15). There is also clinical evidence showing that rosiglitazone is efficacious in the treatment of mild to moderate ulcerative colitis in humans (16). However, TZDs are unlikely to be adopted for the treatment of chronic inflammation due to their significant side effects, including fluid retention, weight gain and hepatotoxicity (17) that may be linked to their mechanism of action (18). In contrast to TZDs, the ABA-mediated activation of PPAR γ can be blocked by inhibiting intracellular cAMP production or protein kinase A (PKA) activity (2), suggesting that ABA may trigger an alternative mechanism of PPAR γ activation.

The aim of this study was to determine the role of PPAR γ in ABA's immune modulatory properties during LPS-mediated inflammation and influenza-associated inflammation, characterize ABA-controlled gene regulatory networks, and elucidate the mechanisms of action underlying ABA's anti-inflammatory and immunotherapeutic effects.

SUMMARY OF THE INVENTION

Lipopolysaccharide (LPS) is a component of gram-negative bacteria which has been linked to a number of human inflammatory disorders, including septic shock, obesity related inflammation, Parkinson's Disease, Crohn's Disease, and Alzheimer's Disease (AD). Compounds which can reduce the extent of LPS-induced inflammation may be effective as therapeutic agents for treating some of these underlying conditions. Abscisic acid (ABA) is a natural compound, produced by plants and mammals, which we previously shown to be an effective modulator of inflammation in a number of experimental mammalian disease models, including obesity, cardiovascular disease (CVD), and inflammatory bowel disease (IBD). This application discloses a novel mechanism of action by which ABA and its analogs can regulate immune responses and inflammation involving binding to lanthionine synthetase C-like 2 protein and activation of peroxisome proliferator-activated receptor γ (PPAR γ), a protein noted for its anti-inflammatory effects in macrophages and T cells. The present inventors demonstrate that through this mechanism ABA protects the body from LPS-induced inflammation and damage. Additionally, the present inventors also demonstrate that ABA elicits therapeutic effects to decrease lung inflammation and pathology, ameliorate respiratory disease activity and increase survival following influenza virus infection.

LPS has been linked to a number of human diseases and disorders; among those include the degenerative diseases Parkinson's Disease (PD) and Alzheimer's Disease (AD), septic shock, and cardiovascular disease. Our data demonstrates that ABA treatment reduces LPS-induced inflammation both ex vivo and in vivo in a mammalian model, and therefore suggests that ABA may also be useful in the treatment of human conditions.

For instance, PD is a disease characterized by the degeneration dopaminergic neurons in the substantia nigra (SN) of the brain. The close proximity of these cells to activated microglial cells in the SN has been postulated to contribute to the pathogenesis of PD (58). Microglial cells are highly responsive to LPS treatment, and long term stimulation of LPS has been shown to be neurotoxic (59). Adding to these findings, dopaminergic neurons have been demonstrated to be highly susceptible to LPS-induced neurotoxicity, far much more so than γ-aminobutyric acidergic or serotinergic neurons, and intranigral injection of LPS specifically degenerates dopaminergic neurons via microglial activation (59).

In AD, inflammation has been associated with the decreased clearance of amyloid β from the blood brain barrier (BBB) (60). Brains of AD patients are characterized by neuroinflammation, including increased astrocytes, microglial activation, and pro-inflammatory cytokines, and intraperitoneal injection of LPS has been shown to increase amyloid β and alter BBB transport activity (60, 61).

Recent studies have also indicated that LPS has may play a pathogenic role in obesity-related disorders and CVD. Treatment with LPS has been shown to impair reverse cholesterol transport in rodent models (62), and blood immune cells from obese humans secrete significantly more LPS-induced tumor necrosis factor α (TNF-α) than those from lean individuals (63).

The involvement of LPS-induced inflammation in human disease makes the use of compounds which can safely attenuate the LPS inflammatory response a valuable treatment option, even if the primary goal is to dampen the potential of LPS involvement. Thus, LPS need not be established in the individual's disease pathogenesis for ABA to be considered as a therapeutic option.

Accordingly, an object of the present invention provides methods for treating or preventing LPS-induced inflammation. The methods involve administering to a mammal in need thereof a composition containing abscisic acid (ABA) in amounts sufficient to alter the expression or activity of PPAR γ in a cell of the mammal.

Another object of the present invention provides methods for treating or preventing respiratory inflammation. The methods involve administering to a mammal in need thereof a composition containing abscisic acid (ABA) in amounts sufficient to alter the expression or activity of PPAR γ in a cell of the mammal. The pulmonary inflammation can be caused by infection, for example, by influenza virus or other infectious agents.

The terms "treating" or "preventing" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome. The methods involve administering ABA to a subject suffering from LPS-induced or pulmonary inflammation, or a subject in need of treatment or prevention LPS-induced or pulmonary inflammation. The amount administered should be sufficient to alter the expression or activity of PPAR γ in a cell of the subject.

BRIEF DESCRIPTION OF THE DRAWINGS

The accompanying drawings, which are incorporated in and constitute a part of this specification, illustrate several embodiments of the invention and together with the written description, serve to explain certain principles and details of embodiments of the invention.

(MCP-1) mRNA in mice that received ABA (E). Data points with an asterisk (P<0.05) are significantly different (n=10 mice per treatment and genotype).

FIG. 16 illustrates the effect of ABA treatment on pulmonary expression of PPAR γ, monocyte chemoattractant protein 1 (MCP-1) in cells obtained from the broncholveolar space. Wild-type (WT) or immune/epithelial cell-specific PPAR γ null mice (cKO) mice were fed either a control or an ABA-supplemented diet (100 mg/ABA kg of diet) for 36 days and then challenged with $5 \times 10^4$ tissue culture infectious dose 50 ($TCID_{50}$) of influenza A/Udorn (H3N2) virus. Mice were sacrificed on day 4 post-infection and cells were collected by lavage. ABA treatment for 36 days increased PPAR γ mRNA expression in healthy non-infected WT mice (A) although following infection WT mice fed the control diet had significantly higher levels of PPAR γ, which correlated with higher mRNA expression of macrophage chemoattractant protein-1 and TNFα, compared to the rest of the groups. Data points with different letters (P<0.05) are significantly different (n=10 mice per treatment and genotype).

Figure 17A:
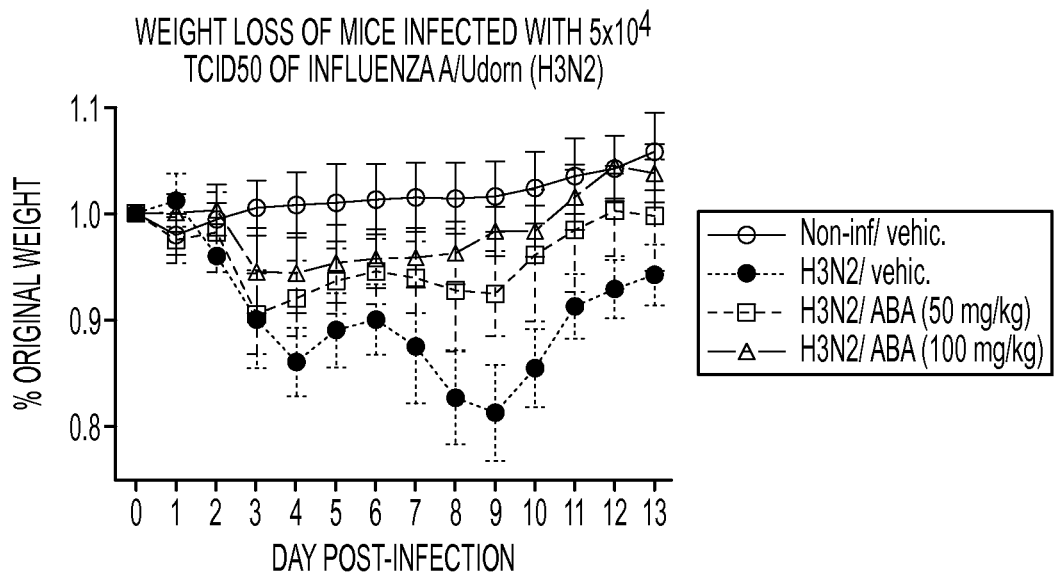
Figure 17B:
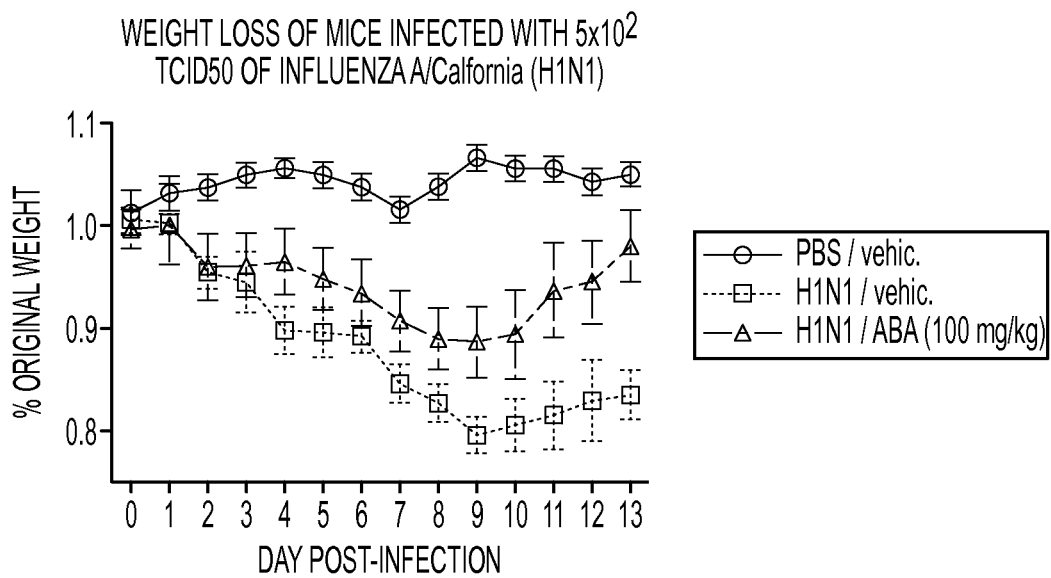

FIG. 17 illustrates the effect of post-exposure ABA treatment on influenza-related weight loss. Wild-type (WT) mice treated with vehicle or ABA (100 mg/ABA kg of body weight) via orogastric gavage daily starting 4 hours following intranasal inoculation of influenza virus. Mice were challenged with $5 \times 10^4$ tissueculture infectious dose 50 ($TCID_{50}$) of influenza A/Udorn (H3N2) virus (top panel) or $5 \times 10^2$ $TCID_{50}$ of pandemic swine-origin influenza A/California H1N1 (bottom panel). ABA treatment for 10 days post-exposure decreased influenza-related weight loss. Data points with different letters (P<0.05) are significantly different (n=10 mice per treatment and genotype).

Figure 18A:
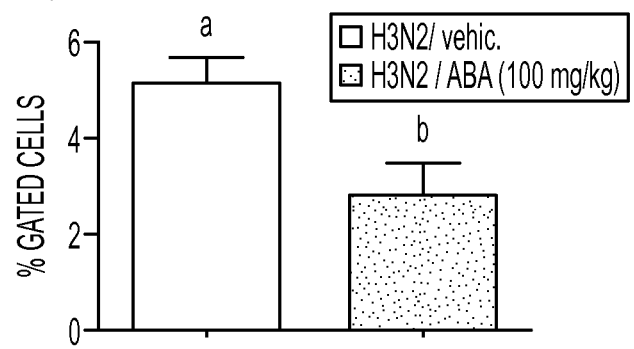
Figure 18B:
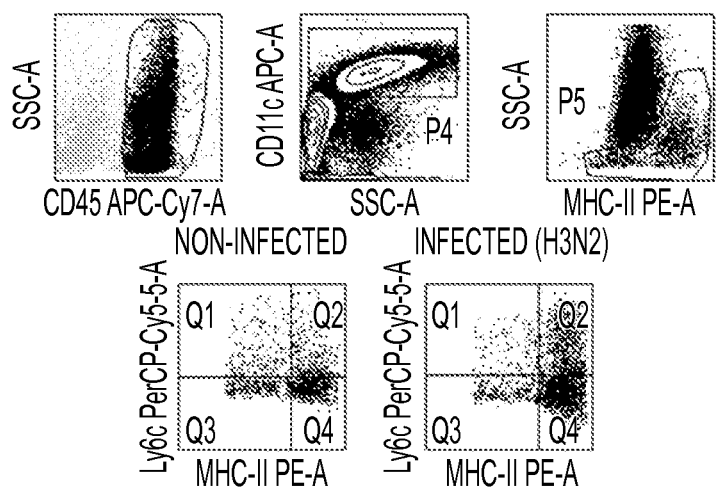
Figure 19A:
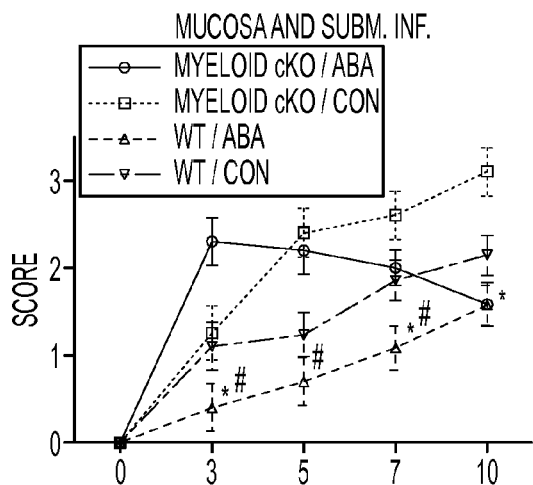
Figure 19B:
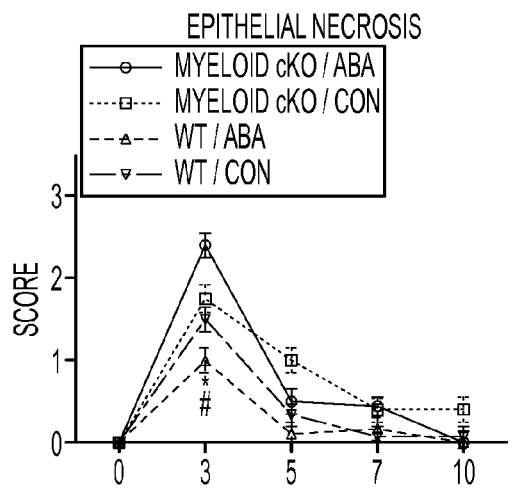
Figure 19C:
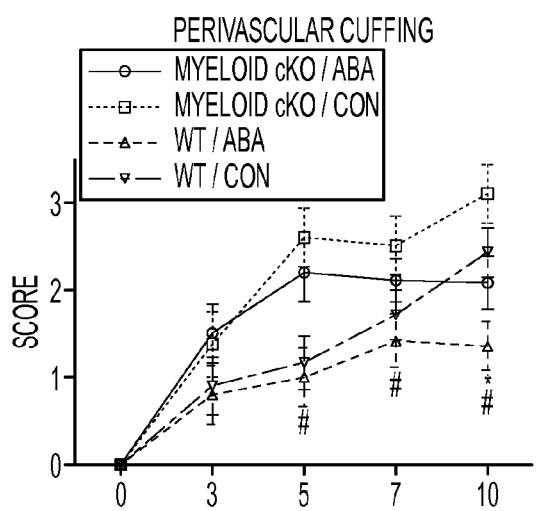
Figure 19D:
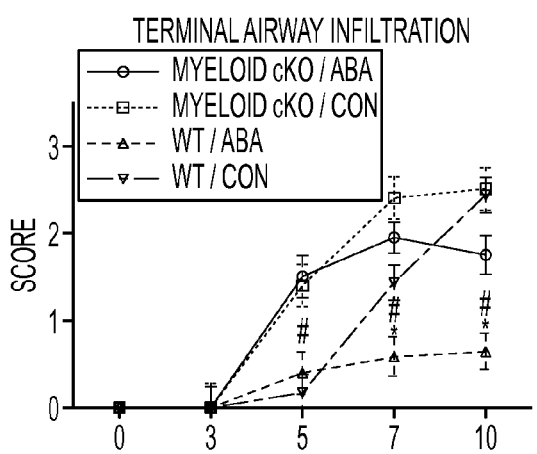
Figure 20A:
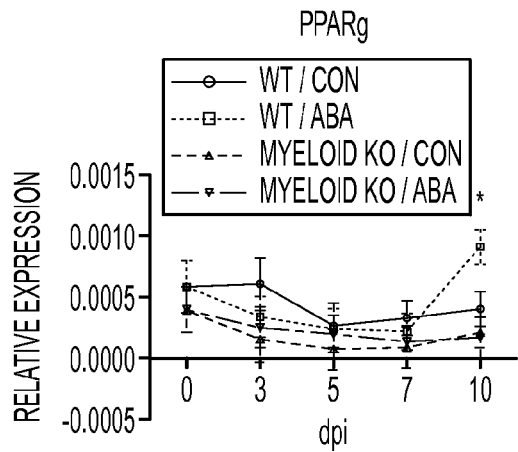
Figure 20B:
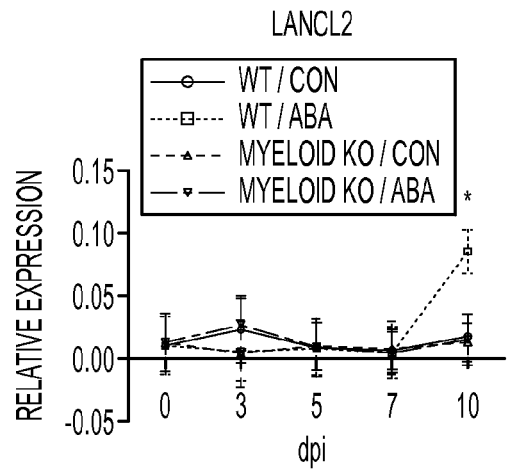
Figure 20C:
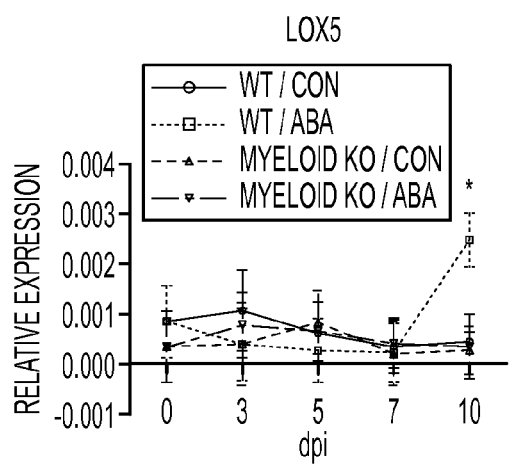
Figure 20D:
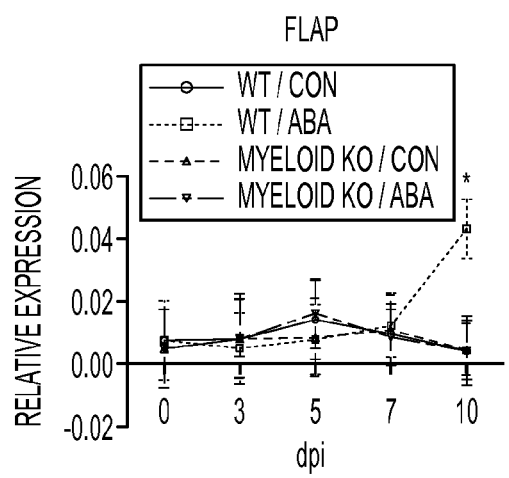

FIG. 18 illustrates the effect of post-exposure ABA treatment on tumor necrosis a (TNFα)/inducible nitric oxide synthase (iNOS)-producing dendritic cells (tipDC). Wild-type (WT) mice treated with vehicle or ABA (100 mg/ABA kg of body weight) via orgogastric gavage daily starting 4 hours following intranasal inoculation of influenza virus. Mice were challenged with $5 \times 10^4$ tissue culture infectious dose 50 ($TCID_{50}$) of influenza A/Udorn (H3N2) virus. Infiltrating tipDCs were phenotypically characterized by flow cytometry on day 7 post-infection. Data points with different letters (P<0.05) are significantly different (n=10 mice per treatment and genotype).

FIG. 19 illustrates the effect of post-exposure ABA treatment on pulmonary histopathology. Wild-type (WT) mice treated with vehicle or ABA (100 mg/ABA kg of body weight) via orogastric gavage daily starting 4 hours following intranasal inoculation of influenza virus. Mice were challenged with $5 \times 10^4$ tissueculture infectious dose 50 ($TCID_{50}$) of influenza A/Udorn (H3N2) virus. Mucosal and submucosal infiltration, epithelial necrosis, terminal airway infiltration and perivascular cuffing were evaluated. Data points with different signs (P<0.05) are significantly different (n=10 mice per treatment and genotype).

FIG. 20 illustrates the effect of post-exposure ABA treatment on pulmonary gene expression. Wild-type (WT) and myeloid-specific PPAR γ null mice (myeloid KO) treated with vehicle or ABA (100 mg/ABA kg of body weight) via orogastric gavage daily starting 4 hours following intranasal inoculation of influenza virus. PPAR γ, LANCL2, 5-lipooxygenase (5-LOX) and 5-lipooxygenase activating protein (FLAP) were assayed. Mice were challenged with $5 \times 10^4$ tissue culture infectious dose 50 ($TCID_{50}$) of influenza A/Udorn (H3N2) virus. Data points with an asterisk (P<0.05) are significantly different (n=10 mice per treatment and genotype).

Figure 21A:
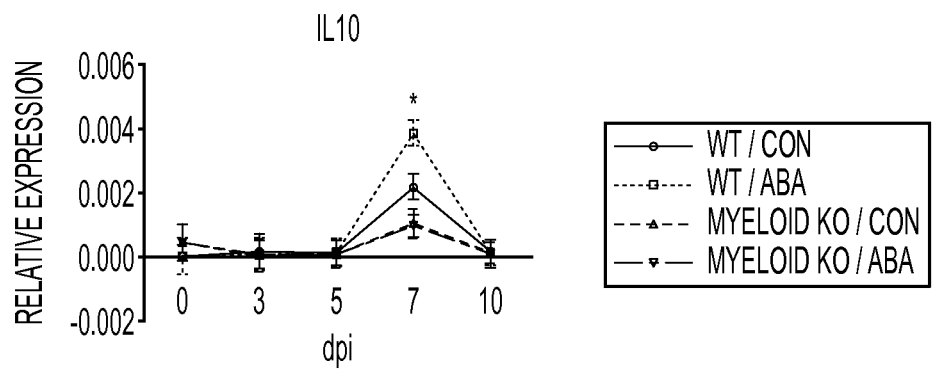
Figure 21B:
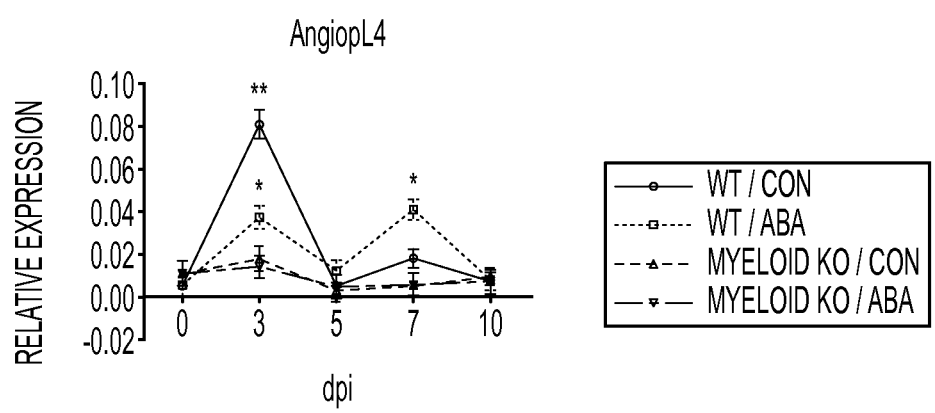

FIG. 21 illustrates the effect of post-exposure ABA treatment on pulmonary gene expression. Wild-type (WT) and myeloid-specific PPAR γ null mice (myeloid KO) treated with vehicle or ABA (100 mg/ABA kg of body weight) via orogastric gavage daily starting 4 hours following intranasal inoculation of influenza virus. Interleukin-10 and angiopoietin like 4 were assayed. Mice were challenged with $5 \times 10^4$ tissue culture infectious dose 50 ($TCID_{50}$) of influenza A/Udorn (H3N2) virus. Data points with an asterisk (P<0.05) are significantly different (n=10 mice per treatment and genotype).

Figure 22A:
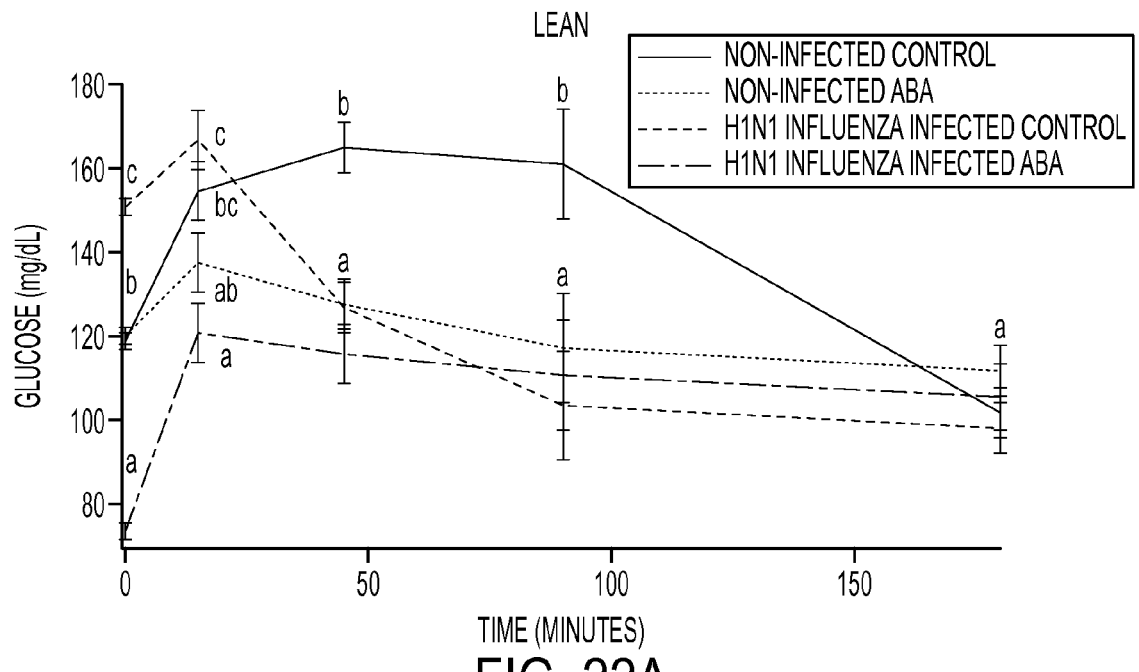
Figure 22B:
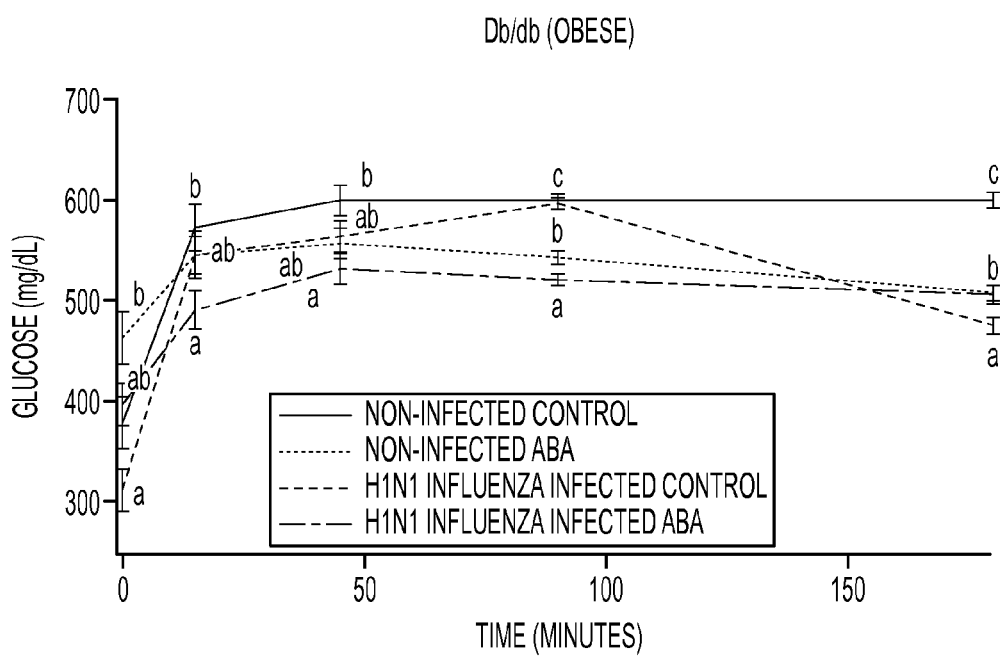

FIG. 22 illustrates the effect of post-exposure ABA treatment on glucose tolerance. Wild-type (WT, A) lean and db/db (obese, B) mice treated with vehicle or ABA (100 mg/ABA kg of body weight) via orogastric gavage daily starting 4 hours following intranasal inoculation of influenza virus. Mice were challenged with $5 \times 10^2$ $TCID_{50}$ of pandemic swine-origin influenza A/California H1N1. ABA treatment for 10 days post-exposure ameliorated glucose tolerance in infected and uninfected mice. Data points with different letters (P<0.05) are significantly different (n=10 mice per treatment and genotype).

Figure 23:
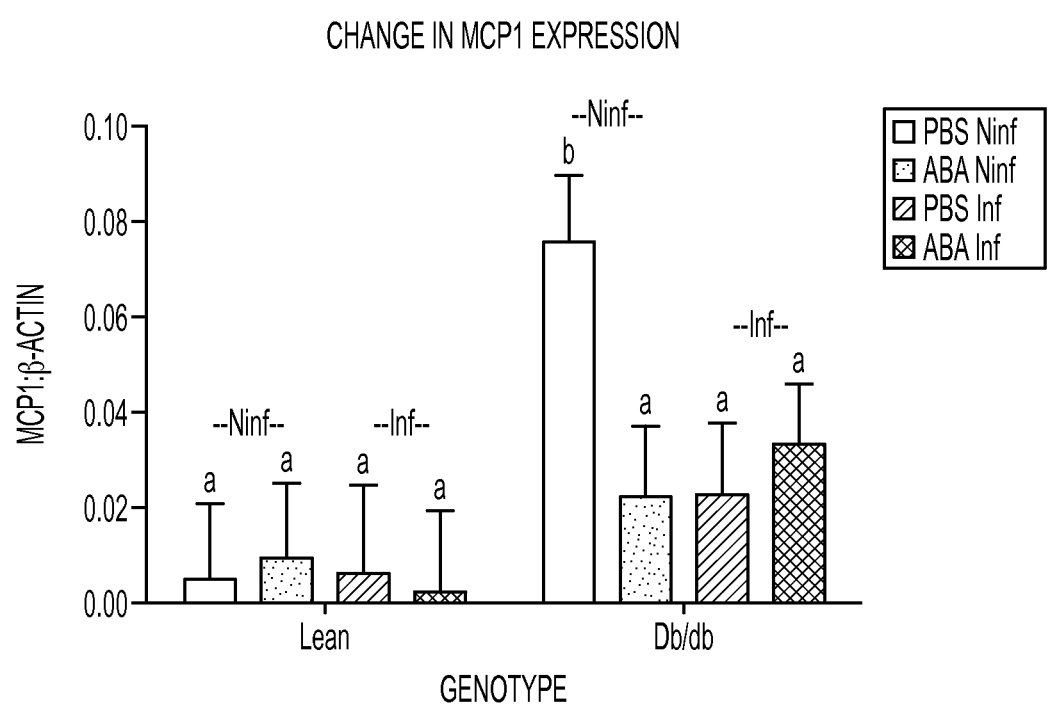

FIG. 23 illustrates the effect of ABA treatment on white adipose tissue (WAT) MCP-1 expression. Wild-type, lean and db/db (obese) mice treated with vehicle or ABA (100 mg/ABA kg of body weight) via orogastric gavage daily starting 4 hours following intranasal inoculation of influenza virus. Mice were challenged with $5 \times 10^2$ $TCID_{50}$ of pandemic swine-origin influenza A/California H1N1. ABA treatment for 10 days dramatically down-regulated MCP-1 expression in WAT. Data points with different letters (P<0.05) are significantly different (n=10 mice per treatment and genotype).

Figure 24A:
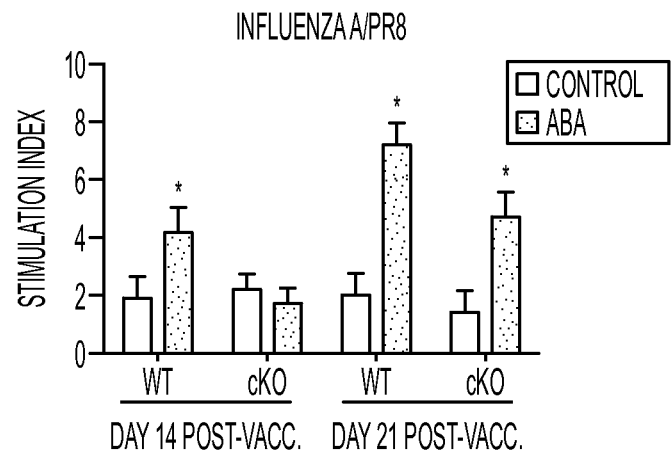
Figure 24B:
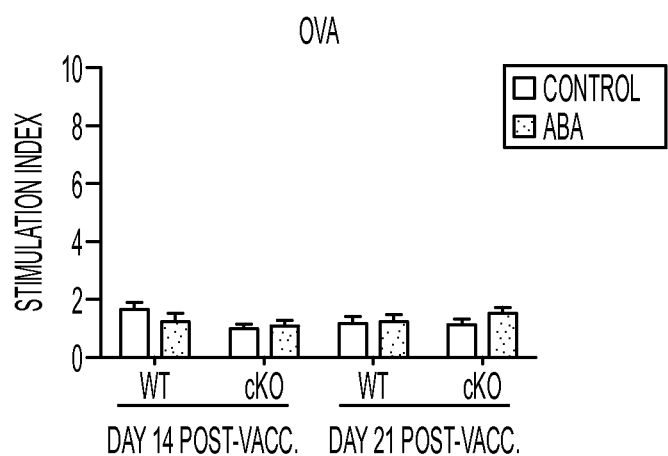

FIG. 24 illustrates the effect of ABA treatment on immune responses to influenza virus in mice vaccinated with inactivated influenza virus antigens. Wild-type (WT) and immune cell-specific PPAR γ null mice (cKO) mice treated with control or ABA (100 mg/kg)-supplemented diets were immunized with an influenza virus vaccine. Antigen-specific lymphoproliferative responses to influenza A/PR8 antigens (A) and ovalbumin (OVA) (B) were analyzed on days 14 and 21 post-vaccination. ABA treatment increased antigen-specific responses to influenza virus on days 14 and 21 post-vaccination. The beneficial effect of ABA on immune responses to vaccination was decreased in cKO mice. Means with an asterisk (P<0.05) are significantly different (n=10 mice per treatment, genotype and time point).

DETAILED DESCRIPTION OF VARIOUS
EMBODIMENTS OF THE INVENTION

The present invention provides new uses for abscisic acid and structurally related compounds. The term abscisic acid (ABA) herein refers to a plant hormone containing a trimethylcyclohexene ring with one or more hydroxy groups (for instance a 6-hydroxy group), a 3-oxo group and an unsaturated side chain in the sixth position of the trimethylcyclohexen ring containing cis-7, trans-9 double bonds, its non-toxic salts, active esters, active isomers, active metabolites and mixtures thereof. Non-toxic salts include, for example, alkyl esters having from 1 to 6 carbon atoms in the alkyl group, as well as mono-, di- and tri- glycerides, and mixtures thereof. Active isomers of abscisic acid include geometrical isomers and its non-toxic salts, e.g., sodium, potassium, calcium and magnesium salts, and its active esters, e.g., alkyl esters having from 1 to 6 carbon atoms in the alkyl group, as well as mono-, di- and tri- glycerides, and mixtures thereof. Active optical isomers of abscisic acid include the (+)-enantiomer and the (−)-enantiomer and its non-toxic salts, e.g., sodium, potassium, calcium and magnesium salts, and its active esters, e.g., alkyl esters having from 1 to 6 carbon atoms in the alkyl group, as well as mono-, di- and tri- glycerides, and mixtures thereof. Active metabolites of abscisic acid include oxygenated abscisic acid analogs, including but not limited to, 8'-hydroxyABA, (+)-7'-hydroxyABA, 2'3'-dihydroABA, 8'-hydroxy-2',3'-dihydroABA and its non-toxic salts, e.g., sodium, potassium, calcium and magnesium salts, and its active esters, e.g., alkyl esters having from 1 to 6 carbon atoms in the alkyl group, as well as mono-, di- and tri- glycerides, and mixtures thereof. Structurally related compounds, include but are not limited to, compounds containing conjugated double bonds (e.g., conjugated dienes, trienes and tetraenes) in the unsaturated side chain and compounds containing a trimethylcyclohexene ring with or without hydorxy moieties. For ease of reference, all such compounds are referred to herein generally at times as abscisic acid or ABA.

Abscisic acid has previously been extracted from leaves of Lupin (Lupinus cosentinii), Apricot (Prunus armeniaca), Avocado (Persea Americana), Sunflower (Helianthus annuus), Grapevine (Vitis vinifera), Tomato (Lycopersicon esculentum), Spinach (Spinacia oleracea), Orange (Citrus sinensis) and Mango (Mangifera indica) (46). ABA and its metabolites have also been isolated from Brassica napus and Brassica rapa seed (47) and could also be isolated from fruits and any other plant materials. The abscisic acid compound has been extracted from plant leaves through many procedures, including: 1) methanol extraction; 2) cold water extraction or 3) boiling water extraction (Loveys, 1988). For the methanol extraction, samples of leaf material were homogenized in aqueous methanol, the homogenate was centrifuged and the pellet re-extracted with methanol. Water was added to the combined supernatants before evaporation. The resulting extract was adjusted to a pH of 2.5 and the abscisic acid compound extracted with three washes of ethyl acetate. The ethyl acetate extracts can be further purified by chromatography. The cold water and boiling water methods consist of homogenization of plant materials in cold or boiling water, respectively prior to the ethyl acetate extraction.

Abscisic acid may be a substantially pure single chemical compound or a mixture of one or more abscisic acid compounds as defined above. For example, the abscisic acid may be in the form of an extract obtainable or obtained from plant extracts, either directly or following one or more steps of purification or it can be chemically synthesized. The term substantially pure means having a purity of at least 90% by weight, including all specific integers above 90%. Preferably it has a purity of at least 95% by weight, such as at least 98%, 99%, or 100% or about 100% by weight. For example, the abscisic acid may be in the form of an extract obtainable or obtained from plants, either directly or following one or more steps of purification.

The abscisic acid used in the described methods may be in a free acid form or bound chemically through ester linkages. In its natural form, abscisic acid is heat stable. Abscisic acid may be used in its natural state or in a dried and powdered form. Further, the free acid form of abscisic acid may be converted into a non-toxic salt, such as sodium, potassium or calcium salts, by reacting chemically equivalent amounts of the free acid form with an alkali hydroxide at a basic pH. FIG. 1 depicts ABA and an exemplary compound falling within the definition of abscisic acid and structurally related compounds. Other structurally related compounds are known in the art, such as those disclosed by Hill et al. (45).

In general, the invention provides for use of abscisic acid and structurally related compounds, such as a compound selected from the group consisting abscisic acid, esters thereof, pharmaceutically suitable salts thereof, metabolites thereof, structurally related compounds thereof, or combinations thereof in the treatment and prevention of disorders known to be caused by or worsened by LPS exposure. As used throughout this document, the term ABA and all of its forms are meant to include a compound selected from the group consisting of abscisic acid, esters thereof, pharmaceutically suitable salts thereof, metabolites thereof, structurally related compounds thereof, analogs thereof, or combinations thereof, as disclosed herein.

While not being limited to any particular mode of action, it is possible that abscisic acid and its derivatives and structurally related compounds affect PPAR gamma expression and/or activity, or rather the presence of PPARγ is required for the full anti-inflammatory effects of abscisic acid. However, the invention also contemplates other modes of action, such as by affecting expression or activity of any number of other cellular molecules, including, but not limited to, nuclear receptors that may be activated by ABA, including liver X receptor (LXR), retinoid X receptor (RXR), pregnane X receptor (PXR), vitamin D receptor (VDR), as well as nuclear receptor-independent mechanisms such as membrane initiated signaling through the activation of G protein-coupled receptors and stimulation of intracellular cyclic adenosine monophosphate production.

When practiced, this method can be by way of administering ABA to a subject (an animal, including a human and other mammals) via any acceptable administration route, and allowing the body of the subject to distribute the ABA to the target cell through natural processes. Such routes include, but are not necessarily limited to, oral, via a mucosal membrane (e.g., nasally, via inhalation, rectally, intrauterally or intravaginally, sublingually), intravenously (e.g., intravenous bolus injection, intravenous infusion), intraperitoneally, and subcutaneously. The preferred route of administration is oral.

Administering can likewise be by direct injection to a site (e.g., organ, tissue) containing a target cell (i.e., a cell to be treated). Furthermore, administering can follow any number of regimens. It thus can comprise a single dose or dosing of ABA, or multiple doses or dosings over a period of time. Accordingly, treatment can comprise repeating the administering step one or more times until a desired result is achieved. In embodiments, treating can continue for extended periods of time, such as weeks, months, or years. Those of skill in the art are fully capable of easily developing suitable dosing regimens for individuals based on known parameters in the art.

For oral administration, the effective amount of abscisic acid may be administered in, for example, a solid, semi-solid, liquid, or gas state. Specific examples include tablet, capsule, powder, granule, solution, suspension, syrup, and elixir agents. However, the abscisic acid compound is not limited to these forms.

To formulate the abscisic acid of the present invention into tablets, capsules, powders, granules, solutions, or suspensions, the abscisic acid compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the abscisic acid compound of the present invention may be administered rectally or by injection. For rectal administration, a suppository may be used. The suppository may be prepared by mixing the abscisic acid of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the abscisic acid compound of the present invention may be injected hypodermically, intracutaneously, intravenously, or intramuscularly. Medicinal drugs for such injection may be prepared by dissolving, suspending or emulsifying the abscisic acid of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

For formulating the abscisic acid of the present invention into suspensions, syrups or elixirs, a pharmaceutically suitable solvent may be used. Included among these is the non-limiting example of water.

The amount to be administered will vary depending on the subject, stage of disease or disorder, age of the subject, general health of the subject, and various other parameters known and routinely taken into consideration by those of skill in the medical arts. As a general matter, a sufficient amount of ABA will be administered in order to make a detectable change in the extent of inflammation, which in practice is often related to the amount of pain an individual is experiencing. Suitable amounts are disclosed herein, and additional suitable amounts can be identified by those of skill in the art without undue or excessive experimentation, based on the amounts disclosed herein. Preferably, the ABA is administered in a dosage of about 0.05 to about 1,000 mg ABA per kg of body weight daily, more preferably about 0.5 to about 500 mg of ABA per kg of body weight daily.

ABA may be administered in a form that is acceptable, tolerable, and effective for the subject. Numerous pharmaceutical forms and formulations for biologically active agents are known in the art, and any and all of these are contemplated by the present invention. Thus, for example, ABA can be formulated in an oral solution, a caplet, a capsule, an injectable, an infusible, a suppository, a losenge, a tablet, a cream or salve, an inhalant, and the like.

The ABA compound of the present invention may also be used together with an additional compound having other pharmaceutically suitable activity to prepare a medicinal drug. A drug, either containing ABA as a stand-alone compound or as part of a composition, may be used in the treatment of subjects in need thereof.

The abscisic acid of the present invention may also be administered in the form of an aerosol or inhalant prepared by charging the abscisic acid in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

Abscisic acid may be administered to an animal, including mammals and humans, in need thereof as a pharmaceutical or veterinary composition, such as tablets, capsules, solutions, or emulsions. In a preferred embodiment of the invention, the free acid form of punicic acid is administered. However, administration of other forms of abscisic acid, including but not limited to esters thereof, pharmaceutically-suitable salts thereof, metabolites thereof, structurally related compounds thereof, analogs thereof, and combinations thereof, in a single dose or a multiple dose, are also contemplated by the present invention.

Abscisic acid may also be administered to an animal in need thereof as a nutritional additive, either as a food or nutraceutical supplement.

The abscisic acid is preferably used and/or administered in the form of a composition. Suitable compositions are, preferably, a pharmaceutical composition, a foodstuff or a food supplement. These compositions provide a convenient form in which to deliver the abscisic acid. Compositions of the invention may comprise an antioxidant in an amount effective to increase the stability of the abscisic acid with respect to oxidation.

The amount of abscisic acid that is administered in the method of the invention or that is for administration in the use of the invention is any suitable amount. It is preferably from about 0.05 to about 1,000 mg, more preferably about 0.5 to about 500 mg, of ABA per kg of body weight daily. Suitable compositions can be formulated accordingly. Those of skill in the art of dosing of biologically active agents will be able to develop particular dosing regimens for various subjects based on known and well understood parameters.

A preferred composition according to the invention is a foodstuff. Food products (which term includes animal feed) preferably contain a fat phase, wherein the fat phase contains abscisic acid. The foodstuffs are optionally used as a blend with a complementary fat. For example, the fat may be selected from: cocoa butter, cocoa butter equivalents, palm oil or fractions thereof, palmkernel oil or fractions thereof, interesterified mixtures of those fats or fractions thereof. It may also contain liquid oils, such as those selected from: sunflower oil, high oleic sunflower oil, soybean oil, rapeseed oil, cottonseed oil, fish oil, safflower oil, high oleic safflower oil, corn oil, and MCT-oils. Examples of suitable foodstuffs include those selected from the group consisting of margarines, fat continuous or water continuous or bicontinuous spreads, fat reduced spreads, confectionery products such as chocolate or chocolate coatings or chocolate fillings or bakery fillings, ice creams, ice cream coatings, ice cream inclusions, dressings, mayonnaises, cheeses, cream alternatives, dry soups, drinks, cereal bars, sauces, snack bars, dairy products, clinical nutrition products, and infant formulations.

Other non-limiting examples of compositions are pharmaceutical compositions, such as in the form of tablets, pills, capsules, caplets, multiparticulates (including granules, beads, pellets and micro-encapsulated particles); powders, elixirs, syrups, suspensions, and solutions. Pharmaceutical compositions will typically comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the ABA on the subject.

Pharmaceutically acceptable carriers suitable for use in such compositions are well known in the art of pharmacy. The compositions of the invention may contain about 0.01-99% by weight of abscisic acid, preferably about 50-99%. The compositions of the invention are generally prepared in unit dosage form. Preferably the unit dosage of ABA is from about 0.1 mg to about 1000 mg, more preferably from about 5 mg to about 500 mg. The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain crosslinking or polymerizing agents, stabilizers, antioxidants, light absorbing agents for protecting light-sensitive fills, preservatives, and the like. Preferably, the unit dosage of abscisic acid in the food supplements is from about 0.1 mg to about 1000 mg, more preferably from about 5 mg to about 500 mg.

In general, the term carrier may be used throughout this application to represent a composition with which ABA may be mixed, be it a pharmaceutical carrier, foodstuff, nutritional supplement or dietary aid. The materials described above may be considered carriers of ABA for the purposes of the invention. In certain embodiments of the invention, the carrier has little to no biological activity on PPAR γ.

In one aspect, the invention provides a method of treating or preventing LPS-induced inflammation. Such disorder is known to be caused or worsened by LPS include septic shock, cardiovascular disease, Parkinson's Disease, and Alzheimer's Disease. The method pertains to those individuals who are presently diagnosed with inflammation caused by LPS exposure or to those with a disorder that may be exacerbated if LPS exposure occurs at a time afterwards. In general, the method of treating or preventing according to this aspect of the invention comprises administering to the subject an amount of ABA therapy that is effective in treating or preventing one or more symptoms or clinical manifestations resulting from exposure to LPS, or in preventing development of such symptom(s) or manifestation(s).

Thus, according to the methods of the invention, the invention can provide methods of treatment of a disorder in which it the prevention or attenuation of LPS-induced inflammation is deemed beneficial. The methods of treatment can be prophylactic methods. In embodiments, the method is a method of treating LPS-induced inflammation. In embodiments, the method is a method of preventing LPS-induced inflammation. In yet other embodiments, the method is a method of improving the health status of a subject who stands to benefit from a reduction in LPS-induced inflammation.

In one exemplary embodiment of the invention, the method of reducing LPS-induced inflammation comprises treating a patient without causing discernable side-effects. That is, it has been found that the method of treating according to the present invention, which provides the treatment effect, at least in part, by affecting the expression and/or activation of PPARγ in some cells, provides the beneficial effect without causing a significant gain in weight, for example by fluid retention, in the subject being treated, as compared to other similar subjects not receiving the treatment. While not wishing to be bound by any particular theory as to why this effect is seen, it is likely that treatment with ABA therapy, while causing an increase in PPARγ expression in some cells, does not cause over-expression or over-activation, as is commonly seen with some other (e.g., synthetic) PPAR agonists currently known for treatment of diseases associated with PPAR.

As such, the methods can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood leukocytes or in the number of macrophages and lymphocytes infiltrating inflamed tissues. Another may be the decrease in immune cells expressing the LPS-receptor toll like receptor 4 (TLR-4). The methods can thus also be considered methods of affecting or altering the immune response of a subject to whom the ABA therapy is administered. The subject may have any condition in which a downregulation of LPS-induced inflammation is deemed beneficial by someone skilled in the art. For the treatment or prevention of LPS-induced inflammation, it is preferred that ABA be administered at amounts of about 0.05 to about 1,000 mg ABA per kg of body weight daily, more preferably about 0.5 to about 500 mg of ABA per kg of body weight daily.

In another embodiment, the present invention provides methods for treating or preventing pulmonary inflammation. Such disorder can be caused by a respiratory pathogen, such as influenza virus, rhinovirus, respiratory syncytial virus, parainfluenza, *Staphylococcus aureus, Streptococcus pneumoniae, Francisella tularensis, Mycobacterium tuberculosis* and *Bacillus anthracis*. In this embodiment, the ADA therapy is administered in a amount effective to decrease mucosal and submucosal inflammatory cell infiltration, perivascular cuffing, terminal airway infiltration, or epithelial necrosis in the lung. For the treatment or prevention of pulmonary inflammation, it is preferred that ABA be administered at amounts of about 0.05 to about 1,000 mg ABA per kg of body weight daily, more preferably about 0.5 to about 500 mg of ABA per kg of body weight daily.

In yet another embodiment, the present invention provides methods and compositions for enhancing vaccine effectiveness in a mammal. This embodiment involves administering ABA along with the vaccine. The ABA can be co-administered with the vaccine or be administered within one day, preferably within an hour of the vaccination. The routes administration of the ABA and the vaccine may be the same or different. For example, both the vaccine and the ABA may be administered orally. Alternatively, the ABA may be administered orally, while the vaccine is administered subcutaneously. The ABA is preferably administered, along with the vaccine, in a dose of about 0.05 to about 1,000 mg ABA per kg of body weight, more preferably about 0.5 to about 500 mg ABA per kg of body weight.

In certain instances, the ABA can be used as an adjuvant in the vaccine. In that case, the ABA is formulated as part of the vaccine composition. That composition includes the vaccine and ABA. Other excipients well-known in the art can also be included in the composition. The vaccine can contain, but is not limited to, antigens of influenza virus, rhinovirus, respiratory syncytial virus, parainfluenza, *Staphylococcus aureus, Streptococcus pneumoniae, Francisella tularensis, Mycobacterium tuberculosis*, or *Bacillus anthracis*.

In view of the above methods, it should be evident that the present invention provides ABA therapy for use in contacting cells, such as in treating cells of a subject. The above discussion focuses on the use of ABA as part of a composition for use in what could generally be considered a pharmaceutical or medical setting.

As should be evident, the ABA therapy may be provided in a pharmaceutically acceptable form. ABA may also be combined with other pharmaceuticals to provide enhanced treatment to those suffering from or susceptible to LPS-induced inflammation and its harmful effects. Such therapy can be provided in a form that is suitable for administration to a subject in need. In this form of therapy ABA may be provided as a purified or semi-purified substance, or as a part of a simple or complex composition. Where present as part of a composition, the composition as a whole should be biologically tolerable at the amount to be exposed to a living cell. The pharmaceutical composition may comprise any number of substances in addition to ABA, such as, but not limited to, water, salts, sugars, buffers, biologically active compounds, drugs.

Without further description, it is believed that one of ordinary skill in the art can, using the preceding description and the following illustrative examples, make and use the present invention. The following examples are given to illustrate the present invention. It should be understood that the invention is not to be limited to the specific conditions or details described in this examples. In the examples and throughout this specification, all percentages, part and ratios are by weight unless indicated otherwise.

Example 1

Effect of Abscisic Acid on LPS-Induced Inflammation and Mechanism of Action

Research Design and Methods

PPAR γ Ligand-Binding Assay—The ability of ABA to bind to the ligand-binding domain of PPAR γ was assessed experimentally using the Polarscreen PPAR Competitor Assay, Green (Invitrogen, Carlsbad, Calif.) following manufacturers instructions. Briefly, concentrations of (+) ABA (Sigma), (−) ABA (Sigma), and rosiglitazone (Cayman Chemical) ranging from 0.001 μM-10 μM were added to wells containing the ligand-binding domain of PPAR γ bound to a fluorescent-marker. After 4 hours the ability of each compound to displace the fluorescent ligand, and therefore reduce the polarization values, was assessed using a fluorescent plate reader with 485 nm excitation and 535 nm emission. Results are a compilation of 4 independent experiments.

Reporter Activity Assays—To determine PPAR γ activity, pCMX.PPAR γ expression plasmid and a pTK.PPRE3x luciferase reporter plasmid driven by the PPRE-containing Acyl-CoA oxidase promoter were purified using Qiagen's Maxi kit (Valencia, Calif.). RAW 264.7 macrophages were cultured with DMEM (Mediatech, Manassas, Va.) containing 10% fetal bovine serum (FBS) and grown until 60-70% confluence. Cells were co-transfected in each well with 0.6-μg plasmid DNA and 10 ng of pRL reporter control using F-2 transfection reagents (Targeting Systems, Santee, Calif.) according to the manufacturer's protocol. After 24 hours, transfected cells were seeded into white, opaque 96-well plates (BD) at a concentration of 25,000 cells/well. To determine NF-κB reporter activity, cells were then transfected with 0.2-μg pNF-kB reporter and 0.2 μg pRL reporter control using the Lipofectamine 2000 transfection reagent (Invitrogen). Transfected cells were then treated in replicates of 8 with rosiglitazone (Ros 1 μM; Cayman Chemicals, Ann Arbor, Mich.), (+) ABA (1.25, 2.5, 5, 10 μM, Sigma Aldrich, St. Louis, Mo.), (−) ABA (1.25, 2.5, 5, 10 μM, Sigma), or vehicle (DMSO) and placed in a 37° C. incubator with 5% $CO_2$. After 20 hours cells were harvested in reporter lysis reagent. Luciferase activity, normalized to pRL activity in the cell extracts, was determined by using the Dual Luciferase II reporter assay system (Promega, Madison, Wis.) using a Modulus 96-well luminometer (Turner Biosystems, Sunnyvale, Calif.). All values were normalized to control wells to calculate relative luciferase activity.

LANCL2 siRNA and PPAR γ co-transfections—RAW macrophages were transfected with the PPAR γ plasmid as described in the preceding section with or without LANCL2 siRNA. Specifically, RAW macrophages were then co-transfected with 0.2-μg plasmid DNA and 0.25 μL LANCL2 siRNA (20 μM) per well using the Lipofectamine 2000 transfection reagent (Invitrogen). After 48 hr incubation at 37° C., RAW macrophages were then treated in replicates of 8 with ABA (1.25, 2.5, 5, or 10 μM), Ros (1 or 10 μM), or DMSO control and incubated for 24 hr at 37° C. After incubation, RAW macrophages were harvested in reporter lysis reagent and luciferase activity was determined as described above. LANCL2 mRNA was measured by RT-PCR in control wells to assess the efficiency of knockdown.

Bone Marrow-derived Macrophage (BMM) Cultures—Bone marrow cells from PPAR γ flfl; MMTV-Cre− (flfl-Cre−) and flfl-Cre+ mice were cultured in DMEM with M-CSF (50 ng/ml) for 7 days. Fresh media with M-CSF was added on day 3. FACS analysis of BMM harvested at day 7 showed that under these conditions ≥90% of cells were CD11b+ F4/80+, corresponding to a macrophage phenotype. Following differentiation macrophages were directly stimulated with LPS (100 ng/ml) as previously described for 12 hours (21). ABA was added to macrophage cultures at a concentration of 2.5 μM. The effect of ABA on LPS/toll-like receptor-4 (TLR4)-mediated prostaglandin E2 (PGE2), leukotriene B4 (LTB4) and monocyte chemoattractant protein-1 (MCP-1) production by macrophages was examined in cell supernatants 12 hours following the LPS challenge by using a commercial PGE2 EIA kit (Cayman Chemicals), a LTB4 competitive binding assay (R&D Systems) and a MCP-1 ELISA (R&D Systems), respectively, per the manufacturer's instructions.

Mice and in vivo Treatments—PPAR γ flfl; MMTV Cre+ (flfl-Cre+) conditional knockout mice, lacking functional PPAR γ in all hematopoietic cells; and their flfl-Cre− control littermates in a C57BL/6 background were generated by using the Cre-lox recombination system as previously described (13, 22). Mice were fed control, ABA (100 mg/kg of diet; corresponding to an effective oral dose of 0.2 mg ABA/mouse/day), or pioglitazone (70 mg/kg diet; 0.14 mg pioglitazone/mouse/day)-supplemented diets for 36 days and then were challenged with *Escherichia coli* lipopolysaccharide (LPS) at 375 μg/kg in 0.1 ml of sterile saline solution intraperitoneally (i.p.) to induce systemic inflammation. All experimental procedures were approved by the Institutional Animal Care and Use Committee of Virginia Polytechnic Institute and State University and met or exceeded requirements of the Public Health Service/National Institutes of Health and the Animal Welfare Act as amended.

Intracellular cAMP in CD3/CD28-stimulated splenocytes and LPS-stimulated macrophages—Spleens were excised from C57BL6/J mice under sterile conditions. Cells were released by disrupting the tissue between frosted glass slides and red blood cells were lysed with erythrocyte lysis buffer. Splenocytes were enumerated with a Coulter Counter (Beckman Coulter, Fullerton, Calif.) and seeded in cRPMI at $1 \times 10^6$/ml onto 24-well plates pre-coated with anti-mouse CD3 (5 μg/mL; BD Pharmingen) and anti-mouse CD28 (1 μg/mL; BD Pharmingen). After 20 hours incubation in a 37° C. incubator with 5% $CO_2$, cells were adapted to Hank's buffered salt solution buffer for 30 min and then stimulated with ABA (0, 0.01, 1, 10 μM) for 10 min. RAW 264.7 macrophages and BMM obtained as described above were adapted to DMEM without FBS for 12 hours and then stimulated with ABA (1.25, 2.5, 5, 10 μM) for 10 min. For intracellular assessment of cAMP, cells were harvested into 0.1 M HCl and the lysates were collected. The cAMP concentration of the lysates was determined using an EIA kit (Assay Designs, Ann Arbor, Mich.).

Flow Cytometry—Mesenteric lymph nodes (MLN) and spleen-derived cells ($2 \times 10^5$ cells/well) or whole blood (10 µL/well) were seeded onto 96-well plates, centrifuged at 4° C. at 3000 rpm for 4 minutes, and washed with PBS containing 5% fetal bovine serum and 0.09% sodium azide (FACS buffer). To assess differential monocyte/macrophage subsets, the cells were incubated in the dark at 4° C. for 20 minutes in FcBlock (20 µg/ml; BD Pharmingen), and then for an additional 20 minutes with fluorochrome-conjugated primary antibodies anti-F4/80-PE-Cy5 (5 µg/mL, eBioscience) and anti-CD 11b-Alexa Fluor 700 (2 µg/mL, eBioscience), and anti-TLR-4-PE-Cy7 (2 µg/mL, eBioscience). For lymphocyte assessment, cells were incubated with anti-CD4-FITC (2 µg/mL; BD Pharmingen), anti-CD8-PerCp-Cy5.5 (2 µg/mL, eBioscience), CD3 PE-Cy5 (2 µg/mL; BD Pharmingen), anti-TLR-4 PE-Cy7, and anti-IL17A-PE (2 µg/mL, eBioscience) as previously shown (23). Flow results were computed with a BD LSR II flow cytometer and data analyses was performed with FACS Diva software (BD).

Microarray data analysis—After homogenization of spleens, total RNA was extracted and purified using the RNAeasy system according to manufacturer's instructions (Qiagen Valencia, Calif.). The QIAGEN RNase-free DNase supplement kit was used to ensure that the RNA was free from DNA contamination. RNA was then processed and labeled according to the standard target labeling protocols and the samples were hybridized, stained, and scanned per standard Affymetrix protocols at VBI core laboratory on Mouse 430 2.0 expression arrays (Affymetrix Inc., Santa Clara, Calif.). All statistical analysis of the data was performed within the R statistical environment—Version 2.9.0 (24) using Bioconductor packages (25)]. Raw microarray data from CEL files were read with 'affy' package (26) and pre-processed by gcRMA algorithm (GC Robust Multiarray Average) that performs the three steps: (i) adjustment of the gene expression signal against the background caused by optical noise and non-specific binding, (ii) robust multi-array normalization (27), and (iii) summarization of the probes belonging to each probe set. Empirical Bayes adjustment was applied and p-values were corrected for multiple testing. Genes associated with p-value<0.1 were considered significantly modulated by LPS. The selected list of genes was analysed with hypergeometric testing that applies Fisher's exact test to find association between interesting genes and membership within the KEGG pathway(s).

The microarray data (both raw and normalized) have been submitted to the Gene Expression Omnibus. (GEO, http://www.ncbi.nlm.nih.gov/geo/, Data set: GSE21013). The experiment followed a 2×2 factorial design with 2 factors: LPS and ABA, each with 2 levels: absence and presence. Thus there were four groups of mice: LPS & ABA, LPS & control, no LPS & control, no LPS & ABA. The design matrix, constructed in the package 'limma', defined coefficients for LPS main effect, ABA main effect and the interaction effect. Linear modeling discovered 43 probe sets (genes) corresponding to LPS-ABA interaction. These 43 probe sets were uploaded to IPA8.0 for Ingenuity Pathway Analysis (Ingenuity Systems, Redwood City, Calif.).

Real-time qRT-PCR gene expression analyses—Total RNA (1 µg) from spleens was used to generate a complementary DNA (cDNA) template using the iScript cDNA Synthesis Kit (Bio-Rad, Hercules, Calif.) using previously described conditions (13). Each gene amplicon was purified with the MiniElute PCR Purification Kit (Qiagen) and quantitated on an agarose gel by using a DNA mass ladder (Promega). These purified amplicons were used to optimize real-time PCR conditions and to generate standard curves in the real-time PCR assay. Primer concentrations and annealing temperatures were optimized for the iCycler iQ system (Bio-Rad) for each set of primers using the system's gradient protocol. PCR efficiencies were maintained between 92 and 105% and correlation coefficients above 0.98 for each primer set during optimization and also during the real-time PCR of sample DNA. Complementary DNA (cDNA) concentrations for genes of interest were examined by real-time quantitative PCR using an iCycler IQ System by using a previously published protocol (13).

NF-κB and NFAT activities—Spleens were diced into smaller pieces in lysis buffer containing dithiothreitol and a protease inhibitor cocktail and then further disrupted using a dounce ground glass homogenizer at 4° C. Nuclear extraction for tissue homogenate and BMM was performed using the Nuclear Extract kit (Active Motif, Carlsbad, Calif.) per the manufacturer's instructions. The extracts were used to perform a Bradford-based assay for quantifying the protein concentrations and stored at −80° C. NF-κB and NFATc1 activities were measured as previously described (13) by using the Trans-AM™ NF-κB p65 and the Trans-AM™ NFATc1 ELISA-based assays (Active Motif), respectively per the manufacturer's instructions.

Statistical Analysis—Parametric data were analyzed by using the analysis of variance (ANOVA) followed by Scheffe's multiple comparison method. Nonparametric data were analyzed by using the Mann-Whitney's U test followed by a Dunn's multiple comparisons test. ANOVA was performed by using the general linear model procedure of SAS (SAS Institute Inc., Cary, N.C.) (28). Statistical significance was assessed at a probability (P) value≤0.05.

Results and Discussion

Figure 1A:
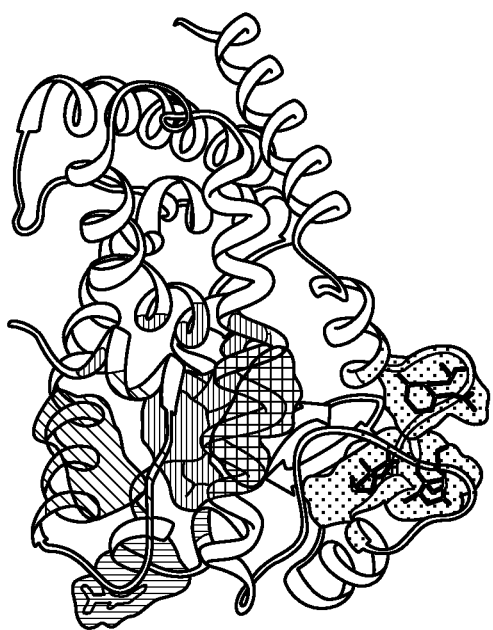
FIG. 1 (A) illustrates a ribbon representation of PPARγ with backbone segments colored to represent predicted binding sites for ABA. Docked poses of ABA are shown with coloring to match the region to which ABA docked. The orange backbone segments and ABA structures indicate the location for a majority (92.64%) of the 2161 poses with the most negative free energy of binding. This region was designated site S1. The green, blue, and yellow sites indicate surfaces where ABA docked favorably as well, but with less negative free energy of binding. The red backbone sections and ABA structures indicate the activation site for full agonism (S2), where a small number of ABA poses were predicted with less negative free energy of binding values compared to those for S1. (B) Ribbon representation of the homology model of human lanthionine synthetase C-like component 2 (LANCL2). Docked poses of ABA are shown with carbons colored to match the region to which ABA docked. The red backbone segments and ABA structures indicate the binding site with the most poses of ABA (58%). Images generated using UCSF Chimera (19).

In silico docking of ABA to PPAR γ and LANCL2. To determine whether ABA is a functional ligand of PPAR γ we first used an in silico approach to dock ABA to the PPAR γ LBD (FIG. 1A). Several groups have predicted the rear portion of the binding cavity proximal to helix H12 to be the site where ligand binding would induce activation of PPAR γ (29-31). The docking results showed that this site (S2) is not favored by ABA when the entirety of the binding cavity is evaluated for binding interactions. Instead, ABA energetically favored a mostly hydrophobic cleft near the opening of the binding cavity (S1) for all docking methods used where the grid boxes included this region. The predicted free energy of binding values ranged from −9.4 to −9.0 kcal/mol for poses in S1 (92.64% of 2161 poses) and −7.0 to −6.2 kcal/mol for poses in S2 (4.53% of 2161 poses). Given these predicted energies, it seems unlikely that it would be energetically favorable for ABA to diffuse past the more favorable opening surface through the binding cavity to the activation site at the rear of the cavity in order for PPAR γ activation to occur.

Figure 2A:
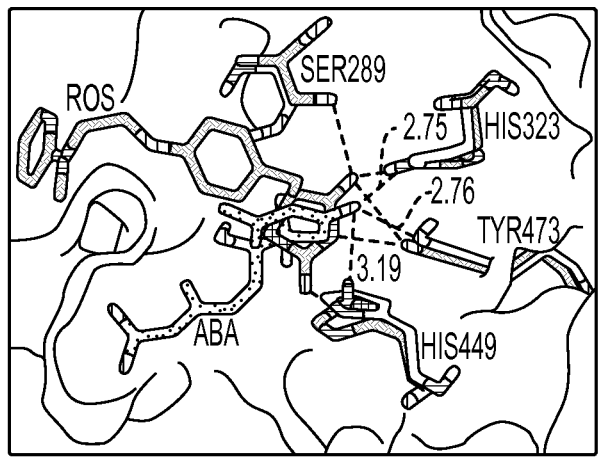
FIG. 2 illustrates a representative binding pose of the most favorable docked orientations of ABA with PPARγ and LANCL2 shown in molecular surface models. Hydrogen bonds are shown as dashed green lines. Values for distances (in Angstroms) between ABA and key residues are shown in magenta. Oxygen atoms are colored in red, nitrogen atoms in blue, and hydrogen atoms in white. (A) Comparison of distance measurements between ligands and four key residues involved in hydrogen-bonding interactions proposed to induce PPARγ activation. PPARγ key residues and co-crystallized rosiglitazone (PDB ID 1FM6 (20)) are shown in orange, key residues of the model PPARγ protein are shown in gray, and ABA is shown in magenta. The number of potential hydrogen bond interactions for rosiglitazone was five, whereas only three were predicted with ABA. (B) ABA is illustrated by a magenta stick model, and selected residues of LANCL2 are depicted by gray stick models. Amino acid residues surrounding ABA are labeled. Images generated using UCSF Chimera (19).

If ABA docking is tightly restricted to the region of the binding site expected for full agonism, the majority of returned poses show the hydrogen-bonding residues in the receptor site interacting with the ring-structure head group rather than the carboxylate group, as typically observed with full agonists. Although the head group contains a single carbonyl group that could serve as a hydrogen-bond acceptor and hydrogen bonding interactions are observed in the binding site in the docked complex, (FIG. 2A) experiments suggest that these interactions may not be sufficient to cause activation of the receptor. The carboxylate must be oriented towards the critical amino acid residues for activation to occur.

Figure 1B:
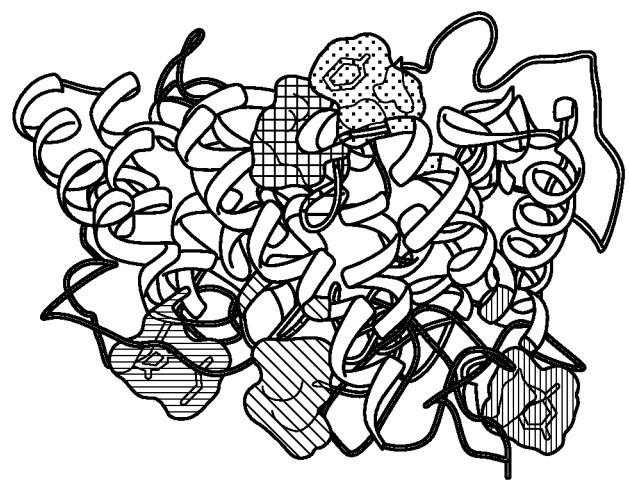
Figure 2B:
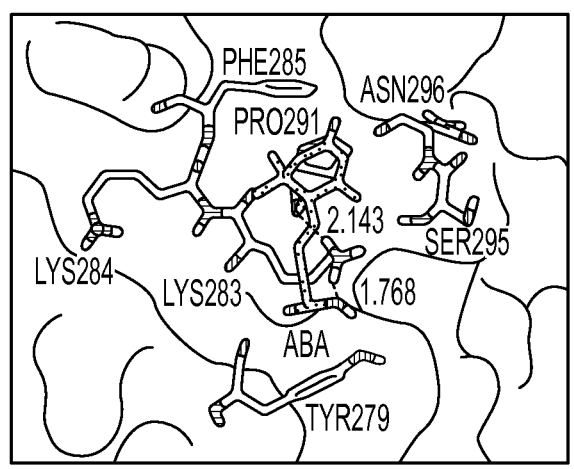

Since ABA did not appear to bind to the activation site of PPAR γ and given its purported signaling via LANCL2 in human granulocytes (32), we next examined the ability of ABA to bind to LANCL2. Data and details for this examination were previously published (51). Examination of the distribution ibution of the binding sites on LANCL2 implied that ABA showed preferential binding to the loop regions of LANCL2. The red region on the LANCL2 with the highest population of clusters was considered as the potential binding site for ABA (FIG. 1B). FIG. 2B shows a docked pose for ABA a pocket in LANCL2 after the binding site restricted grid area search. Two hydrogen bonds formed between the nitrogen atom in the side chain of LYS283 and two oxygen atoms of ABA that positioned AICA deep in the pocket and increased the affinity of ABA for LANCL2, although we do not know whether ABA binding induces a conformational change in LANCL2.

Figure 3A:
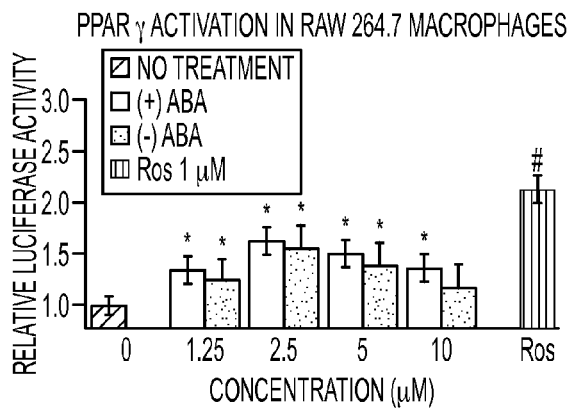
FIG. 3 illustrates the in vitro effects of abscisic acid (ABA) isomers. For transient transfections (A), RAW 264.7 macrophages were transfected as described in the Materials and Methods before being exposed to increasing concentrations (1.25, 2.5, 5, or 10 μM) of (+) or (−) ABA, DMSO alone (no treatment), or rosiglitazone (1 μM). After 20 hours, the relative luciferase activity was assessed for each treatment. To assess the ability of the ABA isomers to bind PPAR γ (B), concentrations of (+) ABA, (−) ABA, or rosiglitazone ranging from 0.001-10 pM were assessed for their ability to displace a fluorescent ligand bound to the PPAR γ ligand binding domain. Results are a compilation of 4 independent experiments. The ability of ABA to increase intracellular cAMP concentrations (C), lantionine synthetase C-like 2 (LANCL2) (D) and PPAR γ (E) in CD3/CD28-stimulated splenocytes was assessed. The effect of ABA on cAMP concentrations in macrophages was determined (F). Data are presented as mean±standard error of three independent experiments. Data points with an asterisk (P<0.05) or a number sign (P<0.0001) are significantly different.

ABA isomer-specific effects on transactivation of PPAR γ and cAMP accumulation. We next examined the effect of ABA on PPAR γ in vitro. We have previously demonstrated that a racemic mixture of ABA isomers activates PPAR γ in 3T3-L1 preadipocytes (4). Here, we assessed the affect of the individual (+) and (−) ABA isomers on PPAR γ activation using the RAW 264.7 macrophage cell line (FIG. 3A). Both the (+) and (−) ABA isomers activated PPAR γ to a similar degree, inducing a maximal effect at 2.5 µM.

Figure 3B:
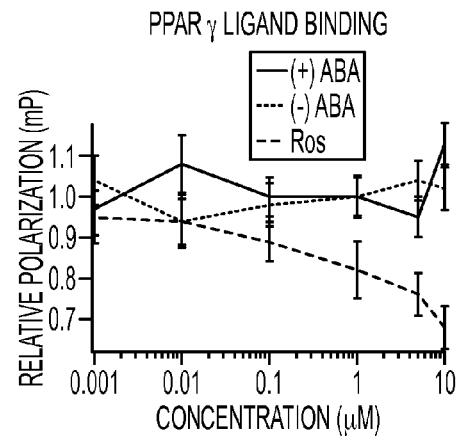

To confirm our in silico findings indicating that ABA is not a ligand of PPAR γ, we next compared the ability of each ABA isomer and the synthetic PPAR γ ligand rosiglitazone (Ros) to compete for binding to the PPAR γ LBD (FIG. 3B). Increasing the concentrations of ABA from 0.001-10 µM showed no ability of either ABA isomer to compete with the tracer for binding to the PPAR γ LBD, whereas Ros successfully competed for binding to the LBD and displaced the tracer. These findings indicate that ABA is not a PPAR γ ligand despite its ability to increase PPAR γ activity.

Figure 3C:
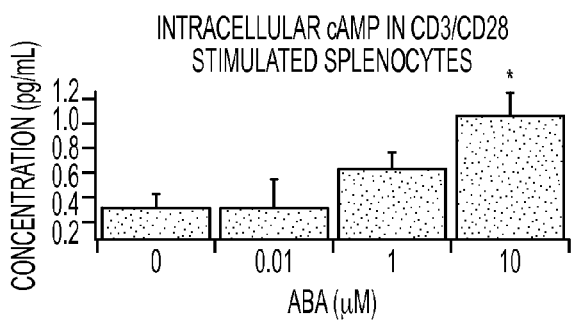
Figure 3D:
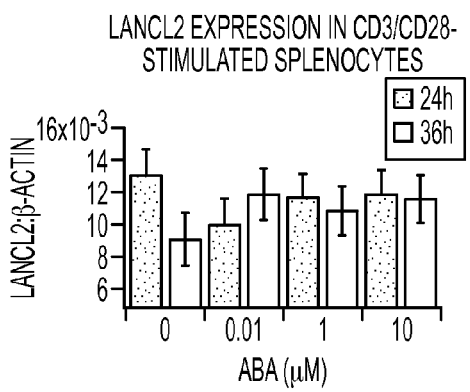
Figure 3E:
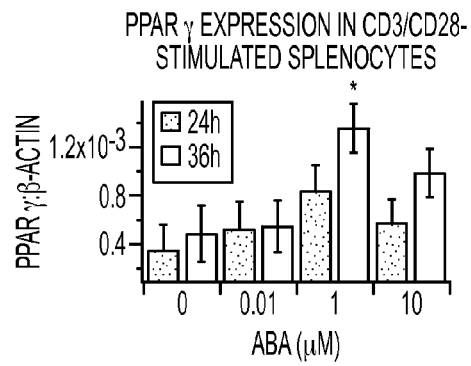
Figure 3F:
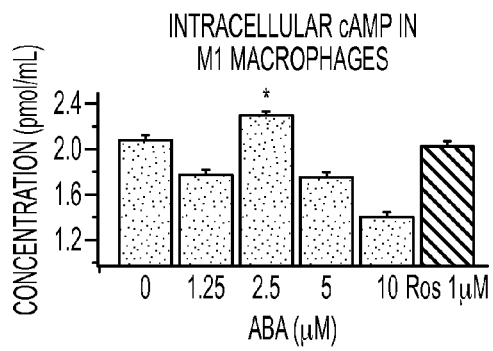

There have been recent reports indicating that ABA increases intracellular levels of cAMP (33, 34). Here, we show that splenocytes stimulated with CD3/CD28 show significantly increased intracellular cAMP when treated with ABA at 10 µM (FIG. 3C) without affecting phosphodiesterase activity (data not shown). The increased accumulation of intracellular cAMP was associated with upregulation of PPAR γ and its reporter activity but not LANCL2 mRNA expression (FIGS. 3D & E). We also demonstrate that treatment of macrophages for 10 minutes with ABA induces a cAMP peak (10% over control) at 2.5 µM, thereby coinciding with the peak of maximal ABA-mediated PPAR γ activation. When compared to splenocytes, M1 macrophages exhibited a more narrow concentration range and relative insensitivity to ABA treatment in relation to cAMP generation (FIG. 3F).

Figure 4A:
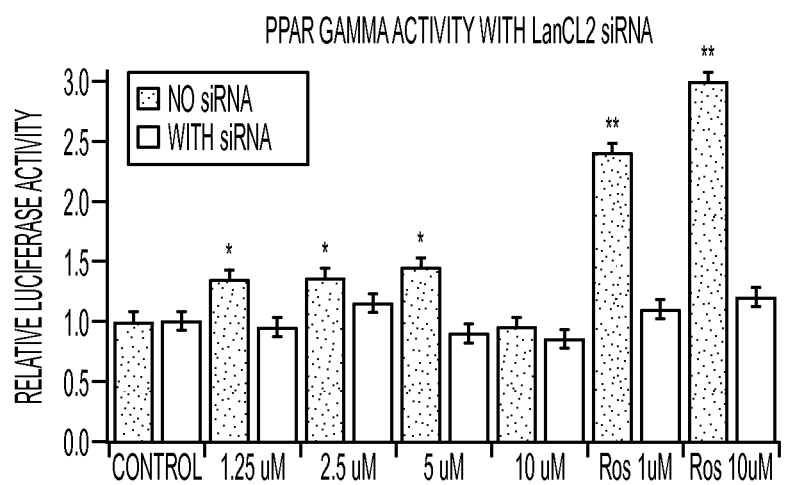
FIG. 4 illustrates the effect of lanthionine synthetase C-like 2 (LANCL2) disruption on PPAR y activation. Panel A illustrates the effect of abscisic acid (ABA; 1.25, 2.5, 5, or 10 μM) and rosiglitazone (Ros; 1 and 10 μM) on PPAR γ reporter activity in RAW 264.7 macrophages expressing normal levels of LANCL2 or following a knockdown of LANCL2 using siRNA. Panel B illustrates the effect of siRNA on LANCL2 mRNA expression. The efficiency of LANCL2 knockdown was calculated by real time quantitative RT-PCR to be 80%. Data are presented as mean±standard error of three independent experiments. Data points with an asterisk are significantly different from control (P<0.05).
Figure 4B:
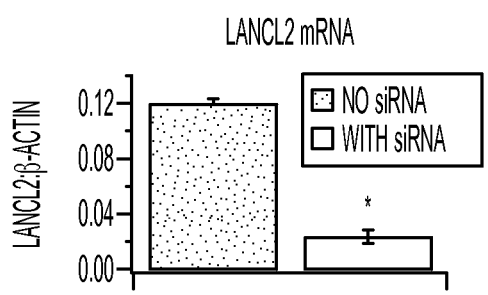

Knockdown of LANCL2 disrupts PPAR γ activation. To measure the affect of LANCL2 knockdown on ABA- and Ros-induced PPAR γ activation, cells were first transfected with a PPAR γ expression and luciferase plasmids and treated with either racemic ABA or Ros (1 or 10 µM). As anticipated, ABA and Ros significantly elevated PPAR γ compared to untreated cells (FIG. 4A). In the same project we assessed whether introduction of LANCL2 siRNA affects ABA or Ros-induced PPAR γ activation. Our data indicate that the addition of LANCL2 siRNA significantly disrupted PPAR γ activation (FIG. 4A), as neither ABA nor Ros significantly affected PPAR γ activity. The disruption of LANCL2 was 80% by qRT-PCR (FIG. 4B).

Figure 5A:
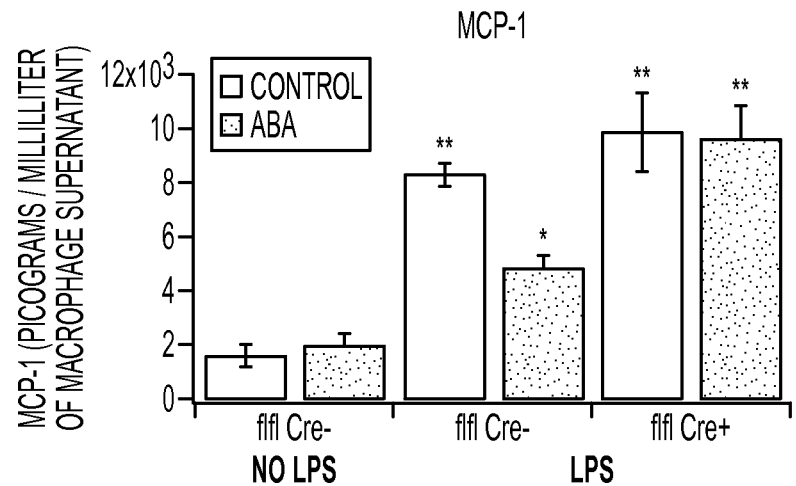
FIG. 5 illustrates that abscisic acid (ABA) treatment downregulates the production of (A) monocyte chemoattractant protein-1 (MCP-1) and (B) prostaglandin E2 (PGE2) in bone marrow-derived macrophages recovered from PPAR γ-expressing (flfl-Cre−) and conditional PPAR γ null (flfl-Cre+) mice and stimulated with lipopolysaccharide (LPS). Cell supernatants from macrophages treated with ABA (2.5 μM) or vehicle alone were collected at 12 hours following LPS stimulation (* vs **, P<0.05). Results are presented as means±SEM (n=5).
Figure 5B:
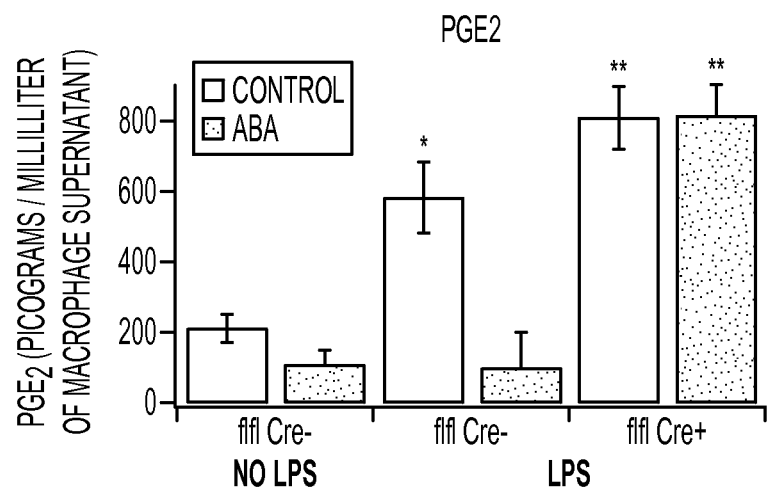
Figure 6A:
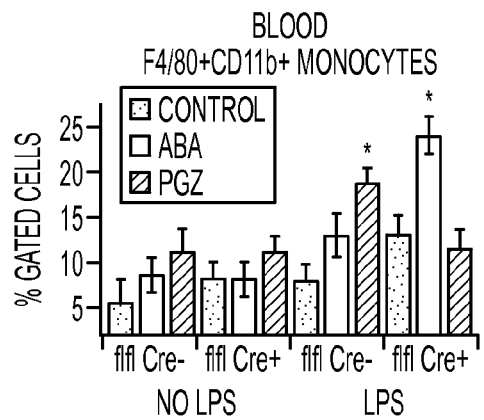
FIG. 6 illustrates the effect of abscisic acid (ABA) on toll-like receptor 4 (TLR-4) expression in blood and mesenteric lymph node (MLN)-derived immune cells in mice challenged with lipopolysaccharide (LPS). PPAR γ flfl; Cre− (flfl- Cre−) and PPAR γ flfl; MMTV Cre+ mice (flfl-Cre+), which lack PPAR γ in hematopoietic cells, were fed a control diet or diets supplemented with ABA or pioglitazone (PGZ). Mice were injected with LPS (375 µg/kg) and euthanized after 6 hrs. Flow cytometry was performed on cells derived from blood and MLN to assess immune cell subsets affected by diet. Data are presented as mean±standard error. Data points with an asterisk indicate a significant difference from the respective control diet (P<0.05). Results are presented as means±SEM of groups of 10 mice.
Figure 6B:
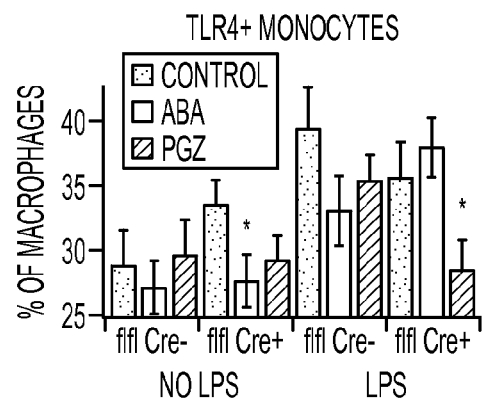
Figure 6C:
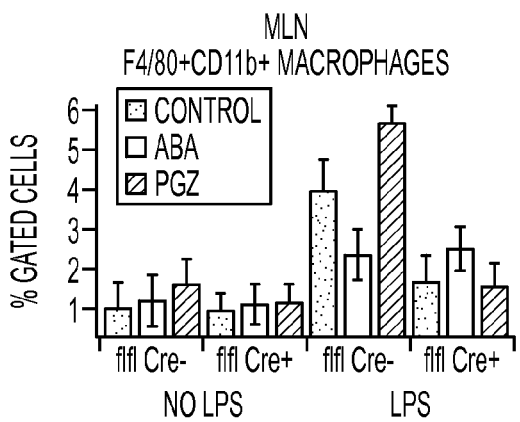
Figure 6D:
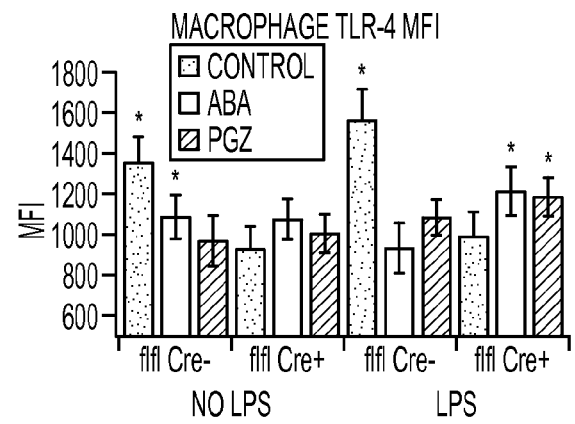
Figure 6E:
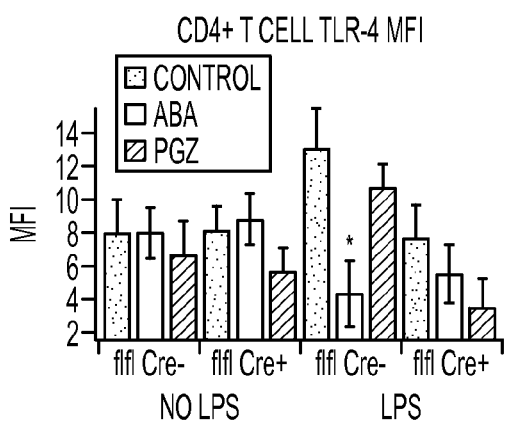
Figure 6F:
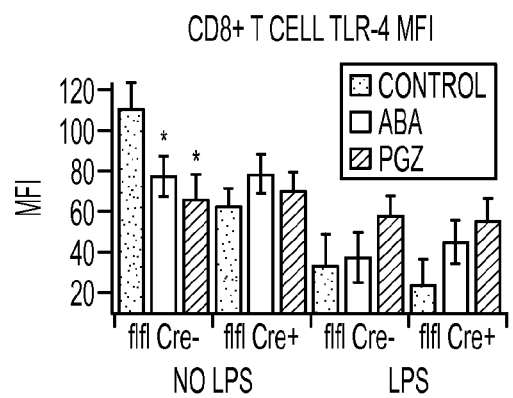

ABA suppresses the generation of inflammatory mediators by LPS-stimulated macrophages. The macrophage is one of the cell types whose functions can be significantly regulated by PPAR γ agonists (10, 35). Because our findings indicated that PPAR γ agonism by ABA occurred without direct binding to the receptor, we next evaluated whether in vitro treatment of BMM mimicked the effects induced by other agonists, like the TZDs. We specifically measured if ABA could down-regulate the expression of pro-inflammatory mediators. We found that ABA significantly suppressed the ability of BMM to secrete monocyte chemoattractant protein 1 (MCP-1) and prostaglandin $E_2$ ($PGE_2$) in response to in vitro LPS stimulation as detected by ELISA and EIA, respectively, in cell culture supernatants (FIGS. 5A & B).

Effect of ABA on Immune Cell Subsets Following an LPS challenge. To assess whether ABA suppressed systemic inflammation we administered control, ABA or pioglitazone (PGZ)-supplemented diets for 36 days to immune cell-specific PPAR γ null mice or floxed littermates. Based on feed intake and dose in the diet, we estimate that mice were ingesting 0.2 mg of ABA or 0.14 mg PGZ on a daily basis, which can be considered prophylactic doses. The concentration of ABA and PGZ were chosen based on previously published ABA and TZD studies (2, 4). At the end of the treatment period mice were challenged intraperitoneally with LPS and the systemic inflammatory response was assessed at 6 hours post-challenge. We examined immune cell subsets in peripheral blood, MLN, and spleen. ABA significantly increased the percentages of blood monocytes (defined as F4/80+CD11b+) in LPS-treated immune cell-specific PPAR γ null mice, though not in PPAR γ-expressing mice. In the MLN, both ABA and PGZ supplementation significantly suppressed the expression of TLR4 in F4/80+CD11b+ macrophages, an effect that could limit the extent of LPS-induced inflammation. In mice treated with LPS, ABA reduced TLR4 expression levels by macrophages in PPAR γ-expressing but not in immune cell-specific PPAR γ null mice suggesting either a PPAR γ dependency of this effect or indicating that PPAR γ is required for TLR4 expression, regardless of drug treatment. Both ABA and PGZ also significantly reduced the TLR4 expression in CD8+ T cells of non-LPS treated mice (FIG. 6).

Figure 11A:
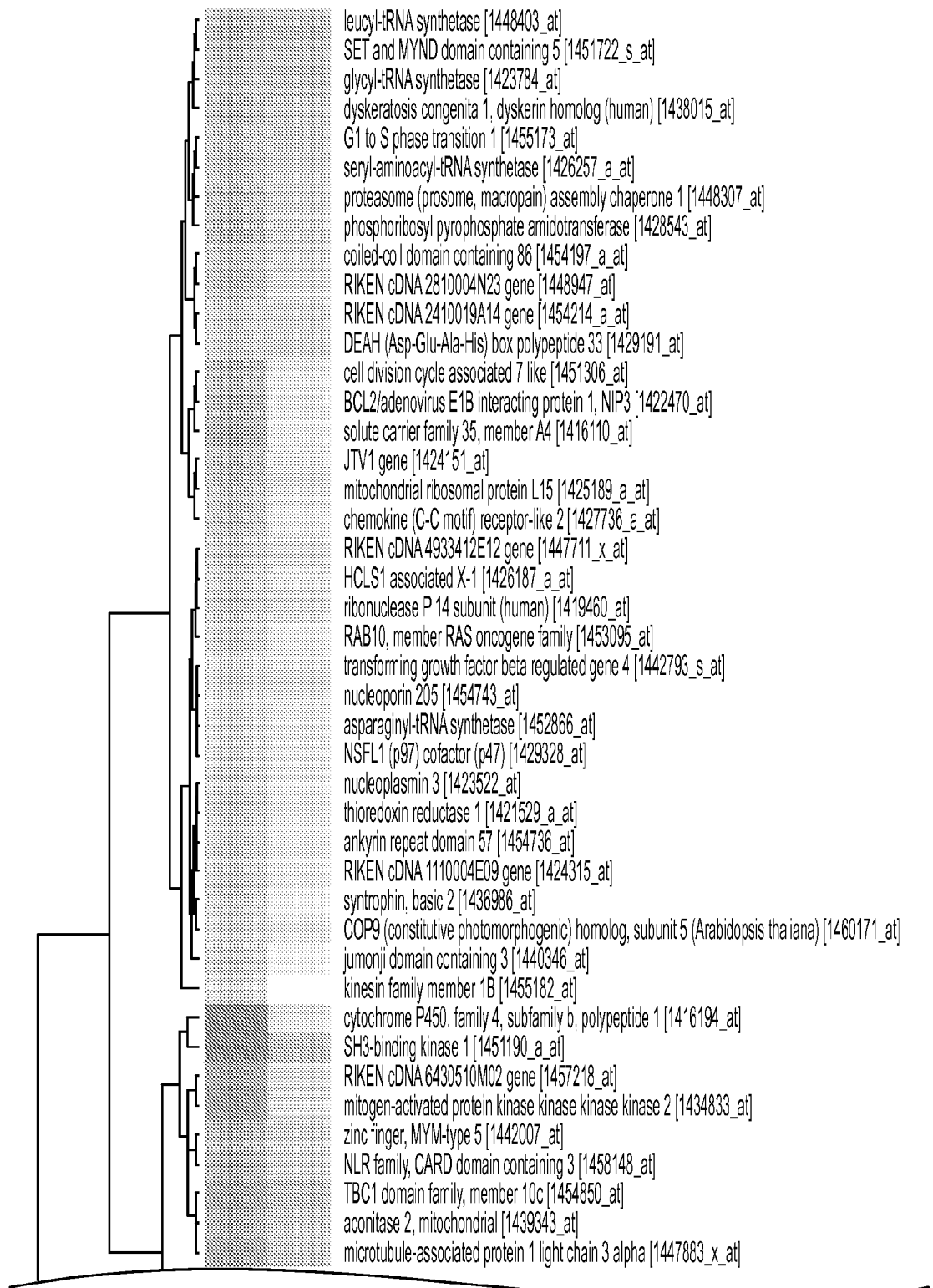
FIG. 11 is a heat map showing the effect of ABA on LPS-induced gene expression changes. The two columns represent fold-change in gene expression induced by challenging mice with lipopolysaccharide (LPS) compared to untreated (No LPS challenge). Red color represents up-regulation (positive log-fold change) while green represents down-regulation (negative log-fold change). Hierarchical clustering has been applied on the genes that display three categories of genes according to degree and direction of fold change in transcriptional alteration caused by LPS: up-regulated (top), down-regulated (middle) and highly up-regulated (bottom).
Figure 11B:
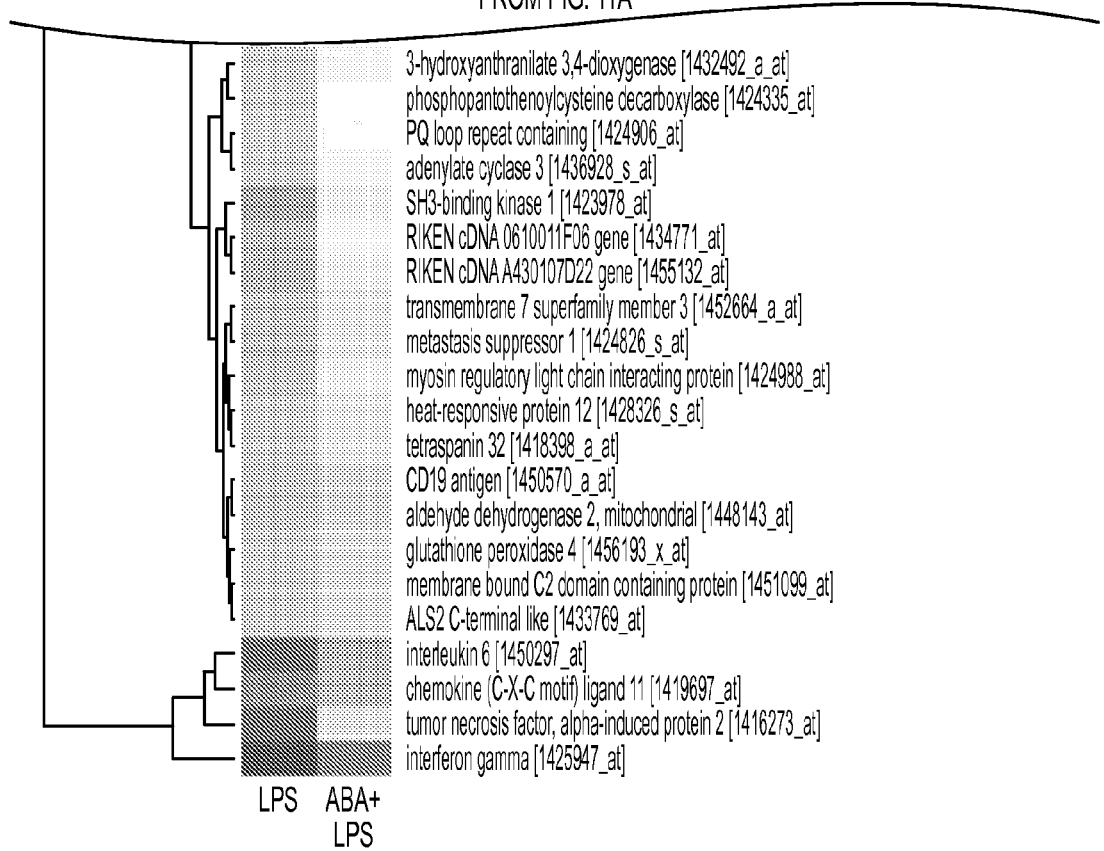
Figure 12A:
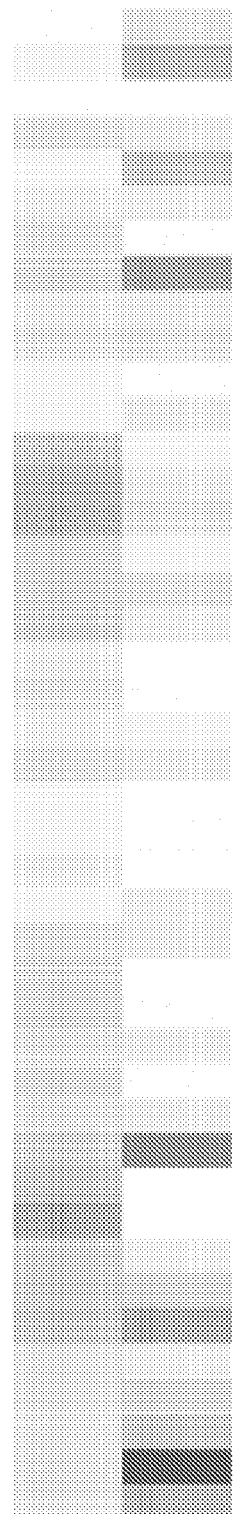
FIG. 12 is a heat map showing the effect of ABA on LPS-induced gene expression changes in wild-type and conditionally PPARγ-null mice. The two columns represent the effect of ABA in wild-type (ABAeffect.WT) and conditionally PPARγ-null (ABAeffect.KO) mice. The genes were selected on the basis of those that responded to LPS challenge but were down-modulated by ABA. The ordering of the genes (rows) is same as in FIG. 7. Color of each cell represents the ratio of ABA-induced fold-change compared to fold-change in mice on diet without ABA. Red represents up-regulation by ABA, green represents down-regulation. ABA causes down-regulation of IL-6 and IFN-γ, but this effect is lessened (IFN-γ) or reversed (IL-6) when PPARγ is deleted in immune cells. For most of the other genes, ABA effect is substantially altered in the absence of PPARγ.
Figure 12B:
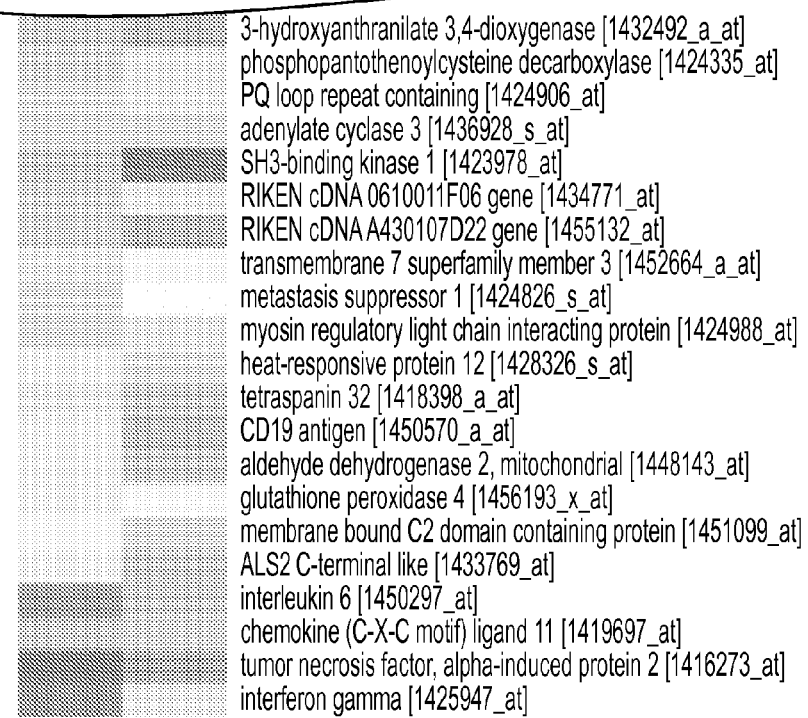

Microarray analysis of ABA's effect on LPS-mediated inflammation in the spleen. Immune cell-specific PPAR γ null mice or floxed littermates were fed control or ABA-supplemented diets and then i.p. challenged with LPS (375 µg/kg). Global transcriptomic and network analyses were performed in spleen samples collected 6 hours post LPS challenge. Under the P-value threshold of 0.1, more than 2000 genes were modulated by LPS in both data sets. Out of these, 130 were discovered to be consistently modulated by LPS, but unchanged in expression when diet was supplemented with ABA. Filtering on the fold-change (at least 2-fold induction by LPS) extracted 64 genes that were either up- or down-regulated by LPS, but this transcriptional effect was lessened in the presence of ABA in diet (FIG. 11). After applying hierarchical clustering on these genes, a heat map was generated. Regardless of the direction (up- or down-) of modulation, the magnitude of gene expression (fold-change) was attenuated by ABA (as seen in lighter color on the right column of FIG. 11). Four genes that emphatically responded to LPS challenge (i.e., IL-6, IFN-γ, TNF-α induced protein 2 and chemokine ligand 11), were down-regulated by ABA. Fold induction caused by ABA (ABA effect) was calculated for both PPAR γ-expressing and immune cell-specific PPARγ-null mice (FIG. 12). The ABA effect is impaired (or abrogated) in the absence of functional immune cell PPAR γ.

Figure 10A:
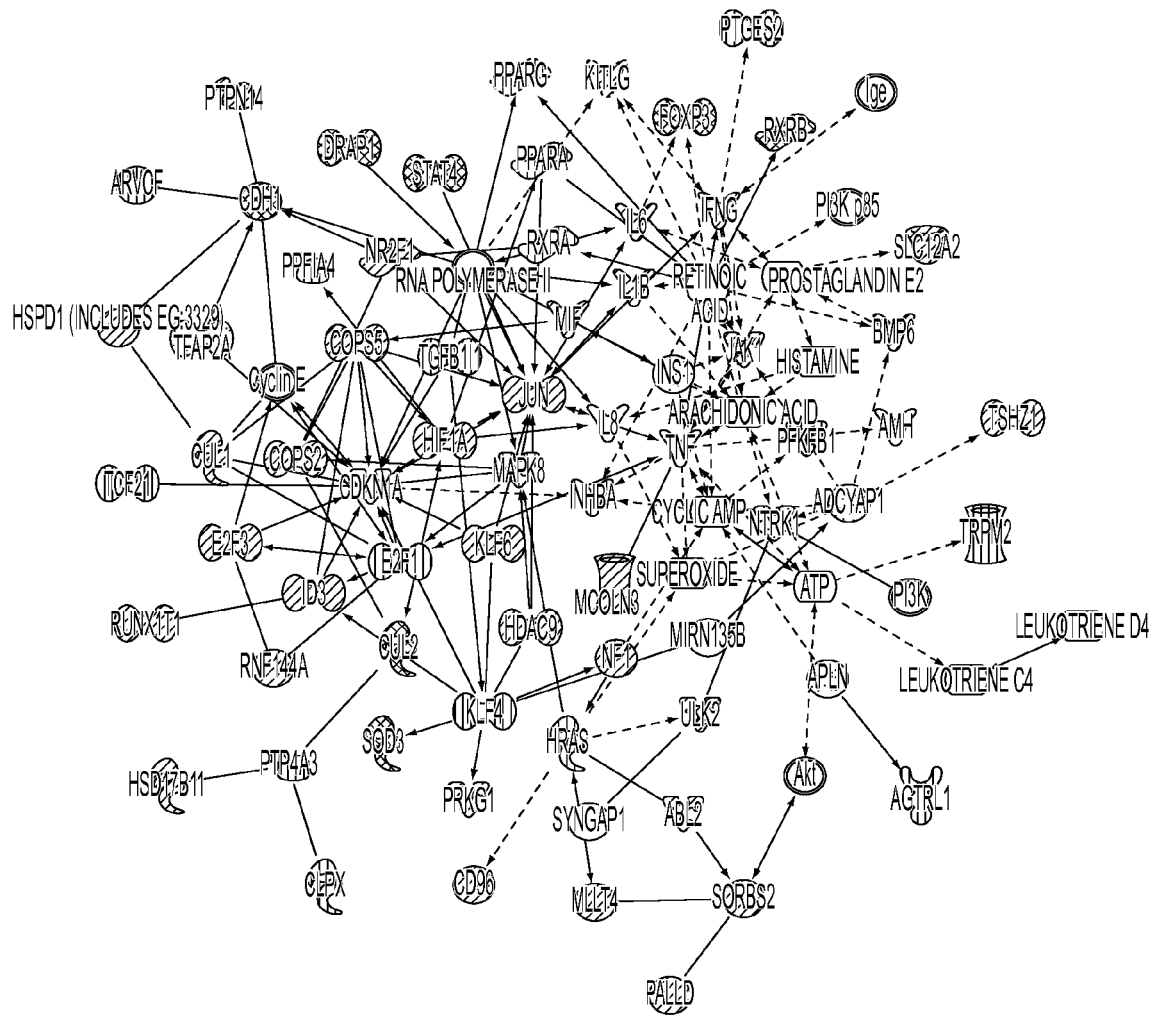
FIG. 10 is a network analysis result for 43 genes corresponding to the lipopolysaccharide (LPS)-abscisic acid (ABA) interaction in the spleen. Green: genes up-regulated; red: genes down-regulated. The color intensity represents the level of up or down regulation. A: PPAR γ-expressing mice; B: Immune cell-specific PPAR γ null mice. The top center region of the network contains nuclear receptor genes (PPAR α, γ, RXRA, RXRB). The upper right region contains clusters of inflammatory genes (IL-6, IL1β, TNF-α, IFN-γ, MIF) and arachidonic acid-derived lipid mediators. ABA modulates the expression of the above gene clusters in PPAR γ-expressing mice, but its effects are abrogated or impaired in immune cell-specific PPAR γ null mice.
Figure 10B:
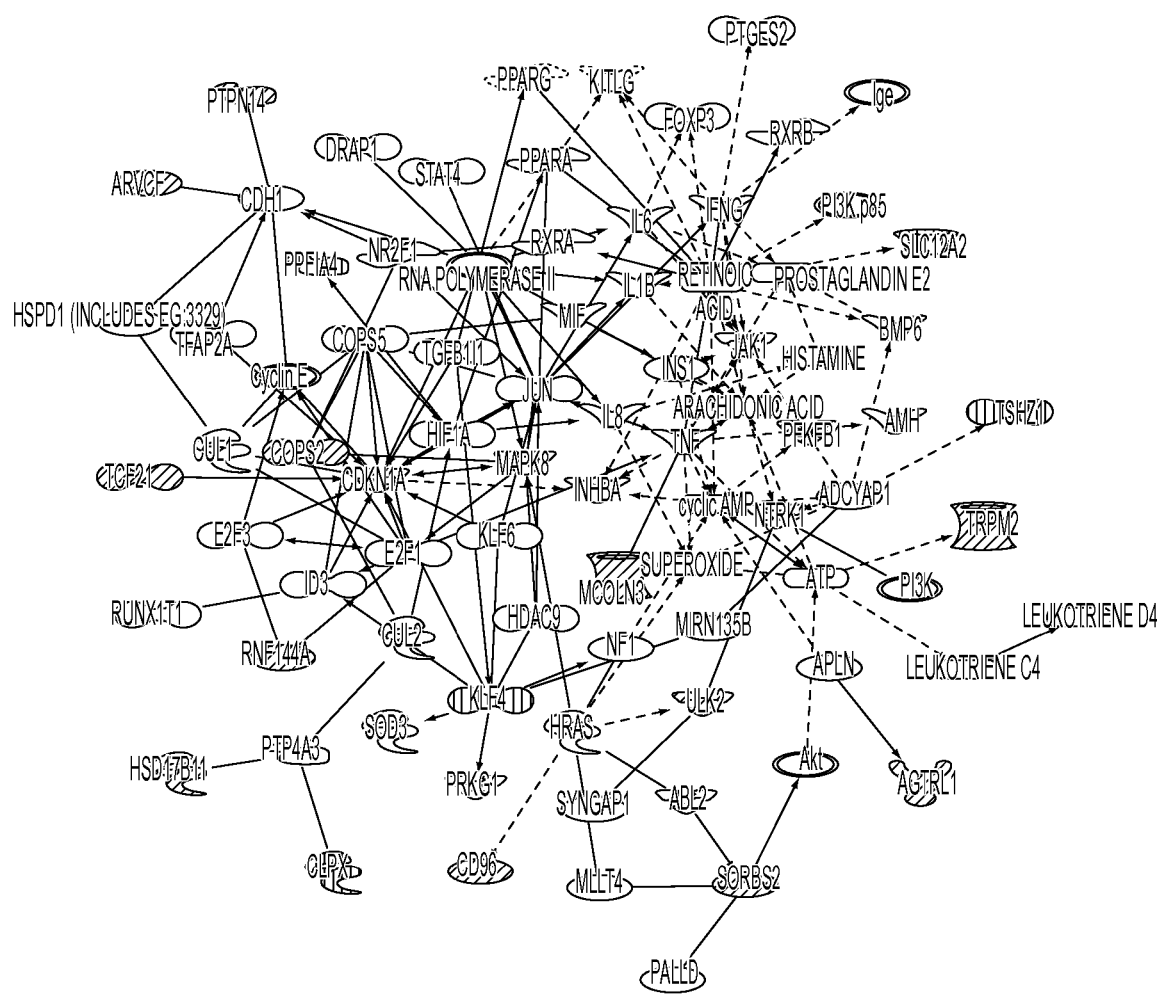

The network analyses performed in genes differentially regulated by ABA in LPS challenged mice revealed a complex ABA-controlled network that illustrates a down-regulation of pro-inflammatory genes (IL-6, IL-1β, MIF and IFN-γ) and inflammatory signaling molecules such as c-Jun and Janus kinase 1, up-regulation of nuclear receptors (i.e., PPAR γ, PPAR α, RXRα, and RXRβ), an anti-inflammatory cytokine (i.e., TFG-β, the transient receptor potential cation channel, subfamily M, member 2 (TRPM2), and the hypoxia-inducible factor (HIF)-1α, a transcription factor driving glycolytic metabolism (FIG. 10A). Many of these transcriptional modulatory effects of ABA were abrogated or impaired in spleens recovered from immune cell-specific PPAR γ null mice (FIG. 10B).

Figure 7A:
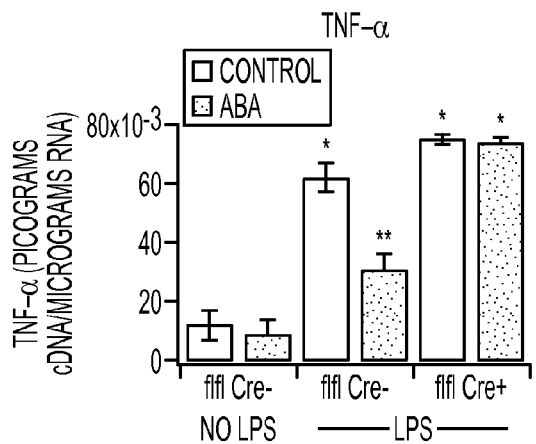
FIG. 7 illustrates the effect of dietary abscisic acid (ABA) on splenic gene expression following an intraperitoneal (i.p.) lipopolysaccharide (LPS) challenge of PPAR γ-expressing (flfl-Cre−) and conditional PPAR γ null (flfl-Cre+) mice. Quantification of mRNA expression of (A) TNF-α, (B) nuclear receptor co-activator 6 (NCOA6), (C) PPAR γ, and (D) Glut4 in spleens of mice administered control or ABA-supplemented (100 mg/kg). Splenic samples were collected 6 hours following an in vivo (i.p.) challenge with LPS at 375 µg/kg in 0.1 ml of saline (* vs **, P<0.05). Results are presented as means±SEM of groups of 10 mice.
Figure 7B:
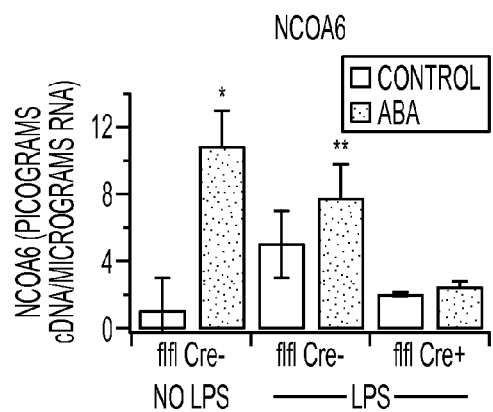
Figure 7C:
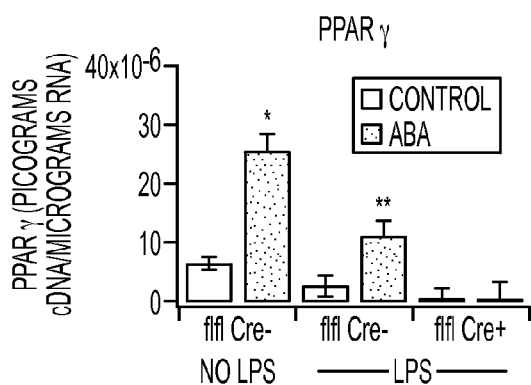
Figure 7D:
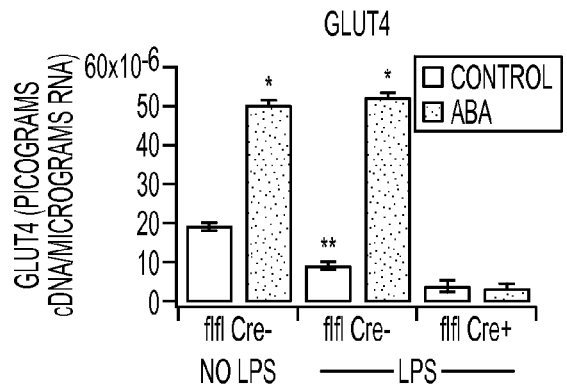

Modulation of inflammatory and PPAR γ-responsive gene expression by ABA. The microarray analyses indicated that ABA suppressed the LPS-mediated induction of inflammatory genes in the spleen. Here we determined whether some of these genes were differentially affected by real-time RT-PCR. We provide evidence that ABA suppressed LPS-mediated up-regulation of TNF-α in a PPAR γ-dependent manner (FIG. 7A) but had no effect on iNOS mRNA expression (data not shown). Interestingly, NCOA6 mRNA expression was increased by ABA, regardless of the LPS challenge (FIG. 7B). In addition, ABA mitigated the LPS-mediated suppression of PPAR γ and Glut4 (FIGS. 7C & D). These effects of ABA were abrogated in mice lacking PPAR γ in immune cells.

Figure 8A:
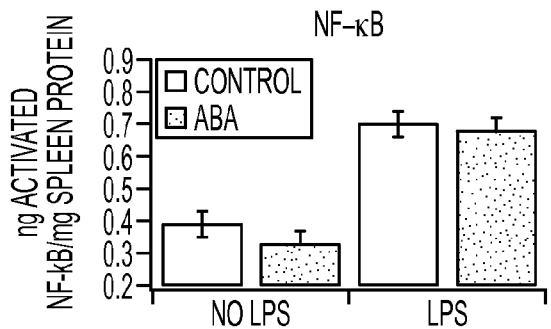
FIG. 8 illustrates the effect of abscisic acid (ABA) on splenic nuclear factor-κB (NF-κB) and activated nuclear factor of activated T cells c1 (NFATc1) activation following a lipopolysaccharide (LPS) challenge. The concentration of activated NF-κB (A) and NFAT (B) in the spleens of control or LPS-challenged mice and bone marrow macrophages derived from wild-type (WT) or macrophage-specific PPAR γ null mice (flfl LysozymeM-Cre+) (C) was determined using an enzyme-linked immunosorbent-based assay. For the NF-κB reporter activity assay 3T3-L1 cells were transfected as described in the Materials and Methods before being exposed to increasing concentrations (1.25, 2.5, 5, or 10 µM) of ABA, DMSO alone (no treatment), or rosiglitazone (1, 5 and 10 µM). After 20 hours, the relative luciferase activity was assessed for each treatment. *P<0.05. In vivo results are presented as means±SEM of groups of 10 mice. In vitro findings are representative results of three independent experiments run in triplicate.
Figure 8B:
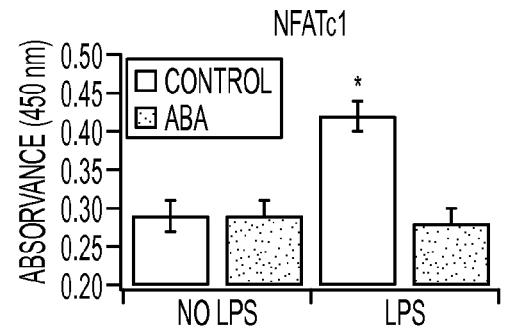
Figure 8C:
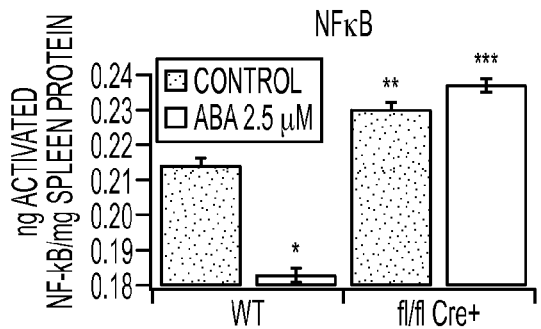
Figure 8D:
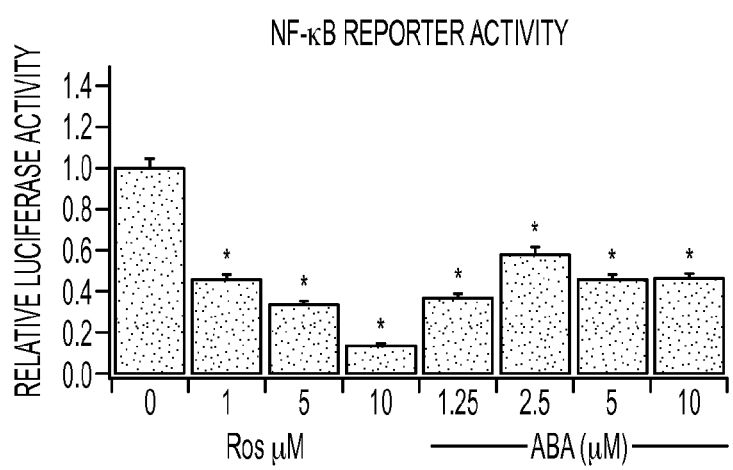

Modulation of NF-κB and NFATc1 activities by ABA. We next examined the effect of ABA on NF-κB and NFATc1 activation in spleens of LPS-challenged mice and found that while ABA did not affect NF-κB activity (FIG. 8A), it significantly decreased LPS-mediated activation of NFATc1 (FIG. 8B). We next quantified the effect of ABA on NF-κB activation of BMM following stimulation with LPS/IFN-γ and demonstrated that 2.5 µM ABA significantly decreased NF-κB p65 activity in nuclear extracts from PPAR γ-expressing primary macrophages (FIG. 8C). The loss of PPAR γ in macrophages resulted overall in greater NF-κB activity when compared to WT and further activation induced by ABA (FIG. 8C). We then performed a NF-κB reporter activity assay in 3T3-L1 cells (FIG. 8D) and RAW macrophages (data not shown) and demonstrated that ABA significantly suppressed NF-κB reporter activity in 3T3-L1 cells (FIG. 8D) but it increased it in RAW macrophages (data not shown). Of note, 3T3-L1 cells express endogenous PPAR γ, whereas RAW macrophages do not (36). In summary, these data demonstrate that ABA antagonizes inflammatory pathways via PPAR γ.

ABA is a phytohormone that plays important roles in the plant life cycle (1). In addition to its effects in regulating plant response to stress, endogenous ABA activity has also been reported in fungi (37), marine sponges (38, 39), and more recently human granulocytes (40), monocytes (34) and pancreatic beta cells (7), suggesting that endogenously generated ABA may play an important role in regulating immune and inflammatory processes.

Our group demonstrated the pre-clinical efficacy of oral ABA administration in mouse models of obesity-related inflammation, diabetes, atherosclerosis and inflammatory bowel disease (2-6). We demonstrated that ABA treatment activates PPAR γ in 3T3-L1 pre-adipocytes (4) and its blood glucose-lowering actions require the expression of PPAR γ in immune cells (3). Surprisingly, ABA synergizes with Ros to improve glucose tolerance and regulate macrophage accumulation in adipose tissue (2). Since Ros saturates the LBD of PPAR γ, the reported synergism between the compounds suggests that ABA might activate PPAR γ through an alternate mechanism that differs from that of TZDs. Indeed, this study demonstrates that both (+) and (−) ABA isomers can activate PPAR γ reporter activity in RAW macrophages. However, at the molecular level, the effect of ABA on PPAR γ is independent of direct binding to the LBD of this receptor. More specifically, results of docking studies indicate ABA does not bind to the portion of the PPAR γ-binding cavity that is associated with activation (29-31). Moreover, unlike TZDs, if ABA docking is restricted to this binding site, its ring head structure, rather than the carboxylate group, unexpectedly interacts with hydrogen-bonding residues. As such, many subsequent hydrophobic interactions necessary for activation-related conformational changes might be absent. The inability of ABA to bind directly to the site of agonism within the PPAR γ LBD is further validated by competitive ligand-binding assays demonstrating the inability of ABA to displace the tracer. Hence, this is the first report demonstrating that ABA activates PPAR γ independently of the PPAR γ LBD, suggesting the existence of a potential molecular target for ABA upstream of PPAR γ. Together, these molecular findings are consistent with previous in vitro evidence demonstrating that the ABA-induced activation of PPAR γ reporter activity can be inhibited through blocking cAMP production or inhibiting PKA activity (2), suggesting that upstream cAMP/PKA signaling may be required for the alternative activation of PPAR γ by ABA.

Bruzzone and colleagues showed that ABA induced cAMP overproduction and PKA activation in insulin-secreting pancreatic β-cell lines (7). We previously reported increased intracellular cAMP accumulation in human aortic endothelial cells (5). Herein we demonstrate that ABA treatment of activated primary mouse splenocytes and macrophages increases cAMP accumulation, although the specific molecular events connecting a membrane-initiated mechanism leading to cAMP accumulation and activation of PPAR γ remains unknown. The G protein-coupled LANCL2 represents a possible membrane-associated target for ABA involved in the initiation of the cAMP signal in leukocytes that has been reported to play a role in the signaling of ABA in human granulocytes (32). We identified a putative ABA-binding site on the surface of LANCL2 and demonstrated that ABA treatment of splenocytes and macrophages results in increased cAMP accumulation. In addition, our molecular docking studies predicted that ABA and TZDs (e.g., Ros and PGZ) share a binding site on LANCL2 (41), thereby providing a nexus between signaling pathways and indicating that TZDs can bind both PPAR γ and LANCL2; docking studies suggest that ABA binds effectively to LANCL2 but binding of ABA to PPAR γ is at sites or in an orientation that does not activate this receptor. To investigate the importance of LANCL2 in ABA-mediated activation of PPAR γ we determined whether knocking down LANCL2 in RAW macrophages by using siRNA impaired or abrogated the effect of ABA on PPAR γ reporter activity. Our findings indicate that knocking down about 80% of LANCL2 mRNA significantly attenuates ABA's effect on PPAR γ activity. Interestingly, consistent with the prediction of our molecular model of LANCL2 indicating binding of Ros (41), the PPAR γ agonistic affects of Ros were also significantly diminished in siRNA-treated cells. These findings suggest that LANCL2 is an influential modulator of PPAR γ activity, though the mechanism underlying this affect is unclear. Sturla et al imply that LANCL2 may form an ABA-sensitive complex with Gi protein(s) upstream from adenylate cyclase (32). Indeed, LANCL2 could influence Gi either indirectly by inducing post-translational modifications or through binding interactions; the former would require LANCL2 to have an undiscovered catalytic function and the latter would not. Interestingly, GSH/GSSG interacts with LANCL1 and to a weaker extent with LANCL2 (42, 43); all of which provides evidence in support of potential catalytic functions in the LANCLs.

It is well accepted that Ros activates PPAR γ by binding directly to its LBD. In fact, our data corroborate this assertion. However, our virtual screening results demonstrate that Ros and other TZDs, in addition to binding PPAR γ, can also bind LANCL2 in the same region of the protein targeted by ABA (41); all of which suggests that TZDs target PPARs both directly binding to their LBD and indirectly by targeting the LANCL2 pathway. The cross-talk between PPAR γ and LANCL2 is not well-understood and further investigation into this molecular interaction may shed new light on the mechanistic components of this pathway linked to differences in efficacy and side effects (i.e., ABA vs TZD class).

Since LANCL2 is coupled to a pertussis toxin-sensitive G-protein that regulates the cAMP synthesizing activity of adenylate cyclase (32), the cAMP signaling pathway represents a likely mechanism underlying some of the immune modulatory actions of ABA. Furthermore, there is some evidence demonstrating that cAMP/PKA activation increases basal and ligand-induced PPAR γ activity (44), providing a basis for either crosstalk between the cAMP and PPAR γ pathways or the existence of a common cAMP/PKA/PPAR γ signaling axis. This pathway parallels findings related to the retinoic acid receptor (RAR) pathway, since RAR activity was significantly increased by cAMP-elevating agents (45). Like PPAR γ, RAR is a nuclear receptor that becomes activated primarily through ligand binding (i.e., retinoic acid for RAR and TZDs or lipids for PPAR γ) to its LBD, although LBD-independent activation is also possible and can be enhanced by cAMP/PKA. While we demonstrated that ABA does not increase reporter activity of RXR or RAR (data not shown), our findings suggest that, like retinoic acid, ABA may favor the latter LBD-independent mechanism of PPAR γ activation. However, it remains unknown whether, by acting on membrane-initiated signaling, ABA can increase the sensitivity of PPAR γ to endogenously generated ligands acting on the LBD. Notably, the generation of these endogenous ligands would increase during inflammation, lending support to the theory that ABA plays an important role in regulating immune and inflammatory responses.

We next investigated the ability of ABA to modulate the production of inflammatory mediators both in BMM and in vivo following an LPS challenge in mice. Our in vitro findings demonstrate that ABA inhibits LPS-induced production of MCP-1 and $PGE_2$ by macrophages in a PPAR γ-dependent manner. These anti-inflammatory effects are consistent with suppressed surface expression of TLR4, a surface receptor for LPS, in MLN macrophages and T cells from PPAR γ-expressing, LPS-challenged mice that received ABA. However, this anti-inflammatory effect of ABA was abrogated or impaired in immune cell-specific PPAR γ null mice, indicating that PPAR γ mediates the inhibitory actions of ABA on macrophage and T cell TLR4 expression in vivo during an LPS challenge. Alternatively, PPAR γ could be required for TLR4 expression, regardless of the drug. Of note, bacterially induced signals, via TLR4, affect the expression of PPAR γ (46). Our data suggest that the opposite may also be true. Nonetheless, these novel findings are in contradiction with previous reports describing ABA as a pro-inflammatory mediator in vitro (34, 40). A possible explanation for the divergent findings between this report and studies by Magnone and colleagues (34) in monocytes that show increased MCP-1 and $PGE_2$ is that monocytes express low levels of PPAR γ and this receptor is only upregulated during differentiation into macrophages (47). Based on our model PPAR γ is required for the anti-inflammatory actions of ABA. Therefore examining the functional effect of ABA in monocytes devoid of PPAR γ results in an inadvertent experimental bias towards the activation of pro-inflammatory pathways downstream of LANCL2. In support of this assertion, our flow cytometry data in LPS-challenged mice demonstrates a PPAR γ-dependent effect of ABA in tissue macrophages (i.e., MLN), where PPAR γ is expressed, but a PPAR γ-independent effect of ABA in blood monocytes. The inhibitory effect of ABA on the production of $PGE_2$ may also influence the induction of adaptive immune responses since $PGE_2$ is known to suppress interleukin-2 (IL-2) production and in instances in which $PGE_2$ is decreased by other compounds (i.e., Vitamin E) IL-2 production by CD4+ T cells is increased, thereby resulting in greater lymphocyte proliferation (48). In support of this hypothesis, our unpublished data demonstrates that ABA increases IL-2 production and lymphocyte proliferation. While the suppressive action of ABA on inflammation did not seem to match its potential immunostimulatory properties, other naturally occurring compounds such as conjugated linoleic acid have been shown to have immunoenhancing properties while at the same time suppressing inflammation by activating PPAR γ (49).

To more comprehensively determine the effect of ABA on gene expression and to identify future target candidates we used global gene expression profiling of spleens from mice challenged with LPS. We present a complex ABA-controlled regulatory network that illustrates a down-regulation of pro-inflammatory cytokines (IL-6, IL-1β, MIF and IFN-γ) and inflammatory signaling molecules such as c-Jun and Janus kinase 1 (JAK1), up-regulation of nuclear receptors (i.e., PPAR γ, PPAR α, RXRαc, and RXRβ), an anti-inflammatory cytokine (i.e., TFG-β), TRPM2, a cation channel that can be activated by free intracellular ADP-ribose in synergy with free intracellular calcium (50) and, in line with the beneficial effects of ABA on glucose homeostasis (3, 4), HIF-1α, a transcription factor driving glycolytic metabolism, thereby maintaining ATP generation (51). The up-regulation of TRPM2 is consistent with the finding that ADP-ribose is the second messenger of ABA in human granulocytes (40). Of note, mitogen activated protein kinase kinase kinase kinase 2 and adenylate cyclase, which catalyzes the conversion of ATP to cAMP were also down-modulated by LPS although ABA mitigated this effect in a PPAR γ-dependent manner, an effect that could be associated with the cAMP/PKA and the MAPK pathways. ABA also suppressed the aminoacyl-tRNA biosynthesis pathway which contains genes that serve as signaling molecules in the immune response (52). Lysyl-tRNA synthetase is linked to pro-inflammatory response (53), while several aminoacyl-tRNA synthetases and their proteolytic fragments have been shown to exert chemoattractant properties (54). Down-modulation of these molecules by ABA may contribute to its anti-inflammatory function in the present context. Consistent with our findings in TLR4 expression, the deficiency of PPAR γ in immune cells drastically reduced the number of genes differentially expressed due to the administration of ABA.

Figure 9:
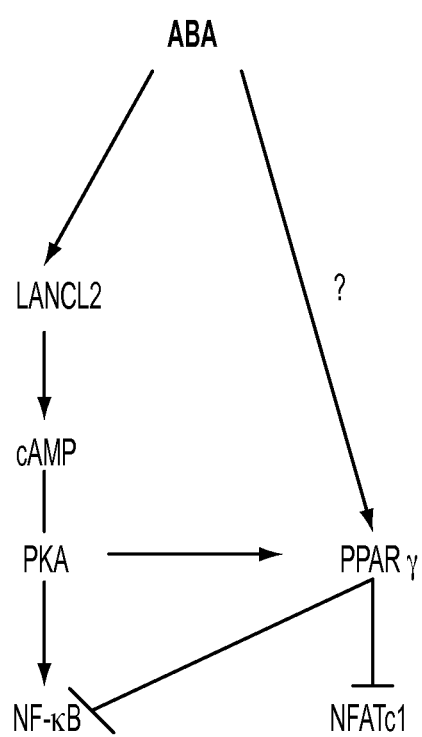
FIG. 9 illustrates a molecular mechanism underlying activation of PPAR γ by abscisic acid (ABA). By binding to LANCL2 ABA activates the cAMP-PKA pathway that is essential for maintaining and enhancing PPAR γ activity in the context of inflammation. In turn, activation of PPAR γ by ABA results in antagonism of NFATc1 and NF-κB activities. Based on this proposed bifurcating pathway mechanistic model, ABA administration in the absence of functional PPAR γ would result in a net pro-inflammatory effect potentially mediated via PKA-dependent activation of NF-κB.

Confirmatory real-time RT-PCR results indicate that ABA treatment repressed the expression of LPS-induced TNF-α and upregulated PPAR γ, and its related genes NCOA6, and Glut4 in spleen. These modulatory effects of ABA in splenic gene expression were abrogated or impaired in immune cell-specific PPAR γ null mice. The suppression of inflammatory genes could be mediated through ABA-induced suppression of NF-κB activity in primary mouse macrophages. Since, this effect was observed in wild-type but not in PPAR γ null macrophages the inhibitory effect of ABA on macrophage NF-κB activity is likely mediated through a PPAR γ-dependent mechanism, possibly related to co-activator competition. On the other hand, the antagonistic effect of ABA on spleen NFATc1 echoes the inhibitory effect of TZDs on TNF-α production by macrophages and osteoclasts which is mediated by down-regulation of NFATc1 (55). Lending additional support to the PPAR γ requirement for ABA's anti-inflammatory activity, ABA decreased NF-κB reporter activity in 3T3-L1 cells but it increased this activity in RAW macrophages. These findings match our proposed bifurcating mechanistic model since RAW macrophages do not express endogenous PPAR γ (36) whereas 3T3 cells do (56). Indeed, we propose that activation of the LANCL2 pathway will lead to enhanced NF-κB activation via PKA in the absence of PPAR γ activation. The proposed bifurcating pathway model (FIG. 9) also provides an explanation as to why ABA elicited pro-inflammatory effects in monocytes that express limited or null concentrations of PPAR γ (34).

PPAR γ can form complexes with other transcription factors and target co-repressor complexes onto inflammatory gene promoters (12), thereby decreasing inflammation. Our findings are consistent with previous studies demonstrating that treatment of CD4+ T cells with PPAR γ agonists (i.e., ciglitazone or 15dPGJ2) triggered the physical association between PPAR γ and NFATc1 (57) or with NF-κB in gut epithelial cells (11). It remains unknown whether the effect of ABA on PPAR γ is mediated directly by acting on the receptor or indirectly through LANCL2/cAMP initiated signaling and LANCL catalytic functions. Further studies are warranted to determine the impact of ABA's immunoregulatory actions on human infectious and immune-mediated diseases.

Example 2

Effect of Dietary ABA on Influenza Virus-Associated Pulmonary Inflammation and Mechanism of Action Recent studies on the pathogenesis of Influenza A virus infections have highlighted the relevance of disassociating the cytopathic effects caused by the virus from the damage resulting from the host's response following the viral infection. The use of immunotherapeutics targeting the immune response and not the virus to ameliorate disease severity and minimize tissue destruction has been proposed as an alternative approach to treat flu-associated morbidity. Influenza A virus infects epithelial cells lining the respiratory airways activating TLR3 and RIG1 pathways after recognition of double stranded viral RNA. The immediate response to influenza virus infection is the transcription of type I IFN and subsequent apoptosis of infected cells. In addition, the initial anti-viral response leads to the upregulation of pro-inflammatory cytokines and chemokines. The secretion of CXCL10, CXCL2 and IL-8, or its equivalent in mice KC, results in homing of myeloid cells, namely neutrophils and proinflammatory monocytes into the lung parenchyma. These monocytes differentiate into exudate macrophages and monocyte-derived dendritic cells (DC), which can aggravate the infection by secreting more inflammatory mediators. CCL2 (MCP-1) also contributes to the recruitment of monocytes that differentiate into TNF-α and iNOS producing DC (tipDC). Human cases of influenza A (H5N1) were dominated by high viral loads and increased levels of inflammatory cytokines and chemokines (IP-10, MIG and MCP-1) in peripheral blood, which were even more accentuated in patients that succumbed to the infection (64). Neutrophils and macrophages infiltrating the lungs of mice challenged with the reconstructed Influenza A/1918 (H1N1) overexpressed inflammatory genes (65). Moreover, even though the newly emerged Influenza A/2009 (H1N1) generally caused mild disease, reported pathologic changes of fatal cases were similar to those described for the Influenza A/1918 (H1N1) pandemia, and were characterized by affection of the lower respiratory tract with bronchiolitis, alveolitis and neutrophilic infiltration (66).

The underlying mechanisms by which the dysregulation of cytokine and chemokine production contributes to the pathogenesis of flu are not completely understood. Experimental infection of mice lacking key cytokines, chemokines or their receptors have yield inconclusive results due to the built-in redundancies found in the cytokine/chemokine signaling pathways. For instance, the loss of Type I IFN are both associated with excessive lung inflammation and lower survival rates following infections with highly pathogenic strains of influenza virus. In contrast, the loss of TLR3 ameliorates disease severity, suggesting that TLR3 may be linked with influenza virus-related pathology. However, CCR2 KO mice were found to be more resistant or behave similar to wild-type strain. In support of the role of the host inflammatory response in the pathogenesis of influenza, recent reports have shown that the use of immunomodulators that partially block inflammatory cascades improve the outcome of influenza A virus infections. For instance, inhibition of cyclooxygenase 2 combined with mesalazine, a therapy for inflammatory bowel disease (IBD), and the antiviral zanamivir improved influenza virus-related inflammation. It has also been shown that a peroxisome proliferator-activated receptor (PPAR) γ agonist, pioglitazone (Actos), improves survivability of mice challenged with a highly pathogenic strain by lowering the expression of the inflammatory chemokines MCP-1 and MCP-3 and decreasing the influx of inflammatory cells into the lung. Therefore, the development of novel anti-inflammatory broad-based host-targeted therapeutics represents a promising new avenue to decrease tissue damage associated with influenza virus infection.

Our group has developed novel anti-inflammatory immunotherapeutics by using robust computational screening of compound libraries (41, 67), followed by experimental validation in vitro and in pre-clinical efficacy studies. As a result of these screening approaches we have identified the plant hormone abscisic acid (ABA) as a molecular target for both lanthionine synthetase component C-like 2 (LANCL2) and PPAR γ (68). Moreover, we have demonstrated that binding of LANCL2 modulates PPAR γ activity in immune cells through a bifurcating pathway involving LANCL2 and an alternative, ligand-binding domain-independent mechanism of PPAR γ activation (68). Results of pre-clinical efficacy studies demonstrate that ABA ameliorates experimental IBD through a mechanism that requires expression of PPAR γ in T cells (6, 69). The objective of this study was to determine whether ABA treatment prevents or ameliorates influenza virus-related pulmonary immunopathology and to characterize the mechanisms by which this natural immunotherapeutic regulates immune responses. We also examined whether the deletion of PPAR γ in immune and epithelial cells abrogates the effects of ABA on influenza. Our data demonstrates that ABA ameliorates disease activity, lung inflammatory pathology, accelerates recovery, ameliorates infection-related weight loss and decreases mortality in mice infected with influenza virus.

Materials and Methods

Animal Procedures. Eight week old PPAR flfl MMTV-Cre+ mice, with a Cre recombinase targeted to the MMTV- Cre promoter (MMTV-Cre+, n=20), and control MMTV-Cre− (MMTV-Cre−, n=20) littermates in a C57BL/6 background were housed at the animal facilities at Virginia Polytechnic Institute and State University in a room maintained at 75° F., with a 12:12 h light-dark cycle starting from 6:00 AM. All experimental procedures were approved by the Institutional Animal Care and Use Committee of Virginia Tech and met or exceeded requirements of the Public Health Service/National Institutes of Health and the Animal Welfare Act. The mice were genotyped for the PPARγ gene using previously published genotyping protocols (13). Mice were fed purified AIN-93G rodent diets with and without ABA in which all nutritional requirements were met or exceeded. Based on previous findings (13), a dose of 100 mg ABA/kg of diet was determined to be ideal for down-modulating systemic inflammation and glucose tolerance in mouse models of obesity and diabetes (4) and decreasing intestinal inflammation in mouse models of IBD (6, 69). All the experimental diets contained the same amount of energy (isocaloric) and protein (isonitrogenous) as previously described (13). One-month old mice (n=10 for each treatment and genotype) were administered the experimental diets supplemented with 100 mg/kg of ABA for 36 d prior to the intranasal challenge with influenza virus and throughout the challenge period equivalent to an optimal prophylactic dosage of 0.2 mg ABA a day for each mouse, based on average feed intake of 2 g food/mouse/day. Body weights were monitored on a daily basis following challenge to determine the effect of ABA and genotype on weight loss.

Influenza virus challenge. To investigate whether ABA diminishes the pulmonary inflammatory response, we infected PPAR γ fl/fl; MMTV-cre− (WT) and PPAR γ fl/fl; MMTV-cre+ (conditional KO-(cKO)) mice intranasally with $5 \times 10^4$ tissue culture infectious dose 50 $(TCID)_{50}$ Influenza A/Udorn (H3N2) given in 50 µl of sterile PBS under anesthesia with xylazine and ketamine (50-150 mg/kg). Mock-infected mice received the same volume of PBS.

Quantification of viral loads. Viral loads in lung homogenates were determined as described previously (70). Briefly, serial 10-fold sample dilutions of lung homogenates were incubated with MDCK cells for 1 hour at 37° C. to allow for virus adsorption. Subsequently, cells were washed and incubated for 3 days at 37° C. in the presence of 1.5 µg/ml TPCK-treated trypsin (Sigma) and cytopathic effects were recorded. Viral loads are reported as 50% tissue culture infectious dose units ($TCID_{50}$/ml) per gram lung tissue as determined by the Reed-Muench method (71).

Pulmonary Histopathology. Lungs were inflated at necropsy and lung sections were fixed in 10% buffered neutral formalin, later embedded in paraffin, and then sectioned (5 µm) and stained with H&E stain for histological examination. Lungs were graded with a compounded histology score including the extent of 1) epithelial necrosis/regeneration, 2) presence of desquamated cells and inflammatory cellular infiltrates within the airways, 3) presence of leukocytic infiltrates in epithelium and lamina propria of airways, 4) presence of marginated leukocytes and inflammatory cells surrounding blood vessels and, and 5) presence of edema, fibrin deposits or hyaline membranes. The sections were graded with a score of 0-4 for each of the previous categories and data were analyzed as a normalized compounded score.

Bronchoalveolar lavage (BAL). To obtain leukocytes from the alveolar space, the trachea was cannulated post-mortem by using a gavage needle and lungs were washed three times with 1 ml of room temperature PBS that were subsequently combined. Approximately 90% of the total instilled volume was consistently recovered.

Western blot. Cells obtained by lavage and lung specimens were homogenized in RIPA buffer (150 mM NaCl, 1.0% IGEPAL® CA-630, 0.5% sodium deoxycholate, 0.1% SDS, 50 mM Tris, pH 8.0) containing protease and phosphatase inhibitors and incubated for 30 min on ice. Whole lysates were cleared by centrifugation (10,000 rpm for 10 min) and protein concentration was measured using a DC protein assay kit (Bio-Rad Laboratories). Whole lysates were cleared by centrifugation (10,000 rpm for 10 min). Proteins were separated on a 10% SDS-PAGE gel and transferred to polyvinylidene difluoride (PVDF) membrane. The membrane was blocked with 1×TBS-T (20 mM Tris-HCl pH 7.6, 8.5% NaCl, 0.1% Tween-20) containing 3% Bovine Serum Albumin (BSA, Sigma-Aldrich) 30 min at room temperature. Membranes were incubated overnight at 4° C. with anti-PPAR antibody diluted in 1×TBS-T 3% BSA. After 3 washes with 1×PBS-T, membrane was incubated for 45 min at room temperature with anti-mouse IgG conjugated to horseradish peroxidase (HRP). The antigen detection was performed with the ECL (Bio-Rad Laboratories) chemiluminescent detection system.

Real-time RT-PCR. Total RNA was isolated from the lungs and BAL-derived cells using the RNA isolation Minikit (Qiagen) according to the manufacturer's instructions. Total RNA (0.5 to 1 µg) was used to generate complementary DNA (cDNA) template using the iScript cDNA Synthesis Kit (Bio-Rad, Hercules, Calif.). Starting cDNA concentrations for genes of interest were examined by real-time quantitative PCR using an iCycler IQ System and the iQ SYBR green supermix (Bio-Rad). A standard curve was generated for each gene using 10-fold dilutions of purified amplicons starting at 5 pg of cDNA and used later to calculate the starting amount of target cDNA in the unknown samples. PCR was performed on the cDNA using Taq DNA polymerase (Invitrogen, Carlsbad, Calif.) and using previously described conditions (13). Each gene amplicon was purified with the MiniElute PCR Purification Kit (Qiagen) and quantitated on an agarose gel by using a DNA mass ladder (Promega). These purified amplicons were to generate standard curves in the real-time PCR assay. Real-time PCR was used to measure the starting amount of nucleic acid of each unknown sample of cDNA on the same 96-well plate.

Statistical analyses. Data were analyzed as a 2×2 factorial arrangement of treatments within completely randomized design. The statistical model was: $Y_{ijk} = \mu + Genotype_i + Treatment_j + (Genotype \times Treatment)_{ij} + error A_{ijk}$, in which µ was the general mean, $Genotype_i$ was the main effect of the $i_{th}$ level of the genotypic effect (expression of PPAR by immune and epithelial cells), $Treatment_j$ was the main effect of the $j_{th}$ level of the dietary effect (ABA vs control), $(Genotype \times Treatment)_{ij}$ was the interaction effect between genotype and diet, and error A representing the random error. To determine the statistical significance of the model, analysis of variance (ANOVA) was performed using the general linear model procedure of Statistical Analysis Software (SAS), and probability value (P)<0.05 was considered to be significant. When the model was significant, ANOVA was followed by Fisher's Protected Least Significant Difference multiple comparison method.

Results

Influenza virus infection upregulates PPAR γ in the lung.

PPAR γ is expressed in the lungs of healthy mice (72), however the expression of PPAR γ during influenza virus infection has not been reported before. Because we were proposing to use an intervention targeting PPAR γ, we evaluated changes in protein expression overtime following infection. FIG. 11 shows that PPAR γ is significantly upregulated and reaches its maximum expression in the lungs as early as 24 hours post-infection, it slightly declines on day 3 and again increases between days 5 and 9 post-infection. The kinetics of PPAR γ expression in cells obtained from the airway spaces, which correspond mainly to infiltrated immune cells, was very different. Protein was not detectable until day 3 post-infection and reached a maximum on day 9. These results indeed give support to interventions targeting PPAR γ via exogenous activation to ameliorate influenza virus-associated disease and lung pathology.

Effect of ABA and conditional PPAR γ deletion on influenza virus infection-associated weight loss and pulmonary pathology.

Based on previous work showing that ABA transactivates PPAR γ reporter activity in macrophages (68) and mimics the capacity of other PPAR γ agonists to suppress inflammation (2, 3) we hypothesized that ABA could ameliorate the inflammatory response that takes place during viral pneumonia. WT (PPAR γ fl/fl mice) and cKO (PPAR γ fl/fl; MMTV-Cre+) mice were fed either a diet containing ABA or a control diet without ABA for 36 days prior to an intranasal challenge with $5 \times 10^4$ $TCID_{50}$ of Influenza A/Udorn (H3N2). Weight loss was monitored daily after challenge as an indicator of disease severity. FIG. 12 shows that WT mice treated orally with ABA lost a maximum of 5% of their original body weight compared to 10% in mice that received control diet. Moreover, WT mice orally treated with ABA recovered their pre-challenge body weight between days 8 and 9 post challenge, while WT mice that received the control diet did not recover their original body weight until day 14 post-infection. Thus, oral ABA treatment ameliorated the clinical disease associated with influenza virus infection and accelerated the recovery. Our data also show that the effect of ABA in weight loss was PPAR γ dependent, since mice with defective PPAR γ expression in immune and epithelial cells behaved similar to WT mice fed the control diet. No differences were found between WT and cKO mice fed the control diet. In addition to minimizing influenza-associated weight loss, oral ABA administration improved survivability rates. Whereas 100% of mice in the WT/ABA group survived the infection, the rate dropped to 85.7% in the cKO mice in control diet, 71.2% in cKO mice in ABA diet and to 62.5% in WT mice in control diet (FIG. 12 B).

To evaluate whether ABA had any effect in virus replication, we measured viral loads in the lungs of mice at day 4 post-infection. FIG. 12 C shows that there were no significant differences in virus due to treatment or genotype, which indicates that ABA ameliorated the disease but not through a mechanism related to viral replication or early clearance.

ABA ameliorates influenza virus-associated lung pathology by diminishing the recruitment of inflammatory leukocytes.

Figure 13:
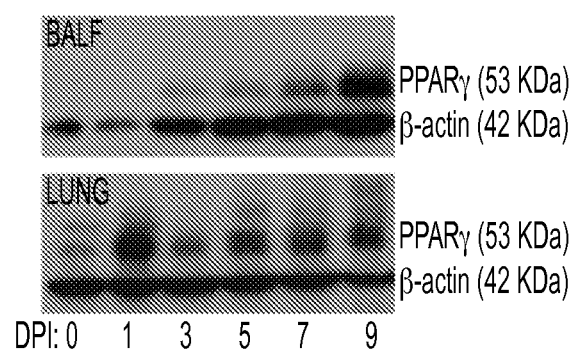
FIG. 13 illustrates peroxisome proliferator-activated receptor (PPAR) γ protein expression during influenza virus infection in cells obtained by bronchoalveolar lavage (BAL) (top), and lung (bottom). WT mice were infected with 5×10$^4$ tissue culture infectious dose 50 (TCID$_{50}$) of influenza A/Udorn (H3N2) and sacrificed 1, 3, 5, 7 or 9 days post-challenge. Non-infected mice (0) were used to assess baseline PPAR γ expression. Influenza virus infection upregulated PPAR γ protein, reaching highest expression at day one post-infection in whole lung and on day 9 post-infection in cells obtained from the bronchoalveolar space. Results from BAL correspond to cells pooled from at least 3 mice at each time point. Results from lung correspond to a sample obtained from one mouse at each time point and the picture is representative of 4 replicates with identical results.

To examine whether the improved clinical findings correlated with improved lung pathology, we evaluated microscopic pulmonary lesions at 2, 4 and 7 days post-infection in mice treated with ABA or control diets for 36 days and challenged with $5 \times 10^4$ $TCID_{50}$ of Influenza A/Udorn. Histopathological findings in the lungs of infected mice consisted of a cellular inflammatory pattern and absence of edema or fibrin deposition. Initially there was a predominance of necrosis of lung epithelial cells. Overall lesions spread from large airways to alveoli overtime. Cellular infiltrates were composed of mixed mononuclear cells and granulocytes and were located around large blood vessels and large airways initially, and in terminal airways and alveoli at later stages. These histopathological results demonstrate that ABA treatment did not affect the extent of epithelial necrosis occurring early following infection (FIG. 13 A-B), neither did it have any effect in epithelial recovery. However, we found that ABA treatment diminished the extent of vascular infiltrates (FIG. 13 C) as well as the infiltration of respiratory airways (FIG. 13 D) when compared to animals fed the control diet. Moreover our results show that the effect of ABA in decreasing lung tissue damage was PPAR γ dependent, since the beneficial effect of ABA on lung inflammatory cell infiltration observed in WT mice was abrogated in cKO mice fed ABA. Theses results suggest that the mechanism by which ABA protects from influenza-induced lung pathology is related to diminished recruitment of inflammatory cells into the lung and requires expression of PPAR γ in immune cells.

Figure 14A:
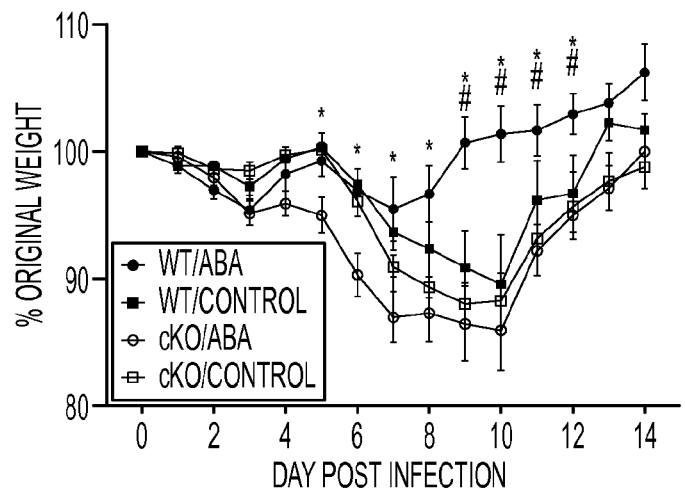
FIG. 14 illustrates the therapeutic effect of ABA treatment on weight loss (A), survival rates (B), and lung viral load (C) following infection with influenza virus. Wild-type (WT) or immune/epithelial cell-specific PPAR γ null mice (cKO) mice were fed either a control or an ABA-supplemented diet (100 mg/ABA kg of diet) for 36 days and then challenged with 5×10$^4$ tissue culture infectious dose 50 (TCID$_{50}$) of influenza A/Udorn (H3N2) virus for 14 days. The results indicate that ABA treatment prevented weight loss associated with influenza virus infection in the WT but not in the cKO mice, suggesting a PPAR γ-dependent mechanism of action. A similar beneficial pattern was observed in the survival rates for the ABA-treated mice. For the weight loss results data points with an asterisk (P<0.05) or a number sign (P<0.0001) are significantly different (n=10 mice per treatment and genotype). These effects were not associated to differences in lung viral load at day 4 post-infection.
Figure 14B:
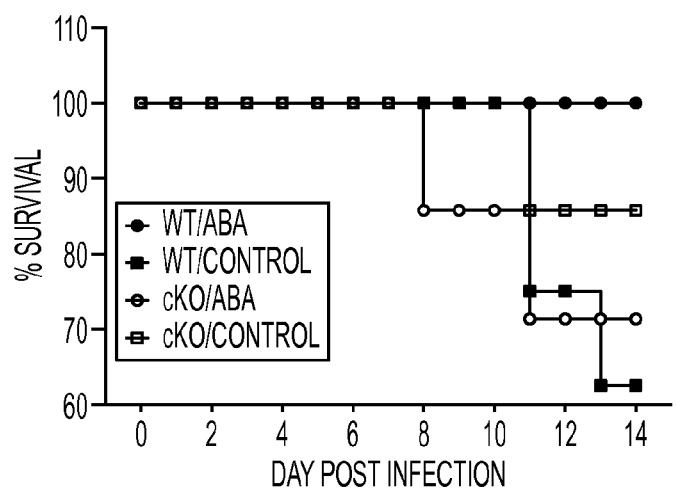
Figure 14C:
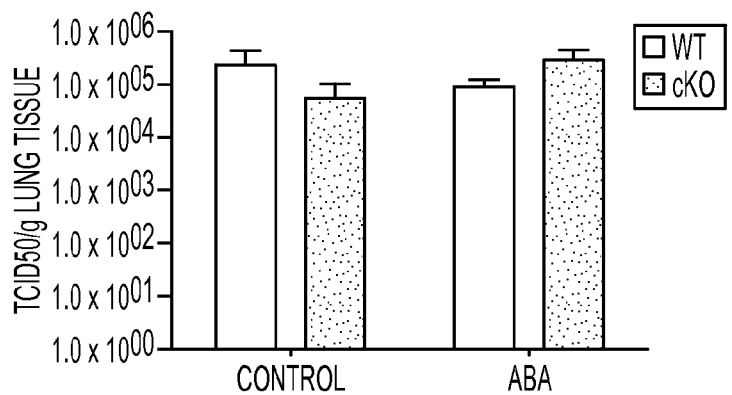
Figure 15A:
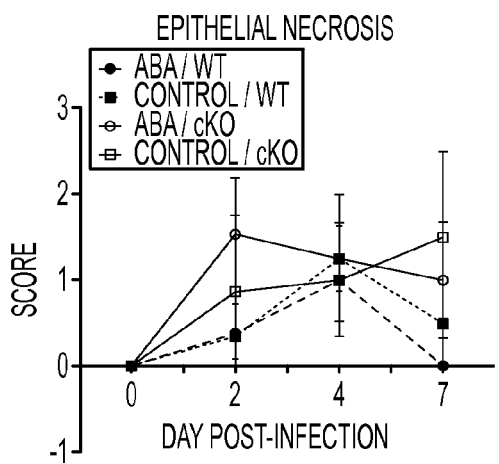
FIG. 15 illustrates the therapeutic effect of ABA treatment on lung histopathology on days 2, 4 and 7 following infection with influenza virus. Wild-type (WT) or immune/epithelial cell-specific PPAR γ null mice (cKO) mice were fed either a control or an ABA-supplemented diet (100 mg/ABA kg of diet) for 36 days and then challenged with 5×10$^4$ tissue culture infectious dose 50 (TCID$_{50}$) of influenza A/Udorn (H3N2) virus. ABA treatment did not ameliorate epithelial necrosis (FIG. A), but it diminished the extent of vascular infiltrates (C) as well as the infiltration of respiratory airways mucosa and submucosa (D) when compared to animals fed the control diet. The lower number of inflammatory cells in the lungs of infected WT mice correlated with downregulation of the chemokine monocyte chemoattractant protein-1
Figure 15B:
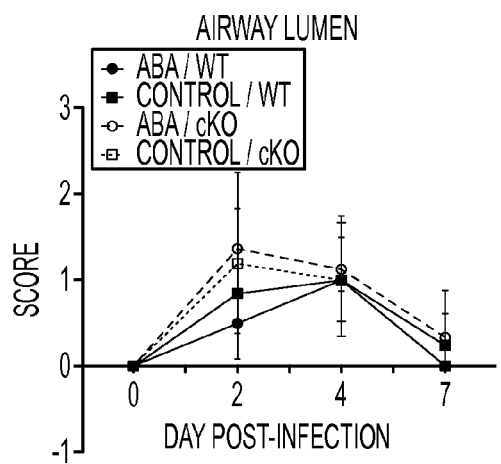
Figure 15C:
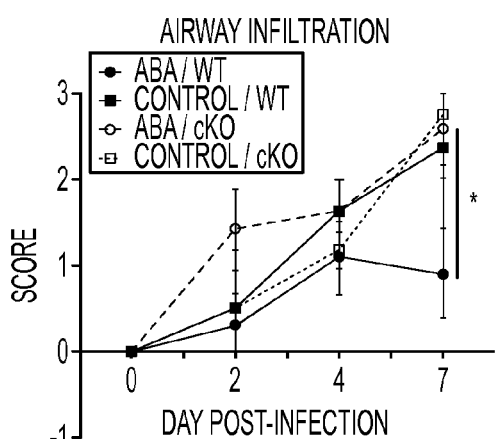
Figure 15D:
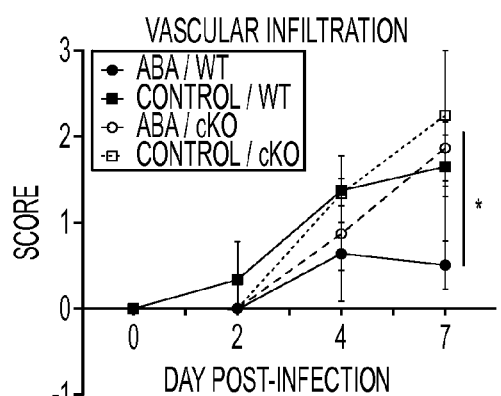
Figure 15E:
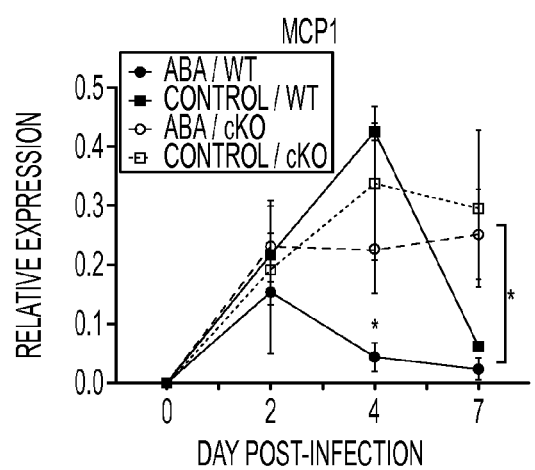
Figure 16A:
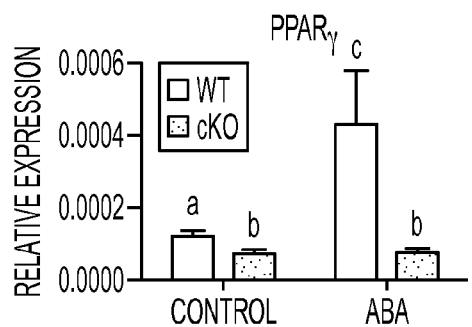
Figure 16B:
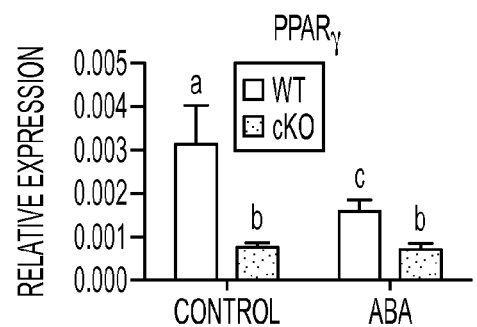
Figure 16C:
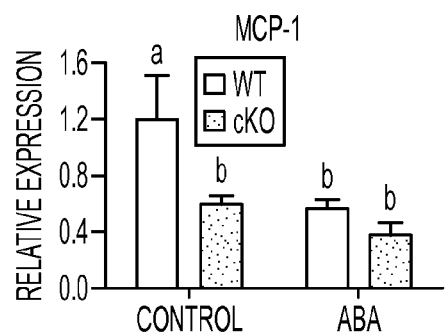
Figure 16D:
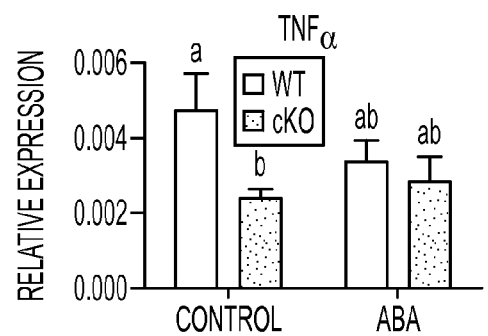

We had previously shown that ABA treatment suppressed macrophage infiltration into the white adipose tissue of obese mice in part by suppressing the expression of MCP-1 (3). The expression of this chemokine during infection and inflammation is regulated by NF-κB binding to its promoter region, a process that is sensitive to inhibition by activated PPAR γ. We then evaluated how ABA affected the expression of MCP-1 overtime in the lungs of mice challenged with Influenza A/Udorn strain. FIG. 14 E confirms that the group of WT mice that received ABA had consistently lower levels of MCP-1 mRNA expression compared to mice fed the control diet. Our data also shows that cKO mice failed to down-regulate MCP-1 expression following ABA treatment, whereas in the WT irrespective of the diet, MCP-1 mRNA levels dropped to almost pre-challenge levels by day 7. These results confirm the relevance of PPAR γ expression in the regulation of pulmonary inflammation by ABA.

Effect of ABA on influenza virus infection-associated inflammatory gene expression in BAL-derived cells Our cKO mice have deficient PPAR γ expression in immune and epithelial cells (13, 73). Because PPAR γ is highly expressed in the lungs by different cell types besides immune and epithelial cells, we measured gene expression in the bronchoalveolar space. This compartment is composed mainly by infiltrated immune and dying or apoptotic epithelial cells, which allows us to assess in a more restricted way the role of PPAR γ in regulating inflammation triggered by the flu virus. Real time RT-PCR showed that ABA treatment significantly increased the expression of PPAR γ in BAL-derived cells (FIG. 15 A). Interestingly, following infection PPAR γ mRNA levels were higher in WT mice of the control diet group (FIG. 15 B), which correlated with higher expression of MCP-1 (FIG. 15 C). These results confirmed that ABA down-regulates the expression of proinflammatory mediators in the lungs of mice infected with influenza A virus.

Discussion

ABA is an elusive phytohormone that plays important roles in the plant life cycle as well as regulation of immune responses (74). Our results show for the first time that ABA ameliorates influenza-virus induced pathology though a mechanism that depends on the full expression of PPAR γ in the lung. In these experiments we have used mice with defective PPAR γ expression in immune and epithelial cells. The epithelial compartment is the main target of influenza virus and where antiviral and subsequent immune responses are initiated. Our analyses of microscopic lesions however, indicate that ABA treatment does not significantly change the impact of the infection in epithelial necrosis. This result is likely due to the fact that ABA does have any direct effect on virus replication and infectivity. The main pathological improvement of oral ABA administration is the diminished infiltration of inflammatory leukocytes in wild type mice, which correlates with a sustained down-regulation of MCP-1 mRNA expression. These data are consistent with the transrepression of proinflammatory gene expression by activated PPAR γ. These results are in line with the ability of ABA to suppress macrophage infiltration into the white adipose tissue and MCP-1 expression in the stromal vascular fraction of obese mice (3). Moreover, Aldridge et al have shown that a synthetic PPAR γ agonist, pioglitazone diminished the accumulation of pro-inflammatory tip-DC by partially suppressing MCP-1 and MCP-3 production in response to highly pathogenic IAV (75).

When we analyzed the impact of ABA in cells residing in the alveolar space, we found that in healthy wild type mice ABA treatment enhanced PPAR γ mRNA expression in BAL-derived cells. PPAR γ is highly expressed in the lungs. The alveolar macrophage in particular expresses high levels of PPAR γ constitutively whereas other types of macrophages, such as those of the peritoneal cavity, upregulate PPAR γ only upon activation with proinflammatory stimuli. We show that in health mice, administration of ABA significantly enhances the expression of PPAR γ in cells obtained by bronchoalveolar lavage, which correspond mainly to alveolar macrophages. In contrast, upon infection, we detected higher expression of PPAR γ in wild type mice of the control group.

The possibility that the extent of the host immune response to influenza virus infection contributes to the pathogenesis of the disease was first postulated in 2007 based on findings of high levels of proinflammatory cytokines and chemokines in serum of hospitalized patients infected with influenza A virus. The hypercytokinemia hypothesis was later confirmed in experimental animal models, including mice, non-human primates, pigs and ferrets challenged with the highly pathogenic strains H5N1 and the reconstructed 1918 H1N1. Although the presence of high levels of inflammatory mediators is common for these two strains of influenza A virus, a recent report by Garigliani et al. shows that two subtypes of mouse-adapted influenza A virus, an H1N1 and H5N1 of equal pathogenicity induced different lesions. The lungs of mice infected with the H1N1 strain showed extensive epithelial damage and an infiltrative pattern characterized by the presence of inflammatory leukocytes surrounding blood vessels and respiratory airways with little or no edema. On the other hand, lungs from mice infected with the H5N1 subtype showed mild affection of the airway epithelium, alveolar edema and hemorrhage with low numbers of inflammatory leukocytes. These authors argue against the existence of a common mechanism of immunopathogenesis dominated by the elevated secretion of chemokines and cytokines.

We demonstrated that oral ABA administration decreased inflammation and improved clinical outcomes in mouse models of obesity-related inflammation, diabetes, atherosclerosis and inflammatory bowel disease (2-6). Mechanistically, these beneficial effects appeared to be linked to modulation of PPAR γ activity. Indeed, we soon demonstrated that ABA treatment activates PPAR γ in 3T3-L1 pre-adipocytes (4). In addition, the blood glucose-lowering actions of ABA required the expression of PPAR γ in immune cells (3). Surprisingly, ABA synergized with rosiglitazone (Ros) to improve glucose tolerance and regulate macrophage accumulation in adipose tissue (2). Since Ros saturates the LBD of PPAR γ, the reported synergism between the compounds suggests that ABA might activate PPAR γ through an alternate mechanism that differs from that of the thiazolidinedione (TZDs) class of anti-diabetic drugs. Indeed, we recently demonstrated that both (+) and (-) ABA isomers can activate PPAR γ reporter activity in RAW macrophages independently of direct binding to the LBD of this receptor (68), suggesting the existence of a potential molecular target for ABA upstream of PPAR γ. We reported that ABA treatment increased intracellular cAMP accumulation in human aortic endothelial cells (5), splenocytes and macrophages (68). Our findings were in line with a report from Bruzzone and colleagues showed that ABA induced cAMP overproduction and PKA activation in insulin-secreting pancreatic eta-cell lines (7). We also demonstrated that the ABA-induced activation of PPAR γ reporter activity can be inhibited through blocking cAMP production or inhibiting PKA activity (2), suggesting that upstream cAMP/PKA signaling may be required for the alternative activation of PPAR γ by ABA. The G protein-coupled lanthionine synthetase C-like 2 (LANCL2) is a involved in the initiation of the cAMP signal in leukocytes that has been reported to play a role in the signaling of ABA in human granulocytes (32). We identified a putative ABA-binding site on the surface of LANCL2 (41) and demonstrated that knocking down LANCL2 in RAW macrophages by using siRNA impaired or abrogated the effect of ABA on PPAR v reporter activity (68). The increased expression of PPAR γ in BAL cells from ABA-treated mice is consistent with the mechanism of action described above and the clinical improvements observed in influenza-infected mice following ABA treatment are in line with the anti-inflammatory effects associated with PPAR γ activation. Specifically, PPAR γ suppresses the expression of pro-inflammatory cytokines and chemokines involved in the cytokine storm by antagonizing the activities of transcription factors, such as AP-1, STAT and NF-κB (10), enhancing nucleocytoplasmic shuttling of the activated p65 subunit of NF-κB (11), and targeting co-repressor complexes onto inflammatory gene promoters (12). We demonstrated that the antagonistic effects of ABA on NF-κB are mediated through a PPAR γ-dependent mechanism (68). Since the deletion of PPAR γ in immune and epithelial cells impaired the beneficial effects of ABA on influenza virus-associated weight loss, lung immunopathology and MCP-1 production, the immunotherapeutic actions of ABA during influenza virus infection are also mediated via a PPAR γ-dependent mechanism.

Example 3

Effect of Post-Exposure ABA Therapy on Influenza Virus-Associated Pulmonary Inflammation and Mechanism of Action Materials and Methods Animal Procedures. Eight week old PPAR γ flfl Lysozyme M-Cre+ mice, with a Cre recombinase targeted to the Lysozyme M-Cre promoter (Lysozyme M-Cre+, n=20), lacking PPAR γ in myeloid cells, and wild-type (WT, n=20) mice in a C57BL/6 background were housed at the animal facilities at Virginia Tech. in a room maintained at 75° F., with a 12:12 h light-dark cycle starting from 6:00 AM. One-month old mice (n=10 for each treatment and genotype) were treated with 100 mg/kg body weight of ABA via orogastric gavage following intranasal challenge with influenza virus and throughout the challenge period. All experimental procedures were approved by the Institutional Animal Care and Use Committee of Virginia Tech and met or exceeded requirements of the Public Health Service/National Institutes of Health and the Animal Welfare Act.

Influenza virus challenge. To investigate whether ABA diminishes the pulmonary inflammatory response, we infected PPAR γ fl/fl; lysozyme M-cre− (WT) and PPAR γ fl/fl; lysozyme M-cre+ (myeloid KO) mice intranasally with 5×10⁴ tissue culture infectious dose 50 (TCID)$_{50}$ Influenza A/Udorn (H3N2) or 500 TCID$_{50}$ of A/California/09 (H1N1) given in 50 μl of sterile PBS under anesthesia with xylazine and ketamine (50-150 mg/kg). Mock-infected mice received the same volume of PBS.

Pulmonary Histopathology. Lungs were inflated at necropsy and lung sections were fixed in 10% buffered neutral formalin, later embedded in paraffin, and then sectioned (5 μm) and stained with H&E stain for histological examination. Lungs were graded with a compounded histology score including the extent of 1) epithelial necrosis/regeneration, 2) presence of desquamated cells and inflammatory cellular infiltrates within the airways, 3) presence of leukocytic infiltrates in epithelium and lamina propria of airways, 4) presence of marginated leukocytes and inflammatory cells surrounding blood vessels and, and 5) presence of edema, fibrin deposits or hyaline membranes. The sections were graded with a score of 0-4 for each of the previous categories and data were analyzed as a normalized compounded score.

Real-time RT-PCR. Total RNA was isolated from the lungs and BAL-derived cells using the RNA isolation Minikit (Qiagen) according to the manufacturer's instructions. Total RNA (0.5 to 1 μg) was used to generate complementary DNA (cDNA) template using the iScript cDNA Synthesis Kit (Bio-Rad, Hercules, Calif.). Starting cDNA concentrations for genes of interest were examined by real-time quantitative PCR using an iCycler IQ System and the iQ SYBR green supermix (Bio-Rad). A standard curve was generated for each gene using 10-fold dilutions of purified amplicons starting at 5 pg of cDNA and used later to calculate the starting amount of target cDNA in the unknown samples. PCR was performed on the cDNA using Taq DNA polymerase (Invitrogen, Carlsbad, Calif.) and using previously described conditions (13). Each gene amplicon was purified with the MiniElute PCR Purification Kit (Qiagen) and quantitated on an agarose gel by using a DNA mass ladder (Promega). These purified amplicons were to generate standard curves in the real-time PCR assay. Real-time PCR was used to measure the starting amount of nucleic acid of each unknown sample of cDNA on the same 96-well plate.

Statistical analyses. Data were analyzed as a 2×2 factorial arrangement of treatments within completely randomized design. The statistical model was: $Y_{ijk}=\mu+\text{Genotype}_i+\text{Treatment}_j+(\text{Genotype}\times\text{Treatment})_{ij}+\text{error} A_{ijk}$, in which μ was the general mean, Genotype$_i$ was the main effect of the $i_{th}$ level of the genotypic effect (expression of PPAR γ by myeloid cells), Treatment$_j$ was the main effect of the $j_{th}$ level of the gavage (ABA vs control), (Genotype×Treatment)$_{ij}$ was the interaction effect between genotype and post-exposure ABA, and error A representing the random error. To determine the statistical significance of the model, analysis of variance (ANOVA) was performed using the general linear model procedure of Statistical Analysis Software (SAS), and probability value (P)<0.05 was considered to be significant. When the model was significant, ANOVA was followed by Fisher's Protected Least Significant Difference multiple comparison method.

Results

Effect of post-exposure therapeutic ABA on influenza-related weight loss and pulmonary immune cell infiltration. The initial results were obtained following prophylactic administration of ABA. We have tested the ability of ABA to ameliorate disease when given therapeutically. In this case, WT mice were infected with 5×10⁴ TCID$_{50}$ of Influenza A/Udorn (H3N2) or 500 TCID$_{50}$ of A/California/09 (H1N1), and ABA was given by oral gavage, starting 4 hours post-infection, once daily for the following 10 days. As shown in FIG. 17, ABA given at 100 mg/kg suppressed weight loss for both strains and accelerated recovery. In mice challenged with A/Udorn, ABA at 50 mg/kg slightly suppressed weight loss, although the differences were not statistically significant compared to mice in non-treated mice (blue vs red lines). FACS analysis on lung digests obtained 7 dpi, show that ABA at 100 mg/kg lowered the accumulation of pro-inflammatory tipDC (FIG. 18), identified following the scheme represented in FIG. 18, as MHC-II$^{hi}$ Ly6c$^{hi}$ within the CD11c. Note that alveolar macrophages were excluded from the analysis based on CD11c expression and SSC properties. These findings were paralleled by lowered expression of MCP-1 at 3 and 7 dpi in lungs of infected mice that were treated with ABA as shown in the bottom panel of FIG. 18 Overall our data support the hypothesis that PPAR γ activation by exogenously administered agonists, prophylactically or therapeutically, suppresses the inflammatory response triggered by influenza A virus infection.

Effect of post-exposure therapeutic ABA on pulmonary histopathological lesions during influenza virus challenge. Post-exposure ABA treatment ameliorated mucosal and sub-mucosal inflammatory cell infiltration, terminal airway infiltration, perivascular cuffing and epithelial necrosis in the lungs of mice infected with H3N2 influenza virus (FIG. 19). The beneficial effects of ABA on H3N2 influenza-associated lung inflammatory lesions were abrogated in mice lacking PPAR γ in myeloid cells (myeloid KO), suggesting that expression of PPAR γ in macrophages and/or dendritic cells is necessary for the therapeutic efficacy of ABA (FIG. 19).

Effect of post-exposure therapeutic ABA on pulmonary gene expression during influenza virus challenge. Post-exposure ABA treatment following influenza virus challenge resulted in upregulation of pulmonary PPAR γ, LANCL2, 5-lipooxygenase (5-LOX), 5-LOX activating protein (FLAP) on day 10 post-infection (FIG. 20). In addition, ABA upregulated pulmonary interleukin-10 (IL-10) and angiopoietin like 4 (ANGIOPL4) mRNA expression in the lung on day 7 post-infection (FIG. 21).

Effect of post-exposure therapeutic ABA on glucose tolerance and white adipose tissue MCP-1 levels in uninfected and H1N1-infected mice. Obesity and diabetes are two worldwide epidemics and these conditions were suspected to worsen disease severity in H1N1-infected individuals during the 2009 pandemic. We demonstrated that ABA treatment ameliorated glucose tolerance both in lean and obese mice infected with H1N1 influenza virus and uninfected control mice (FIG. 22). These results indicate that ABA treatment ameliorates both influenza and its inflammatory co-morbidities (i.e., diabetes, overweight, obesity and metabolic syndrome) that increase severity and mortality associated with influenza. ABA also down-regulated MCP-1 expression in the white adipose tissue of uninfected mice (FIG. 23).

Example 4

Effect of ABA Treatment on Antigen-Specific Immune Responses Following Influenza Virus Vaccination Materials and Methods Animal Procedures. Eight week old PPAR γ flfl MMTV-Cre+ mice, with a Cre recombinase targeted to the MMTV- Cre promoter (MMTV-Cre+), lacking PPAR γ in hematopoietic cells, and wild-type (WT) mice in a C57BL/6 background were housed at the animal facilities at Virginia Tech. in a room maintained at 75° F., with a 12:12 h light-dark cycle starting from 6:00 AM. One-month old mice (n=10 for each treatment, genotype and time) were administered control or ABA-supplemented diets (100 mg ABA/kg) for 36 days and immunized (on day 37) with inactivated influenza virus PR8 antigens (5 pg per mouse i.m.). Mice were euthanized on days 14 and 21 post-vaccination to measure the effect of ABA on antigen-specific immune responses to influenza vaccination. All experimental procedures were approved by the Institutional Animal Care and Use Committee of Virginia Tech and met or exceeded requirements of the Public Health Service/National Institutes of Health and the Animal Welfare Act.

Isolation of splenocytes. Spleens were excised, crushed using the frosted ends of two microscope slides. The single cell suspension was centrifuged at 400 g for 12 minutes and freed of red blood cells by osmotic lysis. Pellets were washed with PBS and resuspended in complete RPMI (supplemented with 10% fetal bovine serum (Hyclone), 25 mM HEPES buffer (Sigma), 100 units/ml penicillin (Sigma), 0.1 mg/ml streptomycin (Sigma), 1 mM sodium pyruvate (Sigma), 1 mM non-essential aminoacids (Sigma), 2 mM essential amino acids (Mediatech) and 2-ME). Cells were enumerated by using a Coulter Counter (Beckman Coulter, Fullerton, Calif.) and cell concentration adjusted at $2\times10^6$ cells/ml for functional assays.

Lymphocyte proliferation assay. Splenocytes were stimulated in 96-well round bottom plates with media alone (non-stimulated wells) or medium containing inactivated antigens of influenza virus strain PR8 (PR8) or unrelated ovalbumin antigen (OVA, 5 μg/mL). Concanavalin A (Con A) at 5 μg/mL was used as a positive control for proliferation. Antigen-specific proliferation was measured on day 5. Cultures were pulsed for the last 20 h with 0.5 mCi of [$^3$H]-Thymidine. Overall lymphocyte proliferation was expressed as stimulation indices, which were calculated by dividing the counts per minute (cpm) of antigen-stimulated wells by the cpm of non-stimulated wells.

Statistical analyses. Data were analyzed as a repeated measures factorial arrangement of treatments (genotype by diet by vaccine by time) within completely randomized design. To determine the statistical significance of the model, analysis of variance (ANOVA) was performed using the general linear model procedure of Statistical Analysis Software (SAS), and probability value (P)<0.05 was considered to be significant. When the model was significant, ANOVA was followed by Fisher's Protected Least Significant Difference multiple comparison method.

Results

Dietary ABA supplementation increased antigen-specific lymphoproliferative recall responses to influenza virus vaccination on days 14 and 21 post-vaccination (FIG. 24). The immunostimulatory effect of ABA on immune responses to influenza vaccination was attenuated in mice lacking PPAR γ in immune cells (FIG. 24). These results indicated that ABA treatment may be used as an adjunct therapy to increase vaccine efficacy.

It will be apparent to those skilled in the art that various modifications and variations can be made in the practice of the present invention without departing from the scope of the invention. Other embodiments of the invention will be apparent to those skilled in the art from consideration of the specification and practice of the invention. It is intended that the specification and examples be considered as exemplary only, with a true scope and spirit of the invention being indicated by the following claims.

REFERENCES

1. Bassaganya-Riera J, Skoneczka J, Kingston D G J, et al. Mechanisms of action and medicinal applications of abscisic acid. Current Medicinal Chemistry 2009; In press.
2. Guri A J, Hontecillas R, Bassaganya-Riera J. Abscisic acid synergizes with rosiglitazone To improve glucose tolerance and down-modulate macrophage accumulation in adipose tissue: possible action of the cAMP/PKA/PPAR gamma axis. Clinical Nutrition 2010; In Press.
3. Guri A J, Hontecillas R, Ferrer G, et al. Loss of PPAR gamma in immune cells impairs the ability of abscisic acid to improve insulin sensitivity by suppressing monocyte chemoattractant protein-1 expression and macrophage infiltration into white adipose tissue. J Nutr Biochem 2008; 19:216-28.
4. Guri A J, Hontecillas R, Si H, Liu D, Bassaganya-Riera J. Dietary abscisic acid ameliorates glucose tolerance and obesity-related inflammation in db/db mice fed high-fat diets. Clin Nutr 2007;26:107-16.
5. Guri A J, Misyak S, Hontecillas R, et al. Abscisic acid ameliorates atherosclerosis by suppressing macrophage and CD4+ T cell recruitment into the aortic wall. Journal of Nutritional Biochemistry 2010; In Press.
6. Guri A J, Hontecillas R, Bassaganya-Riera J. Abscisic acid ameliorates experimental IBD by downregulating cellular adhesion molecule expression and suppressing immune cell infiltration. Clinical Nutrition 2010;In Press.
7. Bruzzone S, Bodrato N, Usai C, et al. Abscisic Acid Is an Endogenous Stimulator of Insulin Release from Human Pancreatic Islets with Cyclic ADP Ribose as Second Messenger. J Biol Chem 2008;283:32188-32197.
8. Lehmann J M, Moore L B, Smith-Oliver T A, Wilkison W O, Willson T M, Kliewer S A. An antidiabetic thiazolidinedione is a high affinity ligand for peroxisome proliferator-activated receptor gamma (PPAR gamma). J Biol Chem 1995;270:12953-6.
9. Jump D B, Clarke S D. Regulation of gene expression by dietary fat. Annu Rev Nutr 1999;19:63-90.
10. Ricote M, Li A C, Willson T M, Kelly C J, Glass C K. The peroxisome proliferator-activated receptor-gamma is a negative regulator of macrophage activation. Nature 1998; 391:79-82.
11. Kelly D, Campbell J I, King T P, et al. Commensal anaerobic gut bacteria attenuate inflammation by regulating nuclear-cytoplasmic shuttling of PPAR-gamma and RelA. Nat Immunol 2004;5:104-12.
12. Pascual G, Fong A L, Ogawa S, et al. A SUMOylation-dependent pathway mediates transrepression of inflammatory response genes by PPAR-gamma. Nature 2005;437: 759-63.
13. Bassaganya-Riera J, Reynolds K, Martino-Catt S, et al. Activation of PPAR gamma and delta by conjugated linoleic acid mediates protection from experimental inflammatory bowel disease. Gastroenterology 2004;127: 777-91.
14. Kim S R, Lee K S, Park H S, et al. Involvement of IL-10 in peroxisome proliferator-activated receptor gamma-mediated anti-inflammatory response in asthma. Mol Pharmacol 2005;68:1568-75.
15. Hammad H, de Heer H J, Soullie T, et al. Activation of peroxisome proliferator-activated receptor-gamma in dendritic cells inhibits the development of eosinophilic airway inflammation in a mouse model of asthma. Am J Pathol 2004;164:263-71.
16. Lewis J D, Lichtenstein G R, Deren J J, et al. Rosiglitazone for active ulcerative colitis: a randomized placebo-controlled trial. Gastroenterology 2008;134:688-95.
17. Nesto R W, Bell D, Bonow R O, et al. Thiazolidinedione use, fluid retention, and congestive heart failure: a consensus statement from the American Heart Association and American Diabetes Association. Oct. 7, 2003. Circulation 2003;108:2941-8.
18. Yang T, Soodvilai S. Renal and vascular mechanisms of thiazolidinedione-induced fluid retention. PPAR Res 2008;2008:943614.
19. Pettersen E, Goddard T, Huang C, et al. UCSF Chimera—a visualization system for exploratory research and analysis. Journal of Computational Chemistry 2004;25: 1605-1612.
20. Gampe R T, Montana V G, Lambert M H, et al. Asymmetry in the PPARg/RXRa Crystal Structure Reveals the Molecular Basis of Heterodimerization among Nuclear Receptors. Molecular Cell 2000;5:545-555.
21. Shirey K A, Cole L E, Keegan A D, Vogel S N. Francisella tularensis live vaccine strain induces macrophage alternative activation as a survival mechanism. J Immunol 2008; 181:4159-67.
22. Hontecillas R, Bassaganya-Riera J. Peroxisome proliferator-activated receptor gamma is required for regulatory CD4+ T cell-mediated protection against colitis. J Immunol 2007;178:2940-9.
23. Bassaganya-Riera J, Misyak S, Guri A J, Hontecillas R. PPAR gamma is highly expressed in F4/80(hi) adipose tissue macrophages and dampens adipose-tissue inflammation. Cell Immunol 2009;258:138-146.
24. Willems F, Vollstedt S, Suter M. Phenotype and function of neonatal DC. Eur J Immunol 2009;39:26-35.
25. Gentleman R C, Carey V J, Bates D M, et al. Bioconductor: open software development for computational biology and bioinformatics. Genome Biol 2004;5:R80.
26. Gautier L, Cope L, Bolstad B M, Irizarry RA. affy—analysis of Affymetrix GeneChip data at the probe level. Bioinformatics 2004;20:307-15.
27. Irizarry R A, Hobbs B, Collin F, et al. Exploration, normalization, and summaries of high density oligonucleotide array probe level data. Biostatistics 2003;4:249-64.
28. SAS. SAS/STAT User's guide (Release 6.0.3). Cary, N C: SAS Inst. Inc., 1988.
29. Gampe R T, Montana V G, Lambert M H, et al. Asymmetry in the PPAR gamma/RXR alpha crystal structure reveals the molecular basis of heterodimerization among nuclear receptors. Molecular Cell 2000;5:545-555.
30. Itoh T, Fairall L, Amin K, et al. Structural basis for the activation of PPARgamma by oxidized fatty acids. Nat Struct Mol Biol 2008;15:924-31.
31. Nolte R T, Wisely G B, Westin S, et al. Ligand binding and co-activator assembly of the peroxisome proliferator-activated receptor-gamma. Nature 1998;395:137-43.
32. Sturla L, Fresia C, Guida L, et al. LANCL2 is necessary for abscisic acid binding and signaling in human granulocytes and in rat insulinoma cells. J Biol Chem 2009;284: 28045-57.
33. Bruzzone S, Bodrato N, Usai C, et al. Abscisic acid is an endogenous stimulator of insulin release from human pancreatic islets with cyclic ADP ribose as second messenger. J Biol Chem 2008;283:32188-97.
34. Magnone M, Bruzzone S, Guida L, et al. Abscisic acid released by human monocytes activates monocytes and vascular smooth muscle cell responses involved in atherogenesis. J Biol Chem 2009.
35. Welch J S, Ricote M, Akiyama T E, Gonzalez F J, Glass C K. PPARgamma and PPARdelta negatively regulate specific subsets of lipopolysaccharide and IFN-gamma target genes in macrophages. Proc Natl Acad Sci USA 2003;100: 6712-7.
36. Crosby M B, Svenson J L, Zhang J, Nicol C J, Gonzalez F J, Gilkeson G S. Peroxisome proliferation-activated receptor (PPAR)gamma is not necessary for synthetic PPARgamma agonist inhibition of inducible nitric-oxide synthase and nitric oxide. J Pharmacol Exp Ther 2005;312: 69-76.
37. Tsavkelova E A, Klimova S, Cherdyntseva T A, Netrusov A I. [Hormones and hormone-like substances of microorganisms: a review]. Prikl Biokhim Mikrobiol 2006;42: 261-8.
38. Zocchi E, Carpaneto A, Cerrano C, et al. The temperature-signaling cascade in sponges involves a heat-gated cation channel, abscisic acid, and cyclic ADP-ribose. Proc Natl Acad Sci USA 2001;98:14859-64.
39. Zocchi E, Basile G, Cerrano C, et al. ABA- and cADPR-mediated effects on respiration and filtration downstream of the temperature-signaling cascade in sponges. J Cell Sci 2003:116:629-36.
40. Bruzzone S, Moreschi I, Usai C, et al. Abscisic acid is an endogenous cytokine in human granulocytes with cyclic ADP-ribose as second messenger. Proc Natl Acad Sci USA 2007;104:5759-64.
41. Lu P, Bevan D R, Lewis S N, Hontecillas R, Bassaganya-Riera J. Molecular modeling of lanthionine synthetase component C-like 2: a potential target for the discovery of novel type 2 diabetes prophylactics and therapeutics. Journal of Molecular Modeling 2010; In press.
42. Chung C H, Kurien B T, Mehta P, et al. Identification of lanthionine synthase C-like protein-1 as a prominent glutathione binding protein expressed in the mammalian central nervous system. Biochemistry 2007;46:3262-9.
43. Zhang W, Wang L, Liu Y, et al. Structure of human lanthionine synthetase C-like protein 1 and its interaction with Eps8 and glutathione. Genes Dev 2009;23:1387-92.
44. Lazennec G, Canaple L, Saugy D, Wahli W. Activation of peroxisome proliferator-activated receptors (PPARs) by their ligands and protein kinase A activators. Mol Endocrinol 2000;14:1962-75.
45. Saito Y, Okamura M, Nakajima S, et al. Suppression of nephrin expression by TNF-{alpha} via interfering with the cAMP-retinoic acid receptor pathway. Am J Physiol Renal Physiol 2010.
46. Dubuquoy L, Jansson E E, Deeb S, et al. Impaired expression of peroxisome proliferator-activated receptor gamma in ulcerative colitis. Gastroenterology 2003;124:1265-76.
47. Szanto A, Nagy L. Retinoids potentiate peroxisome proliferator-activated receptor gamma action in differentiation, gene expression, and lipid metabolic processes in developing myeloid cells. Mol Pharmacol 2005;67:1935-43.
48. Adolfsson O, Huber B T, Meydani S N. Vitamin E-enhanced IL-2 production in old mice: naive but not memory T cells show increased cell division cycling and IL-2-producing capacity. J Immunol 2001;167:3809-17.
49. O'Shea M, Bassaganya-Riera J, Mohede I C. Immunomodulatory properties of conjugated linoleic acid. Am J Clin Nutr 2004;79:1199S-1206S.

50. Csanady L, Torocsik B. Four Ca2+ ions activate TRPM2 channels by binding in deep crevices near the pore but intracellularly of the gate. J Gen Physiol 2009;133:189-203.

51. Agrawal A, Guttapalli A, Narayan S, Albert T J, Shapiro I M, Risbud M V. Normoxic stabilization of HIF-1alpha drives glycolytic metabolism and regulates aggrecan gene expression in nucleus pulposus cells of the rat intervertebral disk. Am J Physiol Cell Physiol 2007;293:C621-31.

52. Nechushtan H, Kim S, Kay G, Razin E. Chapter 1: The physiological role of lysyl tRNA synthetase in the immune system. Adv Immunol 2009;103:1-27.

53. Park S G, Kim H J, Min Y H, et al. Human lysyl-tRNA synthetase is secreted to trigger proinflammatory response. Proc Natl Acad Sci USA 2005;102:6356-61.

54. Levine S M, Rosen A, Casciola-Rosen L A. Anti-aminoacyl tRNA synthetase immune responses: insights into the pathogenesis of the idiopathic inflammatory myopathies. Curr Opin Rheumatol 2003;15:708-13.
55. Yang C R, Lai CC. Thiazolidinediones inhibit TNF-alpha-mediated osteoclast differentiation of RAW264.7 macrophages and mouse bone marrow cells through downregulation of NFATc1. Shock 2009.
56. Baillie R A, Sha X, Thuillier P, Clarke S D. A novel 3T3-L1 preadipocyte variant that expresses PPARgamma2 and RXRalpha but does not undergo differentiation. J Lipid Res 1998;39:2048-53.

57. Chung S W, Kang B Y, Kim T S. Inhibition of interleukin-4 production in CD4+ T cells by peroxisome proliferator-activated receptor-gamma (PPAR-gamma) ligands: involvement of physical association between PPAR-gamma and the nuclear factor of activated T cells transcription factor. Mol Pharmacol 2003;64:1169-79.

58. Teismann P, Tieu K, Cohen O, et al. Pathogenic role of glial cells in Parkinson's disease. Mov Disord 2003;18:121-9.

59. Herrera A J, Castano A, Venero J L, Cano J, Machado A. The single intranigral injection of LPS as a new model for studying the selective effects of inflammatory reactions on dopaminergic system. Neurobiol Dis 2000;7:429-47.

60. Jaeger L B, Dohgu S, Sultana R, et al. Lipopolysaccharide alters the blood-brain barrier transport of amyloid beta protein: a mechanism for inflammation in the progression of Alzheimer's disease. Brain Behav Immun 2009;23:507-17.

61. Butterfield D A, Drake J, Pocernich C, Castegna A. Evidence of oxidative damage in Alzheimer's disease brain: central role for amyloid beta-peptide. Trends Mol Med 2001;7:548-54.

62. McGillicuddy F C, de la Llera Moya M, Hinkle C C, et al. Inflammation impairs reverse cholesterol transport in vivo. Circulation 2009;119:1135-45.

63. Kueht M L, McFarlin B K, Lee R E. Severely obese have greater LPS-stimulated TNF-alpha production than normal weight African-American women. Obesity (Silver Spring) 2009;17:447-51.

64. de Jong M D, Simmons C P, Thanh T T, et al. Fatal outcome of human influenza A (H5N1) is associated with high viral load and hypercytokinemia. Nat Med 2006;12:1203-7.

65. Kash J C, Tumpey T M, Proll S C, et al. Genomic analysis of increased host immune and cell death responses induced by 1918 influenza virus. Nature 2006;443:578-81.

66. Gill J R, Sheng Z M, Ely S F, et al. Pulmonary Pathologic Findings of Fatal 2009 Pandemic Influenza A/H1N1 Viral Infections. Arch Pathol Lab Med 2010;134:235-43.

67. Lewis S N, Bassaganya-Riera J, Bevan D R. Virtual screening as a technique for PPAR modulator discovery. PPAR Res 2009;In press.

68. Bassaganya-Riera J, Guri A J, Lu P, et al. Abscisic acid regulates inflammation via ligand-binding domain-independent activation of PPAR gamma. Journal of Biological Chemistry 2010; In press.

69. Guri A J, Evans N P, Hontecillas R, Bassaganya-Riera J. T cell PPAR gamma is required for the anti-inflammatory efficacy of abscisic acid against experimental IBD. Journal of Nutritional Biochemistry 2010; In press.
70. Herbert A S, Heffron L, Sundick R, Roberts P C. Incorporation of membrane-bound, mammalian-derived immunomodulatory proteins into influenza whole virus vaccines boosts immunogenicity and protection against lethal challenge. Virol J 2009;6:42.
71. Reed L J, Muench H. A simple method of estimating fifty percent end points. Am j Hyg 1938;27:493-497.
72. Becker J, Delayre-Orthez C, Frossard N, Pons F. Regulation of inflammation by PPARs: a future approach to treat lung inflammatory diseases? Fundam Clin Pharmacol 2006;20:429-47.
73. Cui Y, Miyoshi K, Claudio E, et al. Loss of the peroxisome proliferation-activated receptor gamma (PPARgamma) does not affect mammary development and propensity for tumor formation but leads to reduced fertility. J Biol Chem 2002;277:17830-5.
74. Bassaganya-Riera J, Skoneczka J, Kingston DG, et al. Mechanisms of action and medicinal applications of abscisic Acid. Curr Med Chem 2010;17:467-78.
75. Aldridge J R, Jr., Moseley C E, Boltz D A, et al. TNF/iNOS-producing dendritic cells are the necessary evil of lethal influenza virus infection. Proc Natl Acad Sci USA 2009;106:5306-11.

What is claimed is:

1. A method of treating respiratory inflammation in a mammal, the method comprising administering to the mammal a composition containing one or more compounds selected from: abscisic acid (ABA) in its free acid form, esters thereof, pharmaceutically suitable salts thereof, metabolites thereof, structurally related compounds thereof, and analogs thereof, in amounts that are sufficient to decrease mucosal and submucosal inflammatory cell infiltration, perivascular cuffing, terminal airway infiltration, or epithelial necrosis in the lung, wherein the inflammation is caused by an infection of a respiratory pathogen selected from the group consisting of influenza virus rhinovirus respiratory syncytial virus, parainfluenza, *Staphylococcus aureus, Streptococcus pneumoniae, Francisella tularensis, Mycobacterium tuberculosis* and *Bacillus anthracis*.

2. The method of claim 1, wherein the composition further contains a carrier.

3. The method of claim 2, wherein the carrier is a nutritional supplement, functional food, or dietary aid.

4. The method of claim 1, wherein the one or more compounds is abscisic acid in its free acid form.

5. The method of claim 4, wherein the abscisic acid in its free acid form is chemically synthesized.

6. The method of claim 4, wherein the amount of the composition is also sufficient to decrease accumulation of tipDC in the lungs.

* * * * *